US 8,086,471 B2

(12) United States Patent
Gamboa et al.

(10) Patent No.: US 8,086,471 B2
(45) Date of Patent: Dec. 27, 2011

(54) COMPUTER-IMPLEMENTED SYSTEM AND METHOD FOR ELECTRONIC MEDICATION ADMINISTRATION RECORDS

(75) Inventors: Mona Gamboa, Jelm, WY (US);
Timothy W. Renz, Casper, WY (US);
Jeffrey Van Baalen, Laramie, WY (US);
Ruben Gamboa, Jelm, WY (US)

(73) Assignee: Emissary Technologies, LLC, Casper, WY (US)

( * ) Notice: Subject to any disclaimer, the term of this patent is extended or adjusted under 35 U.S.C. 154(b) by 191 days.

(21) Appl. No.: 12/429,907

(22) Filed: Apr. 24, 2009

(65) Prior Publication Data

US 2010/0274587 A1    Oct. 28, 2010

(51) Int. Cl.
*G06Q 10/00* (2006.01)
*G06Q 50/00* (2006.01)
*A61B 5/00* (2006.01)
*G06F 19/00* (2006.01)

(52) U.S. Cl. ............................................. 705/2; 705/3
(58) Field of Classification Search .................. 705/2, 3
See application file for complete search history.

(56) References Cited

U.S. PATENT DOCUMENTS

| | | | |
|---|---|---|---|
| 4,857,713 A | 8/1989 | Brown | |
| 5,077,666 A | 12/1991 | Brimm et al. | |
| 5,536,084 A | 7/1996 | Curtis et al. | |
| 5,842,976 A | 12/1998 | Williamson | |
| 6,021,392 A | 2/2000 | Lester et al. | |
| 6,032,155 A | 2/2000 | de la Huerga | |
| 6,347,329 B1 | 2/2002 | Evans | |
| 6,994,249 B2 | 2/2006 | Peterka et al. | |
| 7,155,306 B2 | 12/2006 | Haitin et al. | |
| 7,278,579 B2 | 10/2007 | Loffredo et al. | |
| 7,286,997 B2 | 10/2007 | Spector et al. | |
| 7,301,451 B2 | 11/2007 | Hastings | |
| 7,364,067 B2 | 4/2008 | Steusloff et al. | |
| 2001/0044731 A1 | 11/2001 | Coffman et al. | |
| 2002/0095424 A1 | 7/2002 | Chung | |
| 2004/0172283 A1 | 9/2004 | Vanderveen et al. | |
| 2005/0143671 A1 | 6/2005 | Hastings et al. | |
| 2005/0146431 A1 | 7/2005 | Hastings et al. | |
| 2005/0148890 A1 | 7/2005 | Hastings | |
| 2005/0151640 A1 | 7/2005 | Hastings | |
| 2005/0171815 A1* | 8/2005 | Vanderveen .................. 705/3 |
| 2005/0187789 A1 | 8/2005 | Hatlestad et al. | |
| 2005/0261940 A1 | 11/2005 | Gay et al. | |
| 2006/0047538 A1 | 3/2006 | Condurso et al. | |
| 2006/0053036 A1 | 3/2006 | Coffman et al. | |
| 2006/0111941 A1* | 5/2006 | Blom ............................. 705/2 |
| 2006/0180659 A1 | 8/2006 | Loffredo et al. | |
| 2006/0287885 A1 | 12/2006 | Frick | |

(Continued)

*Primary Examiner* — Gerald J. O'Connor
*Assistant Examiner* — Neha Patel
(74) *Attorney, Agent, or Firm* — Antoinette M. Tease

(57) ABSTRACT

A system for electronic medication administration records comprising a cart station located at a skilled nursing facility, administration web pages, and a healthcare server not located at the skilled nursing facility. The cart station utilizes a plan builder algorithm to build a plan for each patient based on data contained in the cart station database. The plan comprises a list of the patient's procedures for a given day and information indicating whether such procedures have been completed. The cart station utilizes a plan runner algorithm to maintain and update the plan for each patient. The administration web pages allow an administrator to manage utilization of the system. The healthcare server and the cart station utilize a synchronization algorithm to maintain accurate and timely data for all of the skilled nursing facilities that use the system. A method of maintaining electronic medication administration records using the system described above.

22 Claims, 79 Drawing Sheets

U.S. PATENT DOCUMENTS

| | | |
|---|---|---|
| 2007/0185615 A1 | 8/2007 | Bossi et al. |
| 2008/0010089 A1 | 1/2008 | DiMaggio et al. |
| 2008/0046296 A1 | 2/2008 | Frick |
| 2008/0059228 A1 | 3/2008 | Bossi et al. |
| 2008/0065424 A1 | 3/2008 | Frick |
| 2008/0109260 A1 | 5/2008 | Roof |

* cited by examiner

Figure 12

Resident's Medication Profile

| Routine Meds | PRNs | Treatments | Procedures |
|---|---|---|---|

Medication Name (Dose) (Frequency) (Medication Periods) (Days)

(Not Active) Medication Name (Dose) (Frequency) (Medication Periods) (Days)
Generic Name Medication Name (Dose) (Frequency) (Medication Periods) (Days)

(Not Active) Medication Name (Dose) (Frequency) (Medication Periods) (Days)
Generic Name

Insulin Sliding Scale

Less Than 100 :(0.5) Insulin Unit(s)
101 - 150 :(0.5) Insulin Unit(s)
151 - 200 :(0.5) Insulin Unit(s)
201 - 250 :(0.5) Insulin Unit(s)
251 - 300 :(0.5) Insulin Unit(s)
301 - 350 :(0.5) Insulin Unit(s)
351 - 400 :(0.5) Insulin Unit(s)
Greater Than: 401: (7.5) Insulin Unit(s)

Back

D/C Medication

Doctor: Doctor Name — 62
Order Date: 02/05/2009 — 63
Order Type: D/C Medication

Medication to Discontinue
Fosomax
Comments

64

☑ Send Fax to Pharmacy?

Cancel  Submit
              66

New Routine Med

- Doctor: [Doctor Name ▼]
- Order Date: [02/05/2009] 📅
- Order Type: [New Medication ▼]
- ☐ Psychotropic — 105
- ☐ Narcotic

- Medication Name: [_____] ☐ Brand Only
- Dosage: [____]
- # of Doses: [__]
- ICD9: [____] — 110, 106
- 109, 100

- Frequency: [NONE ▼] 🕐 — 102
- Route: [By Mouth (PO) ▼]
- ☐ SUN ☐ MON ☐ TUE ☐ WED ☐ THU ☐ FRI ☐ SAT — 101
- Start Date: [02/05/2009] 📅
- End Date: [02/05/2009] 📅 [None] — 103

Prerequisites — 104
- ☐ Blood Pressure
- ☐ Blood Sugar
- ☐ Location
- ☐ Pain Level
- ☐ Pulse
- ☐ Pulse Oxygen
- ☐ Temperature
- ☐ Weight
- ☐ Sliding Scale Order Details: [_____]

[Cancel] [Submit]   ☑ Send Fax to Pharmacy?

New Treatment

Doctor: [Doctor Name ▼]
Order Date: [02/05/2009] 📅
Order Type: [New Treatment ▼]

Treatment Name:
111 — [Bandage Treatment ▼]    ICD9 [⌨]
112 — ☐ PRN
Frequency [NONE ▼] 🕐  ☐ SUN ☐ MON ☐ TUE ☐ WED ☐ THU ☐ FRI ☐ SAT
Start Date: [02/05/2009] 📅    End Date: [02/05/2009] 📅 [None]
Treatment Details
[                    ⌨]

[Cancel] [Submit]

Figure 40

Scheduled Procedure

Doctor: [Doctor Name ▾]
Order Date: [02/05/2009]
Order Type: [Schedule Procedure ▾]

Frequency: [NONE ▾]    SUN ☐ MON ☐ TUE ☐ WED ☐ THU ☐ FRI ☐ SAT ☐

Start Date: [02/05/2009]    End Date: [02/05/2009] [None]

Procedures:
○ Blood Pressure  ○ Blood Sugar  ○ Pain Level
○ Pulse           ○ Pulse Oxygen ○ Temperature
○ Weight

ICD9: [____]

Treatment Details:
[_____]

[Cancel] [Submit]

D/C All Medications

Doctor: [Doctor Name ▼]
Order Date: [02/05/2009] 📅
Order Type: [D/C All ▼]

Comments:
[                    ]

☑ Send Fax to Pharmacy?

[Cancel] [Submit]

Resident Name Detail

| Basic Info | Physician/Pharmacy | Other |

Medical Record #: 1234567
Medicare #: 123456789
Medicaid #: 123456789

Insurance Carrier: Carrier Name
Policy Number: 1234567890

Insurance Contact
  Contact Name
  Contact Phone
  Contact Address 1
  City    State    Zip Diet: Regular Admit Notes: None Allergies: Sulfa Drugs; Ciprofloxicin; Demerol; Codeine Diagnosis: Mild Dementia; Neritis; Diabetes; Osteoperosis; Congestive Heart Failure; Abnormal Mass in Chest; Dyspnea

[Close]

Figure 55

Define Frequency

Please select 4 periods

- ☐ Early AM  ☐ AM  ☐ Noon
- ☐ Early PM  ☐ PM  ☐ Supper
- ☐ HS  ☐ Late HS

[ Save ]

Edit Medication Times

| Period Meds | Hourly Meds |
|---|---|
| QID | Q1h |
| BID | Q2H |
| TID | Q4H |
| QD | Q406H |
| QOD | Q6H |
| Daily | Q12H |
| Q3DAY | Q24H |
| Weekly | Q48H |
| Bi-Weekly | Q72H |
| Monthly | |
| Quarterly | |

[ Add New Frequency ]
[ Save ]  [ Cancel ]

Reasons for Medications Not Given

Reasons in MedRight
- Blood Pressure too high
- Blood Pressure too low
- Held due to Nursing Judgment - Physician to be contacted
- Hold per Physician Parameters
- DOA
- Lethargic
- Nausea
- Order from Pharmacy - Awaiting Delivery
- Other (see Nurse Notes for details)
- Pulse too high
- Pulse too low
- Refused
- Sleeping

[Add new Reason] [Delete Selected Reason]

[Save] [Cancel]

Schedule for Resident Name

| Date | Caption | Type |
|---|---|---|
| Event Start Date/Time - Event End Date/Time | Event Caption | Event Type |
| Event Start Date/Time - Event End Date/Time | Event Caption | Event Type |
| Event Start Date/Time - Event End Date/Time | Event Caption | Event Type |
| Event Start Date/Time - Event End Date/Time | Event Caption | Event Type |

Month [▼]  Year [▼]

Month - Month
| 26 | 27 | 28 | 29 | 30 | 31 | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |

⊞ Add Event

Caption
Description

Start Date [____] ⊞
Start Time [00 ▼] : [00 ▼]
End Date [____] ⊞
End Time [00 ▼] : [00 ▼]
Type [Event Type ▼]

[Submit] [Cancel]

Details

Caption: Event Caption
Start: Event Start Date and Time
End: Event End Date and Time
Type: Event Type
Description: Event Description

COMPUTER-IMPLEMENTED SYSTEM AND METHOD FOR ELECTRONIC MEDICATION ADMINISTRATION RECORDS

BACKGROUND OF THE INVENTION

1. Field of the Invention

The present invention relates generally to the field of computer-implemented inventions, and more specifically, to a system and method for electronic medication administration records.

2. Description of the Related Art

Over the past ten years of service to long-term care ("LTC") facilities, Emissary Professional Group, LLC d/b/a Emissary Pharmacy and Infusion—a "closed door" pharmacy providing contract medication services to patients in long term care institutions around the state of Wyoming—has seen a marked increase in medication errors. In fact, medication errors have reached dangerous levels in the LTC facilities that Emissary Pharmacy serves. This market is only a very small sampling of a much larger problem, and it is not just a Wyoming problem. Medication errors in LTC facilities are a national problem and are cited in multiple studies as the number one safety issue plaguing this industry today.

According to the Journal of the American Medical Association [1], medication errors as "preventable adverse events" are a leading cause of injury and death for both the ambulatory and institutionalized elderly patients in the United States today. Medication errors are the leading cause of emergency room visits and hospitalizations, with one out of every ten skilled nursing facility residents suffering a medication-related injury every day they are institutionalized. A recent study performed by the University of Massachusetts Medical School [2] reveals that seventy three percent (73%) of the most severe injuries, including internal bleeding and death, were preventable. Annual costs for injuries due to medication errors in the LTC setting now exceed 1.5 billion dollars and may be as high as 32.8 billion dollars [3].

Patient safety and the delivery of "high-value health care" have become top priority strategic plan initiatives for the Centers for Medicare Services ("CMS") in Washington, D.C. [4]. One of the aims of high-value health care is to emphasize prevention and better support for quality care, including the improvement of medical records. Most skilled nursing facilities still depend on an antiquated system: paper-based charts and records, including the medication administration record (MAR), that are handwritten for each medication administration event for each resident receiving medications. Paper MARs are an inefficient process with no clearly defined work flow that places needless stress on nursing staff.

Paper MARs are not designed to reduce medication errors, and they have remained unchanged for decades. Illegible entries can result in medication administration mistakes; for example, a nurse might misread a handwritten note left by a doctor or colleague. Instructions about discontinuing a medication, or altering its dosage, might not be accurately recorded. If a medication pass is delayed when nursing staff are called on to meet an urgent resident need, the paper-based system makes it nearly impossible to ensure that the process resumes seamlessly from where it was discontinued when the caregiver was called away. The common practice of inserting a paperclip, bookmark, or even a drinking straw into the paper MAR during an interruption in the medication pass does not assure that it has resumed accurately.

Excluding wrong-time errors (i.e., an incident occurring as a result of medication being given outside of the time frame in which it was scheduled to be given), omission of an ordered medication is generally the most common type of drug administration error in the skilled nursing facility. According to a recent study by the Institute of Medicine [5], the most common medication administration errors include (i) omitting a prescribed medication (44.8% of total errors), (ii) administering an unauthorized medication (41.5% of total errors), (iii) administering the wrong dose (11% of total errors), and (iv) administering medication via the wrong route (2% of total errors). With so many possibilities for error, paper MARs are not sufficient to assure the accuracy of administration of any medication, especially in the LTC setting, where staffing is always an issue, and nurses are often distracted by the daily needs of the elderly population. Furthermore, the price paid for medication errors has become far too costly in both human terms and financial dollars for the practice to continue in its current form.

Accordingly, what is needed is a software program designed specifically for the LTC environment that reduces or eliminates the most common errors. Existing software programs are inadequate for the LTC environment. For one, no existing software designed to work in an acute care hospital is a complete solution for the LTC environment. In addition, the methods used to guide the healthcare provider and track medication administration lack the sophistication and flexibility to work effectively in the LTC environment. As a result, they are at best partial solutions. A further drawback to these systems is that they require an in-house server computer to archive an institution's data.

To satisfy the above needs and overcome the deficiencies of existing systems, the present invention provides a software program that visually identifies the patient, identifies the medication, and prevents the caregiver from inadvertently omitting a prescribed mediation or administering an unauthorized medication, the wrong dose, or the right medication via the wrong route. It is a further object of the present invention to provide nursing staff with an easy and efficient way to conduct daily medication passes, assuring that LTC facility residents receive the "five rights" of medication administration: right resident, right drug, right dose, right route of administration, and at the right time. Yet another object of the present invention is to provide an intuitive software program that requires no more than a few minutes of training for nursing staff to use. An additional object of the present invention is provide increased functionality at lower cost by eliminating all but absolutely necessary hardware requirements for institutions.

It is estimated that the successful deployment and use of the present invention will help LTC facilities redirect or save approximately $40,000 in annual labor costs that are currently wasted using paper-based MARs. In addition, it is estimated that more than 1,500 man hours in the average 100-bed skilled nursing facility can be redirected to patient care each year as a result of the use of the present invention. Simply stated, the present invention is designed to improve both medication pass efficiency and overall resident safety.

BRIEF SUMMARY OF THE INVENTION

The present invention is a system for electronic medication administration records comprising a cart station with a cart station database, administration web pages, and a healthcare server with a healthcare server database; wherein the cart station is located in a skilled nursing facility with patients, wherein the cart station utilizes a plan builder algorithm to build a plan for each patient based on data contained in the cart station database, and wherein the plan comprises a list of the patient's procedures for a given day and information indicating whether such procedures have been completed; wherein the cart station utilizes a plan runner algorithm to maintain and update the plan for each patient; wherein the administration web pages allow an administrator to manage utilization of the system; wherein the healthcare server is not located at the skilled nursing facility, and wherein one or more skilled nursing facilities use the system; and wherein the healthcare server and the cart station utilize a synchronization algorithm to maintain accurate and timely data for all of the skilled nursing facilities that use the system.

In a preferred embodiment, the cart station comprises a user display, and the plan runner ensures that the user display is accurate and accounts for events that occur in a given day; the plan runner ensures that no procedure is performed before its allowed time; a procedure may have one or more prerequisites, and the plan runner ensures that no procedure is performed before its prerequisites have been performed; when a procedure with a defined interval between applications of the procedure has been performed, the plan runner adds the next application of the procedure to the plan; the plan runner records when postponed procedures are due; the plan runner adds required dynamic procedures to the plan; the plan runner notifies a user of pending procedure application errors; and the plan runner records actions on procedure applications.

In a preferred embodiment, data is input into the cart station database from a pharmacy, through the administration web pages, or from the cart station itself; the cart station database comprises tables of records, each table has a timestamp that is an integer that encodes a date on which the table was last synchronized with the healthcare server, and each record has a timestamp that is an integer that encodes a date on which the record was last synchronized with the healthcare server; and the cart station ensures that each record in a table in the cart station database has been updated with data received from the healthcare server up to the date of the timestamp for that table.

In a preferred embodiment, the system undergoes a series of synchronization sequences over a period of time; the cart station sends to the healthcare server all new records, all records containing data that has been updated since the last synchronization sequence, and all records that are related to said new or updated records; the healthcare server maintains a global timestamp that is used as an official notation of time for synchronization purposes for the healthcare server and all cart stations; the healthcare server receives the records sent from the cart station; if a record received by the healthcare server is a new record, the healthcare server adds the record to the healthcare server database and ascribes a timestamp to it; if a record received by the healthcare server is an existing record, the healthcare server updates the record in the healthcare server database to match the record from the cart station and ascribes a timestamp to the updated record; the healthcare server increments the global timestamp; the healthcare server sends back to the cart station only those records comprising data that has been modified since the last synchronization sequence; each record has a globally unique ID that is used by the cart station to determine whether the record is a new record or an updated record; the cart station stores the new and/or updated records in the cart station database; and the timestamp associated with each new or updated record is updated to match the global timestamp ascribed to the record by the healthcare server. Preferably, a synchronization sequence occurs whenever the care provider logs into or out of the cart station, whenever the care provider clicks on a synchronization button on the cart station, and/or whenever the cart station is idle for a pre-defined period of time.

In a preferred embodiment, the plan builder algorithm is invoked after each login to a cart station. Optionally, the system further comprises a pharmacy server that transmits data to the healthcare server, and the data transmitted from the pharmacy server to the healthcare server is downloaded to a cart station in connection with a synchronization sequence. The cart station is preferably located on a medication cart at the skilled nursing facility.

In a preferred embodiment, the cart station generates a medication administration record report that describes all activities performed on a patient over a specified period of time. Preferably, the cart station generates an activity report that describes all activities performed on patients at the skilled nursing facility over a specified period of time. The cart station preferably generates a medical doctor report that includes prescribed medications, most recent vital signs taken, and medications given for a particular patient.

The present invention is also a method for maintaining electronic medication administration records comprising: providing a cart station with a cart station database, wherein the cart station is located in a skilled nursing facility with patients, wherein the cart station utilizes a plan builder algorithm to build a plan for each patient based on data contained in the cart station database, wherein the plan comprises a list of the patient's procedures for a given day and information indicating whether such procedures have been completed, and wherein the cart station utilizes a plan runner algorithm to maintain and update the plan for each patient; providing administration web pages that allow an administrator to manage utilization of the method; and providing a healthcare server with a healthcare database, wherein the healthcare server is not located at the skilled nursing facility, and wherein one or more skilled nursing facilities use the method; wherein the healthcare server and the cart station utilize a synchronization algorithm to maintain accurate and timely data for all of the skilled nursing facilities that use the method.

In a preferred embodiment, the cart station comprises a user display, and the plan runner ensures that the user display is accurate and accounts for events that occur in a given day; the plan runner ensures that no procedure is performed before its allowed time; a procedure may have one or more prerequisites, and the plan runner ensures that no procedure is performed before its prerequisites have been performed; when a procedure with a defined interval between applications of the procedure has been performed, the plan runner adds the next application of the procedure to the plan; the plan runner records when postponed procedures are due; the plan runner adds required dynamic procedures to the plan; the plan runner notifies a user of pending procedure application errors; and the plan runner records actions on procedure applications.

In a preferred embodiment, data is input into the cart station database from a pharmacy, through the administration web pages, or from the cart station itself; the cart station database comprises tables of records, each table has a timestamp that is an integer that encodes a date on which the table was last synchronized with the healthcare server, and each record has a timestamp that is an integer that encodes a date on which the record was last synchronized with the healthcare server; and the cart station ensures that each record in a table in the cart station database has been updated with data received from the healthcare server up to the date of the timestamp for that table.

In a preferred embodiment, the cart station database and healthcare server database undergo a series of synchronization sequences over a period of time; the cart station sends to the healthcare server all new records, all records containing data that has been updated since the last synchronization sequence, and all records that are related to said new or updated records; the healthcare server maintains a global timestamp that is used as an official notation of time for synchronization purposes for the healthcare server and all cart stations; the healthcare server receives the records sent from the cart station; if a record received by the healthcare server is a new record, the healthcare server adds the record to the healthcare server database and ascribes a timestamp to it; if a record received by the healthcare server is an existing record, the healthcare server updates the record in the healthcare server database to match the record from the cart station and ascribes a timestamp to the updated record; the healthcare server increments the global timestamp; the healthcare server sends back to the cart station only those records comprising data that has been modified since the last synchronization sequence; each record has a globally unique ID that is used by the cart station to determine whether the record is a new record or an updated record; the cart station stores the new and/or updated records in the cart station database; and the timestamp associated with each new or updated record is updated to match the global timestamp ascribed to the record by the healthcare server. Preferably, a synchronization sequence occurs whenever the care provider logs into or out of the cart station, whenever the care provider clicks on a synchronization button on the cart station, and/or whenever the cart station is idle for a pre-defined period of time.

In a preferred embodiment, the plan builder algorithm is invoked after each login to a cart station. Preferably, the present invention further comprises a pharmacy server that transmits data to the healthcare server, and the data transmitted from the pharmacy server to the healthcare server is downloaded to a cart station in connection with a synchronization sequence. The cart station is preferably located on a medication cart at the skilled nursing facility.

In a preferred embodiment, the cart station generates a medication administration record report that describes all activities performed on a patient over a specified period of time. Preferably, the cart station generates' an activity report that describes all activities performed on patients at the skilled nursing facility over a specified period of time. The cart station preferably generates a medical doctor report that includes prescribed medications, most recent vital signs taken, and medications given for a particular patient.

BRIEF DESCRIPTION OF THE DRAWINGS

FIG. 12 is a screenshot of the patient screen with a medication highlighted.
FIG. 13 is a screenshot of the patient medication profile screen.
FIG. 14 is a screenshot of the cart station's patient screen.
FIG. 16 is a screenshot of the patient screen showing patient follow-ups.
FIG. 17 is a screenshot of the patient screen showing treatments needed.
FIG. 18 is a screenshot of the patient screen showing PRNs needed.
FIG. 19 is a screenshot of the patient screen showing patient orders.
FIG. 30 is a screenshot of the patient screen showing medications administered.
FIG. 33 is a screenshot of the discontinue medication screen.
FIG. 38 is a screenshot of the new routine medication screen.
FIG. 39 is a screenshot of the new PRN screen.
FIG. 40 is a screenshot of the new treatment screen.
FIG. 41 is a screenshot of the scheduled procedure screen.
FIG. 42 is screenshot of the discontinue all medications screen.
FIG. 43 is a screenshot of the hold all medications screen.
FIG. 44 is a screenshot of the new other order screen.
FIG. 55 is a screenshot of the patient details other screen.

FIG. 69 is a screenshot of the medication frequency screen.

FIG. 70 is a screenshot of the reasons for medications not given screen.

FIG. 73 is a screenshot of the people screen with residents showing.

FIG. 75 is a screenshot of the people screen with the medication tab showing a patient's medications.

FIG. 76 is a screen shot of a calendar.

DETAILED DESCRIPTION OF INVENTION

A. Overview

The present invention is a system and method that enables healthcare providers at long-term care facilities to provide superior care to patients by providing accurate information about those patients, including what medications, treatments, and scheduled procedures need to be administered and what PRNs (medications given when necessary) are available. Innovative, new algorithms dramatically reduce the administrative overhead for institutions and individual caregivers, allowing them to use more accurate information more effectively in the care of their patients.

The system architecture of the present invention is considerably simpler than architectures of existing electronic medication administration systems, and the hardware requirements for an institution are reduced to only a single computing device. There is no need for a specialized on-site administrative computer or server, thereby reducing acquisition and maintenance costs for the institution. Another benefit to facilities is that the healthcare server offers them a single repository for recording all the procedures performed by all the caregivers at the facility. This is true even if the facility is distributed across multiple physical locations, e.g., if a facility has more than one building in the same town.

Figure 1:
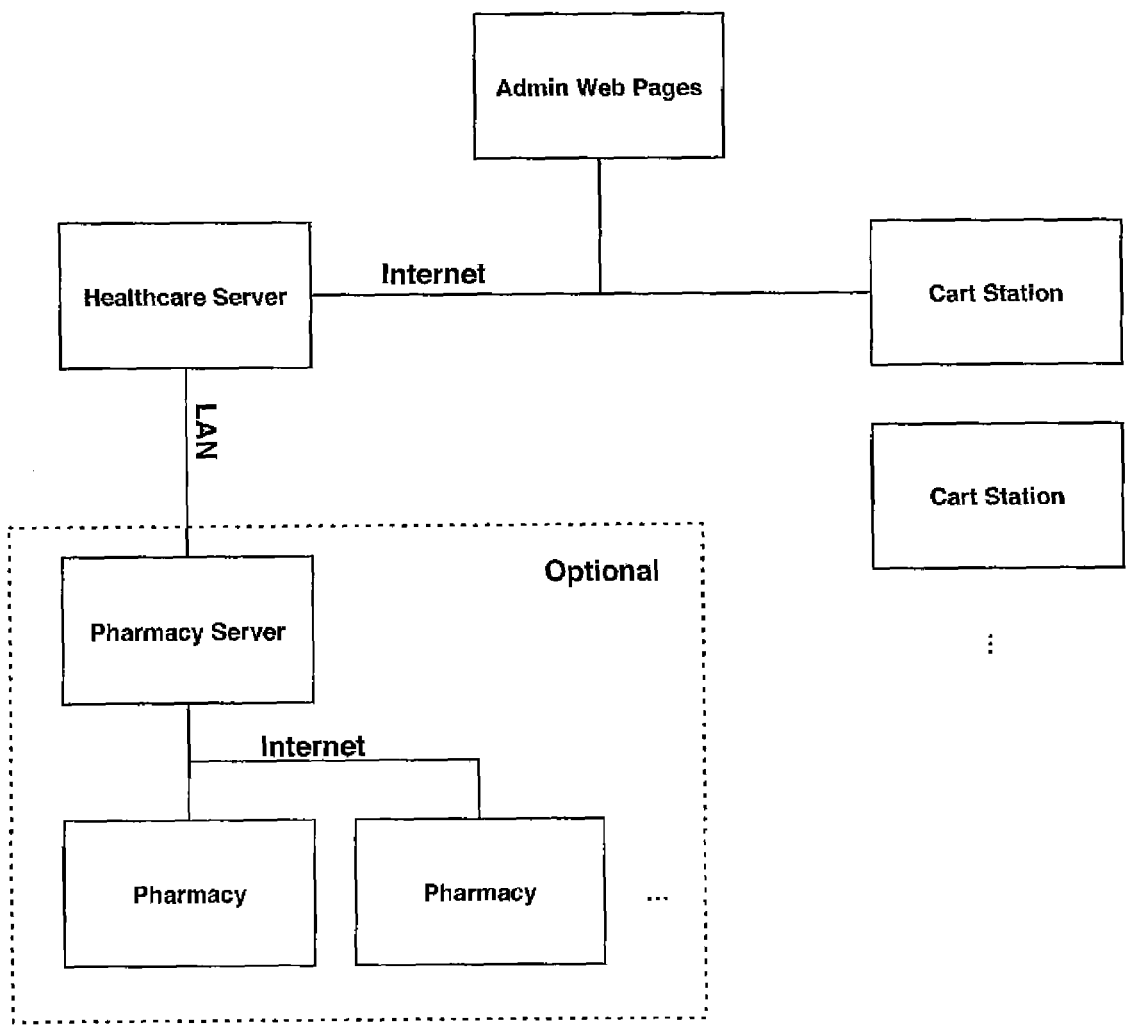
FIG. 1 is a diagram of the system architecture of the present invention.

An overview of the system architecture is shown in FIG. 1. As shown in this figure, the system of the present invention comprises a cart station that is housed in the institution's facility, the administration web pages used by the skilled nursing facility's Director of Nursing ("DON"), a healthcare server that is housed off-site and maintains accurate and current data on all institutions, and an optional pharmacy server. As used herein, the term "cart station" means the client. The cart station is housed in the institution's facility and assists the healthcare provider in her duties. The administration web pages can be accessed from any computer in the institution's facility and are used by the DON to manage utilization of the system. The healthcare server is housed off-site and maintains accurate and current data on all institutions. The healthcare server uses the Internet to communicate this data to the administration web pages and to synchronize this data with the cart station(s). The optional pharmacy server is typically housed with the healthcare server and is responsible for communication with the pharmacies used by the client institutions of the invention. If no pharmacy server is used, the system is defined as "nurse driven", meaning that all data comes from health healthcare providers at the institution.

Most of a healthcare provider's interaction with the present invention is through the cart station, a portable computing device that is assigned to the medication cart at the institution. This device runs specialized software that can construct, maintain, display, and guide the healthcare provider through an accurate plan of activities for the day for each patient associated with the cart.

An important feature of the present invention is that it maintains a full record for reporting purposes of all activities performed or not performed on patients. If a required activity is not performed, the invention ensures that a reason for non-performance is recorded or that non-performance is marked as a medication error. This information is used to dynamically build a MAR (Medication Administration Report) whenever requested. This data is uploaded to the healthcare server whenever a synchronization is performed, enabling authorized institution staff to obtain all needed reports with the click of a button. This data is also used by the cart station to properly account for the fact that some activities performed previously may affect the activities that are current or yet to come; for example, the time of the prior application of a PRN affects the next application.

The plan builder, plan runner and synchronization algorithms utilized in the present invention enable the cart station to function completely autonomously regardless of the status of its connectivity to the server. If the Internet is available, the cart station will have the latest data from the server; however, even without the Internet, the healthcare provider's routine will continue unaffected.

The healthcare server is a computer system (or can be multiple computer systems) housed in a secure off-site facility running specially-designed synchronization software. It maintains accurate and timely data in a database for all institutions that use the present invention. Periodically, the cart stations synchronize with the server (over a secure connection). This is a two-way exchange that ensures that the cart station's and healthcare server's data are the same and current.

The healthcare server also provides administration web pages that can be accessed from any computer at the institution (over a secure connection) using a web browser. This account- and password-protected interface implements the administrative function of the present invention allowing: (i) setting or changing institution data such as the institution's name, default pharmacy, and name of the DON, (ii) setting or changing institution preferences for the behavior of the cart station(s), (iii) setting or changing patient or staff data, (iv) viewing reports, (v) doctors to view patient orders, (vi) doctors to prescribe medications and orders, and (vii) scheduling of labs, scheduled procedures, assessments, etc., for patients throughout the facility.

The optional pharmacy server handles communication with the pharmacies used by the client institutions of the present invention. Whenever a pharmacy fills (changes) a prescription for a patient, this data is communicated to the pharmacy server, which places the data in the healthcare server's database. This data is downloaded to the proper cart station as a part of the next synchronization. The pharmacy server accepts data in the pharmacy standard communication protocol HL7. Most pharmacies use this protocol; therefore, it will not be necessary to purchase any new software to communicate with the present invention.

Figure 2:
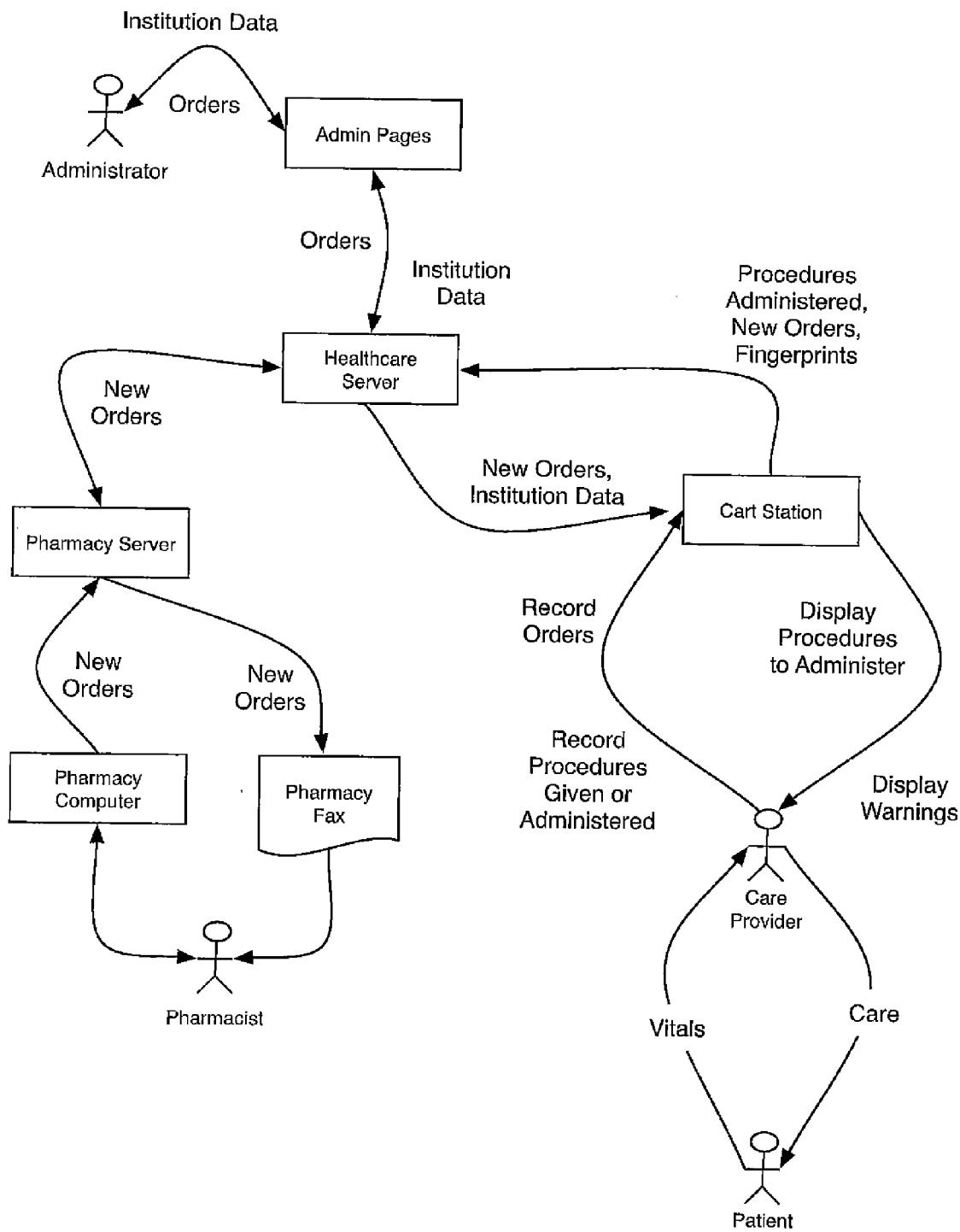
FIG. 2 is a diagram of the work flow of the present invention.

FIG. 2 is a diagram of the work flow of the present invention. The upper left-hand corner of the figure shows one way in which new orders enter the system. In this example, the DON enters a new order through the administration web pages. Such orders are uploaded to the healthcare server and incorporated into the institution's data. If appropriate, new orders are communicated to the pharmacy server, which faxes them to the relevant pharmacy. It is anticipated that direct communication of updated patient data and patient orders from the healthcare server to the pharmacy server will be supported in the future. The lower left-hand corner of the figure shows that new orders may also be entered in the pharmacy computer by a pharmacist. Such orders are communicated to the present invention's pharmacy server, which in turn communicates them to the healthcare server, where they are incorporated into the institution's data.

The arrows flowing in and out of the healthcare server box to and from the cart station box summarize the present invention's synchronization operation in which cart stations synchronize with the healthcare server. New orders and institution data are downloaded to the cart station, and records of administered procedures, new orders entered by healthcare providers through the cart station, and fingerprints are uploaded to the healthcare server and incorporated into the institution's data.

The lower right-hand corner of the figure shows the interaction between the healthcare provider and a patient, where the healthcare provider administers medications and procedures to patients and takes the patient's vitals. Above this portion of the figure, the figure depicts the interaction between the healthcare provider and the present invention's cart station. The cart station displays the currently needed (or available) medications and procedures, which the healthcare provider uses to decide what activities to undertake. The healthcare provider also uses the cart station to record medications and procedures as they are administered. In addition, the cart station displays warnings when medications or procedures are soon to be overdue so that medication errors can be avoided.

Orders newly entered on the cart station are immediately incorporated into the plan and are displayed with all other procedures but marked as temporary. When new orders are synchronized to the server, they are faxed to the pharmacy if appropriate. The pharmacy receiving the fax will create a prescription, which will be communicated back to the cart station and replace the associated temporary medication.

Regardless of whether a prescription is entered on the cart station, the administration web pages, or originates from the patient's pharmacy, the prescribed medications are initially displayed as inactive and do not cause medication errors. The first time such a medication is highlighted by scanning its barcode or selecting it with auto-complete, it becomes active. This relieves the institution from timing concerns about the delivery of new medications.

New prescriptions can also be added by a physician or called into the institution by a physician. Institution staff can then enter these through the administration web pages or the cart station. These are uploaded to the healthcare server as a part of synchronization. The healthcare server automatically sends these to the pharmacy server which faxes them to the appropriate pharmacy.

The DON of the facility using the present invention uses the functionality of the administration web pages with regard to patient and staff data to set up and maintain the institution in the system. These functions are divided into three categories: (1) configuring and maintaining the wings, rooms, and beds of the institution; (2) admitting patients, entering data about them, assigning (or reassigning) them to beds, and changing their status, entering their medications and other procedures; and (3) adding, removing, and changing data about institution staff including nurses, CNAs (Certified Nurse Assistants), and physicians.

B. The Plan

As used in the context of the present invention, the "plan" is a time-of-day-ordered list for each patient of his or her procedures for the day, including whether or not those procedures have been completed. It is an accurate, timely, and easily usable data structure containing what routine medications, treatments, scheduled procedures, and follow-ups have been completed at the present time or are due for all residents for the rest of the day and what PRNs and PRN treatments are available for the resident for the rest of the day. In other words, the plan is a plan of activities for each patient for the day. The term "model" is used herein to refer to the plan along with other in-memory data structures that are built from data retrieved from the cart station's database to enable more efficient execution of the plan runner. The cart station of the present invention uses a plan builder algorithm to construct the plan. The plan builder, described more fully below, is invoked after a login to the cart station. This means that the plan for each patient is rebuilt every time the cart station is turned on.

1. The Plan Builder

As used herein, the term "procedure" refers to any activity for a patient, including medication, PRN, prerequisite tests such as taking a patient's temperature, follow-ups such as a follow-up pain check, and treatments. A plan runner algorithm is responsible for running and maintaining the plan once the plan is built. In order for the plan to be accurate, the plan builder algorithm accounts for all completed or missed procedure applications for a specified period prior to the current time. An important property of the algorithm is that it can be executed at any time and result in a plan that can guide the plan runner to operate efficiently and accurately for the remainder of the day. This enables a plan build to be done in response to important events such a user login, a synchronization, a machine reboot or crash, a user logout, and a change of day.

The input is read from the cart station's database and consists of: (i) a list of each patient's procedure applications, i.e., each procedure and each time during the day that it is scheduled; (ii) annotations that include historical data indicating whether or not the procedure application has been performed yet on the current day; and (iii) selected data about procedures performed yesterday.

The data associated with each procedure application includes: (i) the type of procedure, i.e., routine medication, PRN, etc.; (ii) the start date; (iii) the end date, if applicable; (iv) a hold date, if applicable (this is empty unless the procedure is currently being held until a future date); (v) the frequency of application (see below); (vi) the prescribing physician; (vii) the days of the week on which the procedure should be performed; (viii) whether or not the procedure is active; (ix) the prerequisite procedures of this procedure; (x) a list of type-specific attributes (for example, a routine medication has a medication name and dose); and (x) the times of day or periods of the day when the procedure should (or may) be performed (administered in the case of a medication).

In addition, any procedure can have one or more prerequisite procedures that must be completed before the original procedure can be performed. Procedures can also have follow-ups, which are procedures added dynamically by the plan runner when the original procedure is completed. For example, PRNs have follow-up pain checks that are inserted by the plan runner after the PRN is administered.

Two other concepts central to the plan builder algorithm are "period" and "frequency." Periods are contiguous blocks of time delineated for administrative purposes by skilled nursing facilities and other facilities providing medical care. The algorithm allows a facility to define any number of periods, each of which spans any desired length of time up to 24 hours. Periods cannot span midnight. All procedures are given a frequency. Frequencies are of two types: period frequencies and QH (quaque hora) frequencies. Period frequencies specify a number of times a procedure should be performed during a day by enumerating in which periods they should be performed. For example, an institution can define BID to mean twice a day in the AM and PM periods (the periods of application of a particular BID procedure can also be defined differently for each procedure). QH frequencies specify an interval of time between applications of a procedure and have a different meaning depending on whether or not a procedure is a PRN. If the procedure is a PRN, the QH frequency specifies the minimum period of time between applications of the procedure. If it is not a PRN, the QH frequency specifies the amount of time between two required applications of the procedure within an institution-defined window. For example, an institution may define Q4H for non-PRNs to mean application of a procedure every four hours plus or minus 30 minutes.

Period frequencies may also have a multi-day interval, for example, every three days. Procedures given such frequencies will only be displayed by the cart station on the specified days. An institution may define any number of periods and any number of frequencies.

The plan runner ensures that no procedure is given before its allowed time. Procedures with period frequencies may not be given until a period in which they are scheduled has begun. Procedures with QH frequencies cannot be given before a specific time of day.

Procedure applications that are late are considered to be errors and are recorded as such in the cart station's database and on any generated reports. PRN procedures are never considered to be late. Non-PRN procedures that have a period frequency are considered to be late if they have not been completed by the end of the period in which they were due. Non-PRN procedures that have a QH frequency are considered to be late when they have not been given before the end of the institution-defined period of time after their required application time.

The plan builder algorithm provides additional flexibility in terms of the recordation of medication administrations. For example, each scheduled application of a PRN medication may have multiple tablets, and the attending healthcare provider may elect to give less than the full dose. In that case, after a follow-up pain check is performed, and after an institution-defined period of time, the remaining dose may be administered. For an institution-defined period of time after a procedure has been marked as performed, it may be undone. Medication administrations are undone, for example, when the healthcare provider discovers that a pill was spit out. A procedure application can be recorded as not given (or not done). In that case, a reason must be given by the healthcare provider, and that information is recorded. Administrations of non-PRN procedures can be postponed. If a postponed procedure application has a period frequency, the application is postponed until the next period. If it has a QH frequency, it is postponed for the frequency interval. A procedure application can be postponed only once. All of these events are recorded by the plan runner.

A preferred embodiment of the plan builder algorithm is set forth below. Note that the attributes of a procedure are referred to in this algorithm with dot (".") notation; for example, if a procedure is referred to as p, the time a procedure is scheduled to be performed is referred to as p.time, and the frequency of a procedure is referred to as p.frequency:

```
retrieve the patients of this machine as patients
retrieve the procedures indexed by patient as procedures
retrieve the scheduledTimes of each procedure with today's
           applications of the procedure (if it has been applied)
as scheduledTime ordered by time
retrieve each (last application of a PRN yesterday) indexed by patient
           as yesterdayPRNs
for each patient do
    for each procedure as p in yesterdayPRNs[patient]
        if (p.completed && !p.followup.completed &&
                today(p.followup.time)
            plan[patient].add(p)
        if (p.completed && p.numTabsGiven < p.numTabsTotal &&
                today(p.time + multitab_interval))
            insertMissingMultitab(p)
    for each procedure as p of patient do
        if (now > p.enddate || now < p.startdate ||
                now < p.holddate) continue // do not add to plan
        // The following procedure should not be performed today
        if (dayOfWeek(now) & p.weekMask == 0 ||
            !multiday(p.multidayFrequency,p.startDate,today))
            continue
    for each scheduledTime(p) as s do
        if ([p,s] has been applied && [p,s] is not marked undone)
            if (application marked not given) [p,s].notGiven = true
            else [p,s].notGiven = false
            [p,s].time = s.actual_time
            if (![p,s].notGiven) [p,s].completed = true
        else
            if (qhFreq(p.frequency))
                [p,s].time = s.scheduled_time
            else [p,s].time = startOfPeriod(s.scheduled_time)
            [p,s].completed = false
        addPrereqs([p,s])
        if (p is a PRN)
            if (![p,s].completed) {
                if ([p,s] is first application today)
                    yProc = getProcedure(yesterdayPRNs[patient],p)
                    if (yProc && p.time – yProc.time <
                            interval(p.frequency))
                        [p,s].time = yProc.time + interval(p.frequency)
                    else [p,s].time = "As needed"
                else if (previousApplication([p,s]).completed)
                    fixupPRNTime([p,s],previousApplication([p,s]))
                else continue // do not add to the plan
            } else
                    if ([p,s].numTabsGiven < [p,s].numTabsTotal &&
                        now – [p,s].time < multitab_interval)
                        insertMissingMultitab([p,s])
                    if (![p,s].followup) addMissingFollowup([p,s])
        else if ([p,s].postponed)
            [p,s].time = advancePostponed([p,s])
            [p,s].postponed = [p,s].time < now
        if (qhFreq(p.frequency)) setEndTime([p,s])
        plan[patient].add([p,s])
        checkMedError([p,s])
if (firstRunToday( )) markYesterdayMedErrors( )
```

The procedures utilized in the plan builder algorithm are described below:

multiday(nunberOfDays,startDate,today) determines, for a procedure that is only supposed to be given every so many days, whether it should be given today. It does this by performing modular arithmetic based on the days between applications and the number of days today is from the procedure's startDate. If the procedure should be performed today, true is returned. Otherwise, false is returned.

insertMissingMultitab(p) inserts a PRN into the model that is scheduled for multitab_interval after p.time and contains the rest of the tablets not given in p. Also a pain prerequisite is inserted for the new PRN.

getProcedure(list,p) returns a procedure from argument variable list that is the same as the procedure p (i.e., has the same procedure identifier).

fixupPRNTime(p,previousP) sets p.time to be previousP.time+interval(p.frequency).

advancePostponed(p) sets p.time to be properly incremented depending on the type of p.frequency.

checkMedError(p) checks whether p is overdue, and if so, marks it as a medication error and records it as "Not given: medication error" in the database.

markYesterdayMedErrors( ) finds any procedures that were not given as required yesterday and marks them as "Not given: medication error".

addPrereqs([p,s]) adds the prerequisite procedures (if any) to the procedure application [p,s]. The prerequisite procedures are also procedure applications, and they have been retrieved from the cart station's database with all of the patient's procedure applications.

qhFreq(frequency_name) returns true if frequency name is the name of a QH frequency.

startOfPeriod(period_name) returns the time of the start of period period_name.

previousApplication([p,s]) locates and returns the previous application today of p (if any) in the plan.

The properties discussed below (in this paragraph) are true of the plan once it is built using the plan builder algorithm and are maintained at all times by the plan runner. All procedure applications required yesterday are recorded as completed or not given. All past due procedures are marked as "Not given: medication error." No procedure can be marked completed before its allowed time. All procedure applications recorded as "Not given" are marked as such, and their time is the time at which they were recorded as not given. All completed procedure applications are in the plan and marked as completed, and their time is the actual time of completion. All incomplete procedures are marked as such, and their time is the time at which they are required to be given if they are not PRNs and the earliest time at which they may be given if they are PRNs. If the first application for the day of a PRN has not been given, it is marked "As needed" unless the time of the last application yesterday requires the time of the first application to be set, in which case it is set to the appropriate earliest time. There is at most one incomplete occurrence of every PRN. All completed PRNs have pain follow-ups. All completed meds have all of their prerequisites completed.

2. The Plan Runner

The plan runner is the continuously running main loop of the cart station. After each rebuild of the plan, it has the properties described in the preceding paragraph. The plan runner is responsible for guaranteeing that these properties are maintained at all times during the execution of the system and also for: (i) ensuring that the user display is always accurate and accounts for all events that have occurred thus far today; (ii) ensuring that no procedure is performed before its allowed time; (iii) ensuring that no procedure is performed before its prerequisites are performed; (iv) adding the next application of a QH procedure to the plan when a QH application is completed; (v) recording that postponed procedures are once again due; (vi) adding any required dynamic procedures (such as follow-ups or subsequent tablets of a multi-tablet PRN) into the plan; (vii) notifying the user of pending procedure application errors; and (viii) recording all actions on all procedure applications. Because of its interaction with the user, the plan runner is an event-driven algorithm.

Figure 4:
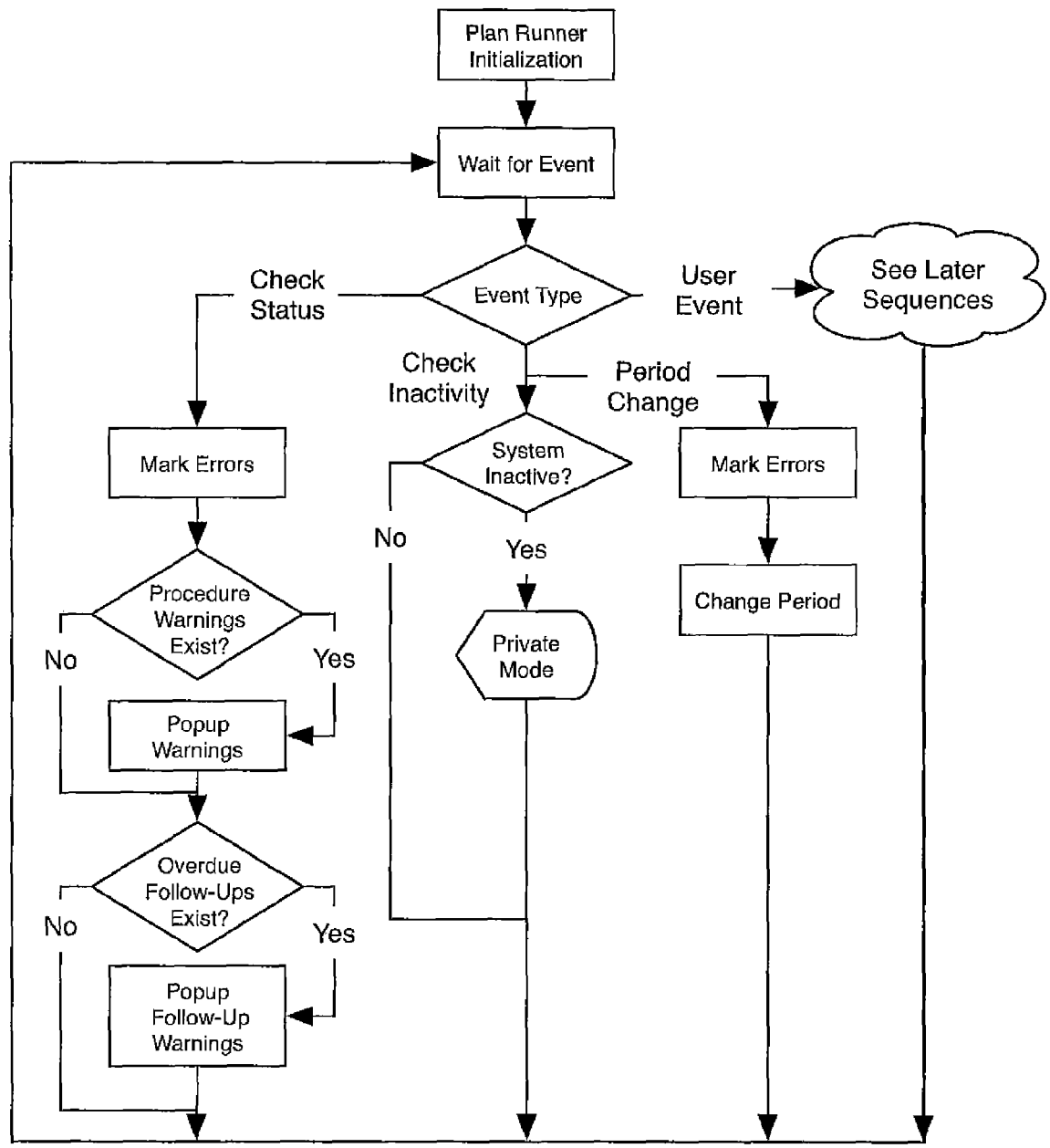
FIG. 4 is a diagram of the flow of the plan runner.

The flow of the plan runner is depicted in FIG. 4. After the plan has been built, the plan runner initializes by setting a period change timer event for the time of the next period, setting a check status timer event for every minute and an inactivity timer for an institution-defined period of time, and then displaying the appropriate main screen of the application depending on the class of user logged in.

As shown in the figure, the plan runner then enters a wait state waiting for an event to occur. Whenever there is a user-generated event (such as the user clicking on a button or an icon on the display), the plan runner's response depends on the event and on which screen is currently displayed.

The period change timer is set to run at the end of the current period. When it does, it records any errors and then changes the period by setting the period start time and end time appropriately. The errors that are recorded are: (i) any procedures with period frequency that were due but not completed in the period; (ii) any procedures with QH frequencies that are more than an institution-defined window overdue; (iii) any prerequisites of procedures from (i) or (ii) that were not completed; and (iv) any follow-ups that are overdue more than an institution-defined window. In addition, any postponed procedures that have become due are moved to the appropriate due screen.

The check status timer is set to issue a check status event every minute. When this procedure executes, it performs steps (ii) through (iv) above and also checks for postponed procedures. Then it checks if any procedures currently not completed with QH frequencies are within an institution-defined warning time of their end times or whether the time of day is within an institution-defined window of the end of a period and there are period procedures that have not been completed. If so, it pops up a warning screen listing the patients with procedures in this state. If not, the system checks whether there are any overdue follow-ups and, if so, pops up an animated warning with sound.

A separate timer is used to check whether the cart station has been inactive for at least an institution-defined period of time. If so, the cart station is placed in private mode to protect against unauthorized access. This event is handled separately so that the cart station enters private mode regardless of what screen it is displaying.

C. The Cart Station

The cart station displays all the procedures currently or soon to be due (or available) for each patient and, for each of the procedures that is due, enables the healthcare provider to mark these procedures as completed or not given as the healthcare provider performs them (or elects not to perform them). An institution may have as little as one cart station or, for larger institutions, several cart stations.

In addition to recording the procedures performed (or not performed), the cart station enables the healthcare provider to (i) postpone for a short time applications of routine medication and treatments, (ii) hold applications until a future date, (iii) discontinue routine medications, PRNs, or treatments, (iv) record that narcotics have been destroyed, (v) replace care-provider entered medications, (vi) create nurse notes, and (vii) view patient schedule(s). The cart station also gives the healthcare provider easy access to the following information about each patient: basic information (such as name, age and weight), the patient's full medication profile, most recently recorded vital signs, dynamically generated charts of historical vitals data, nurse notes and orders, attending physician contact information, patient directives, insurance and contact information, allergies, pharmacy preferences, and dietary restrictions.

Almost all long-term care facilities divide the day into periods, and this concept is deeply integrated into the present invention. The current period is displayed on most screens of the cart station. As explained above, the present invention allows for two different types of frequencies: period and repeating (or "QH"). Activities with period frequencies should (may) be completed in certain periods. Activities that have QH frequencies should (may) be completed on an interval basis (e.g., every four hours).

Medications can have prerequisites that are displayed by the cart station, which does not allow a healthcare provider to record a medication as given before it is due or before its prerequisites are completed. If the healthcare provider attempts to record a medication as given for which a prerequisite has not been marked as completed, an alert is displayed, and the attempt to record the administration fails. Medications and PRNs can also have follow-up procedures; for example, PRNs always have pain check follow-ups, requiring the healthcare provider to check a patient's pain level a specified period of time after administering the PRN.

In addition to displaying the follow-ups for each patient, the cart station reminds the caregiver when follow-ups are overdue by means of a popup display of an animation with sound. The cart station will also display popup reminders about soon to be overdue medications, treatments, and procedures. The institution can configure when these popups occur. Simple and intuitive interfaces are provided, enabling the healthcare provider to enter the results of prerequisites and scheduled procedures, like vital sign checks and where on a patient's body a shot was administered.

The cart station also enables the healthcare provider to enter new prescriptions, treatments, and scheduled procedures when necessary. Icons are provided in strategic locations for access to this functionality. Most institutions maintain an ER (Emergency Requisition) box that contains medications for emergencies. Healthcare providers can enter new medications from the ER box or that are obtained from a local pharmacy. If the ER box is selected, the cart station displays the contents of the medications in the ER box and enables the healthcare provider to choose from those medications. Otherwise, the healthcare provider must type in the name of the medication. In either case, additional information must be entered about the order, such as dose and frequency of administration (for more detail, see FIG. 38).

The healthcare provider can also obtain reports directly from the cart station. The current types of reports are: MAR, activity report, and MD (Medical Doctor) report. The details of these reports are discussed more fully below.

The present invention has a number of preferences that can be set for an institution to customize the behavior of their cart station(s). Some of these preferences are the contents of the institution's ER Box, the definitions of periods for the institution (e.g., AM is from 8:00 to 10:00 a.m.), the time before the end of a period at which warnings are popped up, and whether fingerprint scans are required to gain access to the cart station(s) or whether providing only a PIN (Personal Identification Number) is required. There are a number of other preferences, allowing the institution great latitude in specifying the behavior of their cart station(s) (a full list of preferences is given in Section F, Administration Web Pages).

For security and privacy reasons, login access to the cart station is protected by a PIN and optionally also by a fingerprint scan. The cart station login sequence is an example of how online/offline support permeates the present invention. When a user tries to log in, the cart station attempts to perform a synchronization with the healthcare server to ensure that the cart station has an up-to-date list of valid users; however, if the server is not available, the cart station will still allow the user to log in, based on its database of valid users.

Figure 3:
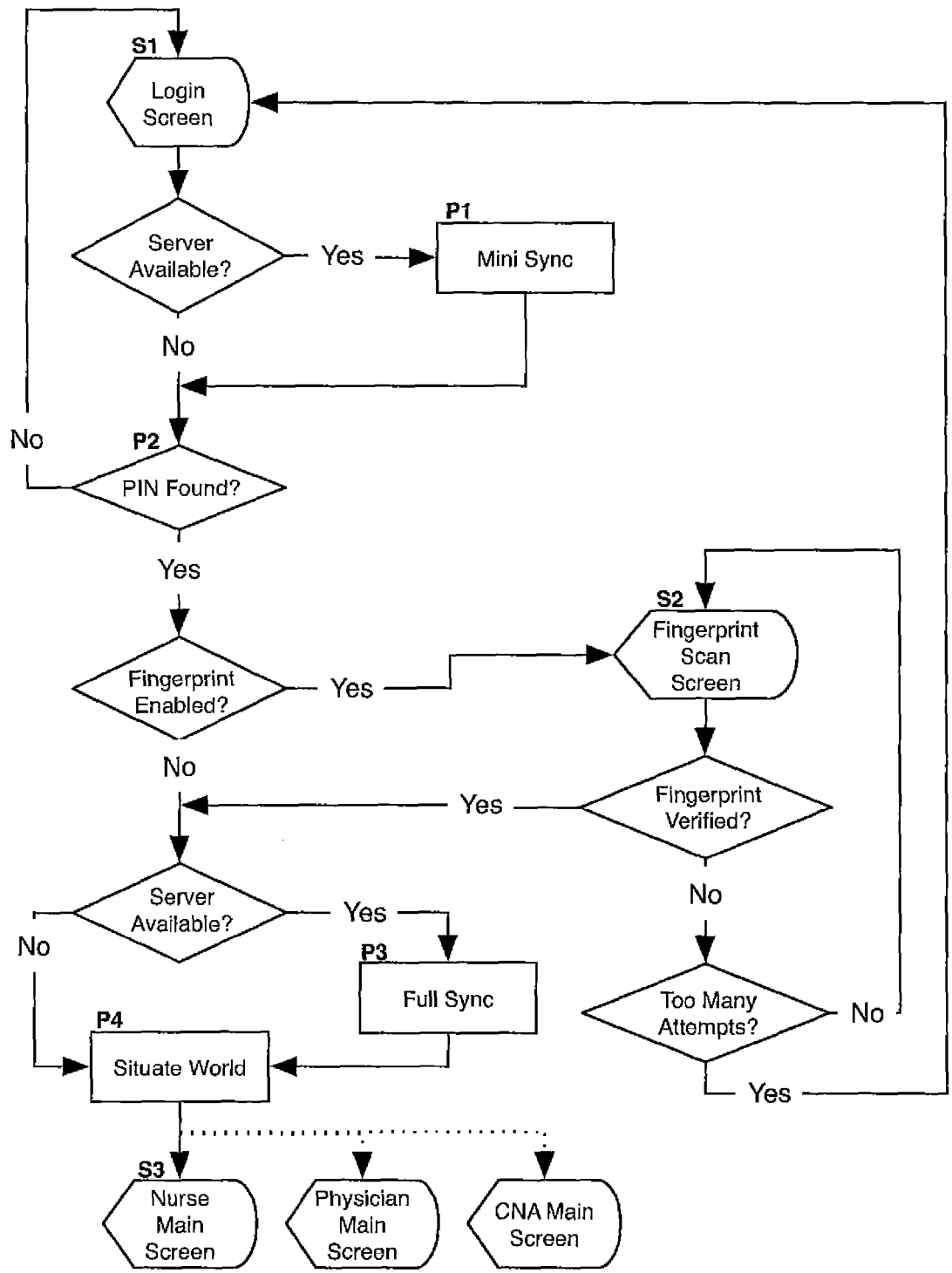
FIG. 3 is a diagram of the flow of the cart station login sequence.

FIG. 3 describes the flow of the cart station login sequence. In step S1, when a login is attempted, the user enters his or her PIN. In step P1, if the server is available, a mini synchronization operation is performed in which only institution preferences and new staff data is retrieved from the server. (For a more detailed description of the synchronization algorithm, see Section E below.)

In step P2, the supplied PIN is looked up the in cart station's database. If not found, the process returns to step S1. If found, the institution preference is checked to determine if a fingerprint scan is required. If so, the process proceeds to step S2; otherwise, it proceeds to step P3.

At step S2, based on the PIN entered, the user's fingerprint file is accessed. The user scans his or her fingerprint. At this point, one of three things can happen. One possible result is that the scan fails and the user is required to swipe again. A second possible result is that the scan succeeds, is compared to the fingerprint file and is verified. A third possible result is that the verification fails. In the first case, step S2 is repeated. In the second case, the process proceeds to step P3. In the third case, the process proceeds to step S1.

At step P3, if the server is available, a full synchronization operation is performed where any new data is exchanged between the cart station and the server. At step P4, a plan build is performed. As described in Section 1 above, all activities that have been performed thus far today are retrieved and used to determine what the current state of each patient is based on the time of day. For example, patient X has a routine medication that is to be administered BID during the AM and PM periods. It is currently the PM period, and this medication was administered as required in the AM period. Hence, patient X should receive this drug in the current period.

At step S3, the cart station has main screens tailored to the permissions given to and the class of the user logged in. Currently, there are three main screens: the nurse main screen, the doctor main screen, and the CNA (Certified Nurse Assistant) main screen. Other main screens (such as a pharmacist screen) may be included as needed. Depending on the permissions associated with the user and the class of user, the appropriate main screen is entered.

Another algorithm installed on the cart station is the new user credentials algorithm. This enables new user's fingerprints to be scanned in and automatically uploaded to the healthcare server and distributed to the other cart stations of an institution. By virtue of new user algorithm, a new employee can scan his or her fingerprint on a single cart station, enabling him or her to login to this station. The next time a synchronization is performed, the fingerprint is uploaded to the healtheare server. As other institution cart stations synchronize, they receive the new fingerprint, enabling the new employee to login to these other stations. On the other hand, if the Internet is not available, the employee performs a fingerprint acquisition on multiple stations, enabling him or her to login on those stations. Hence, whether or not the Internet is available, a new employee can login to multiple stations, and if the Internet is available, only a single acquisition is required for the employee to have access to all the cart stations at a facility.

Figure 7:
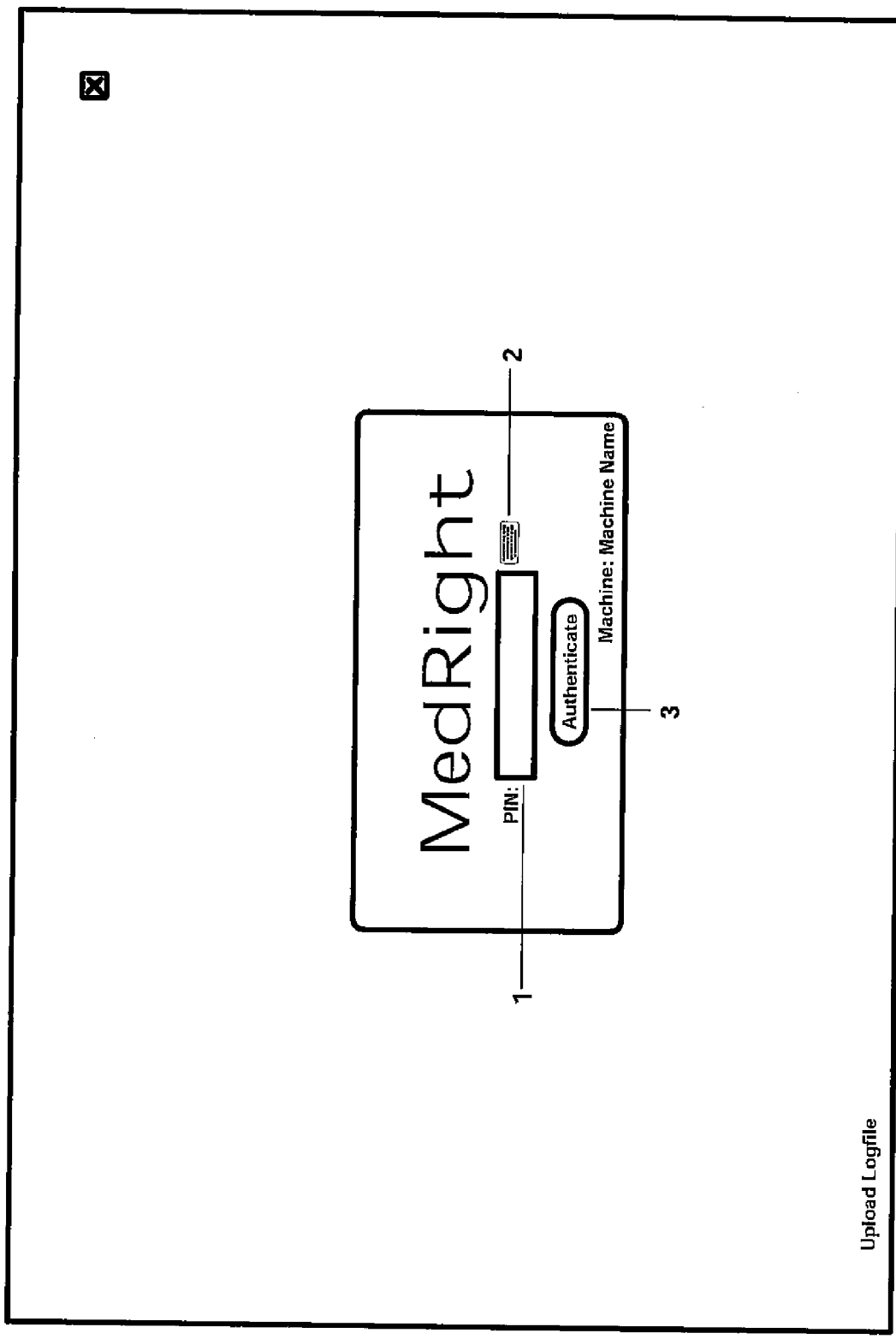
FIG. 7 is a screenshot of the cart station login screen without fingerprint authentication.
Figure 8:
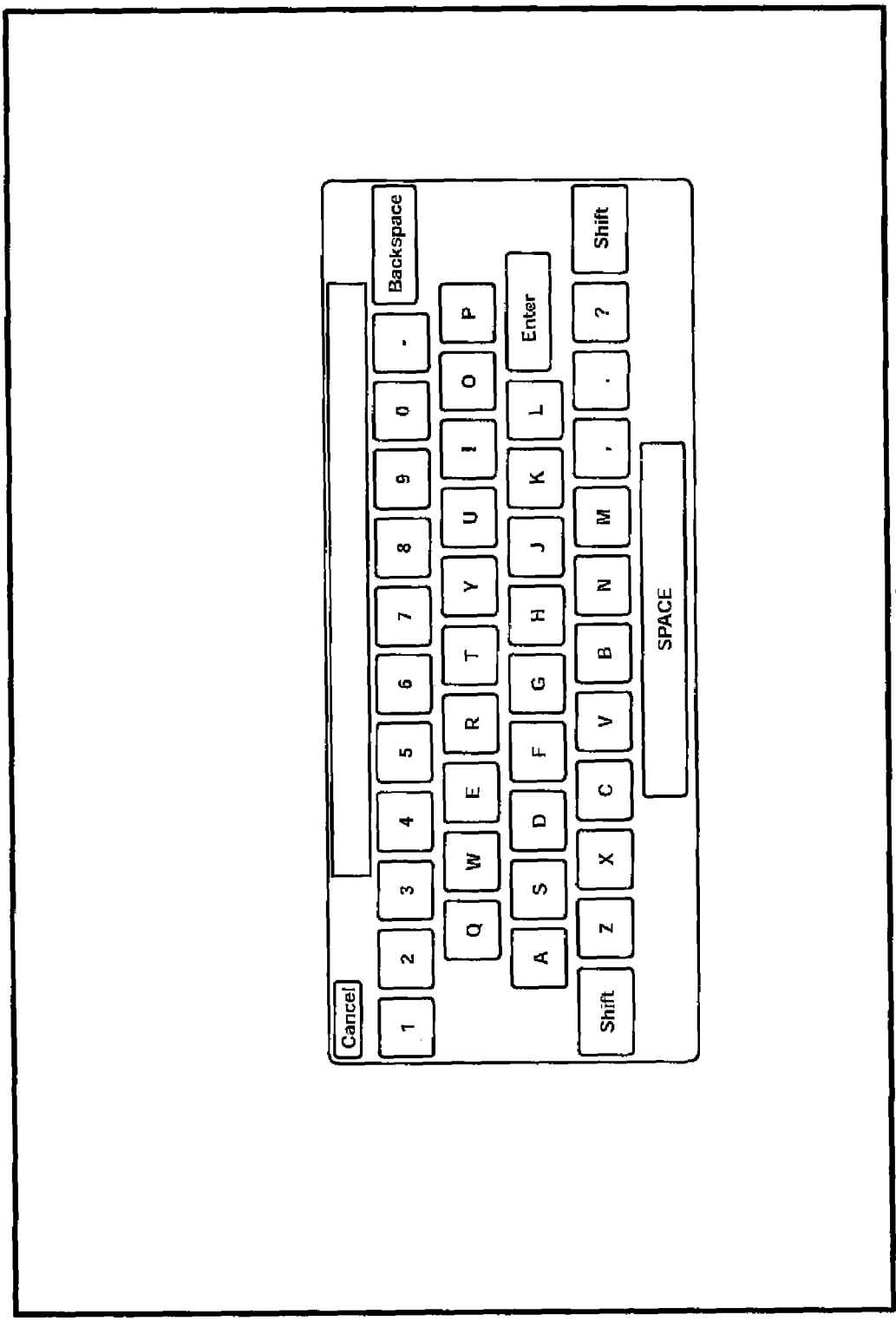
FIG. 8 is a screenshot of the on-screen keyboard.
Figure 9:
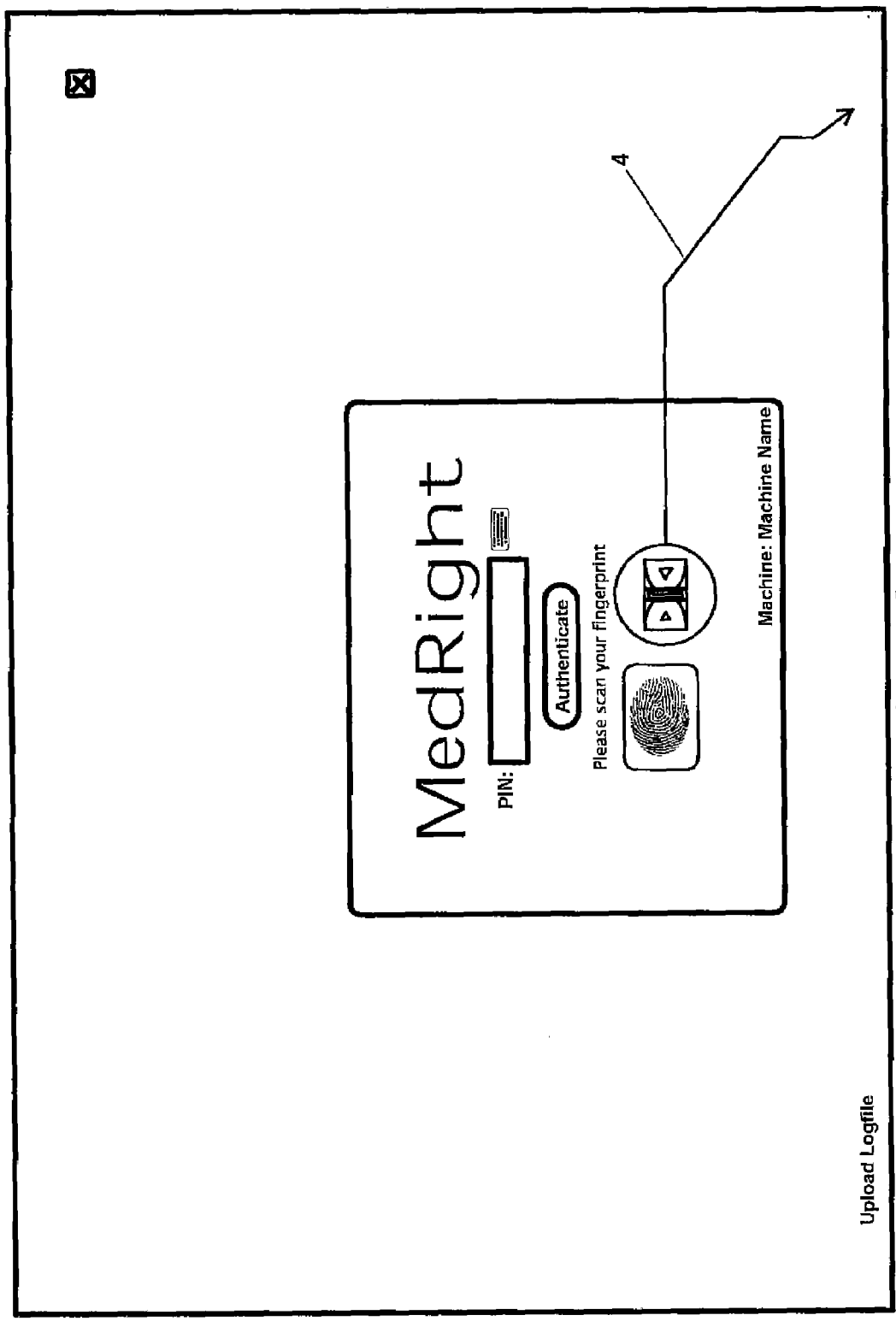
FIG. 9 is a screenshot of the cart station login screen with fingerprint authentication.

The healthcare provider's interaction with the cart station begins on the login screen shown in FIG. 7. The user types his or her PIN into the text box 1 and clicks the authenticate button 3, beginning the cart station login sequence. Should the cart station computing device not include a keyboard, the user clicks the keyboard icon 2, and a special on-screen keyboard is displayed (FIG. 8) enabling the PIN to be entered on the touch screen. The on-screen keyboard is accessible through the same icon appearing on all screens of the application that require text input. If a fingerprint scan is required for authentication, the screen shown in FIG. 9 is displayed. The arrow 4 indicates the location of the fingerprint scanner.

Figure 10:
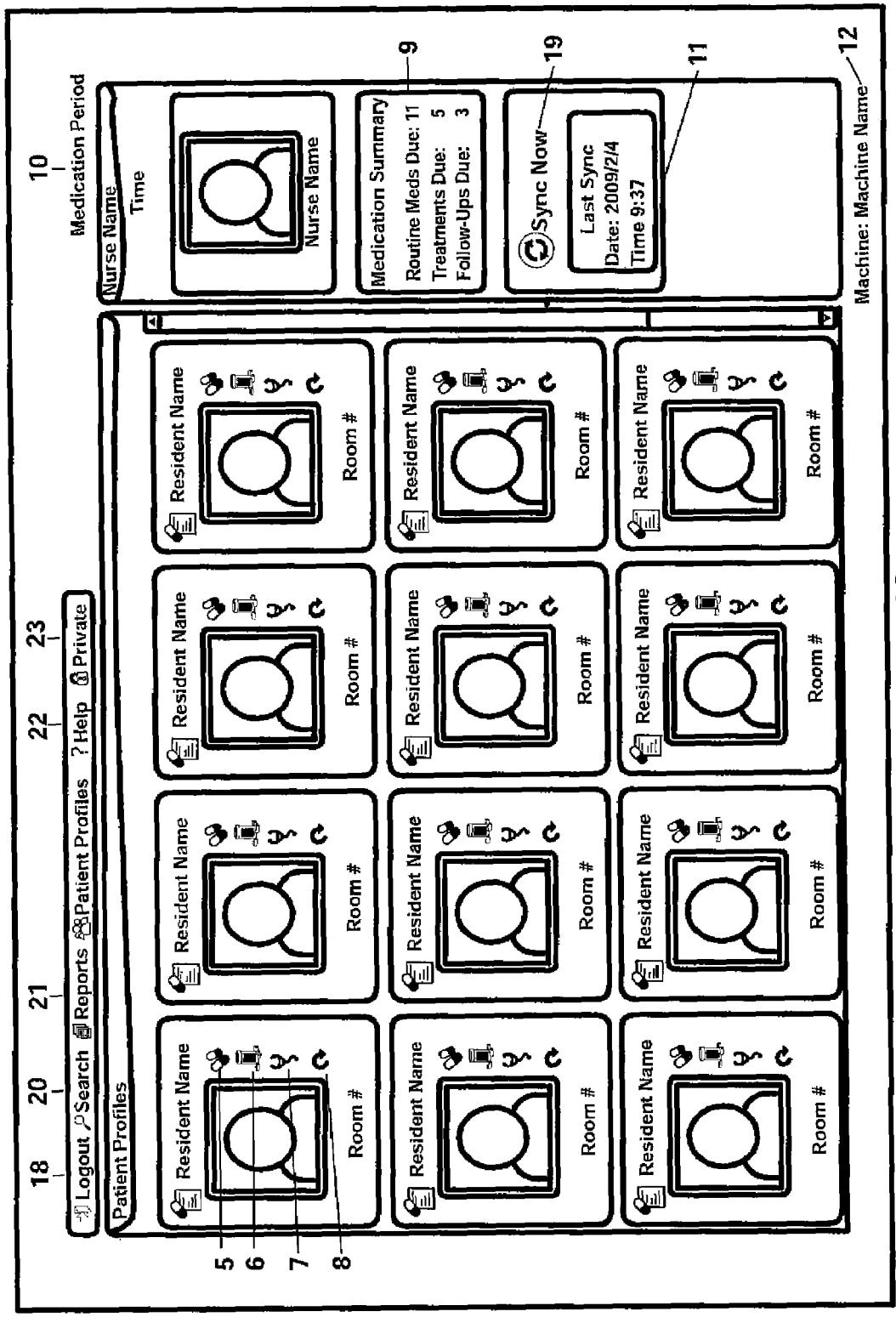
FIG. 10 is a screenshot of the nurse main screen.

FIG. 10 shows the main screen of the cart station. This screen displays all of the patients assigned to the cart, along with an indication of what types of procedures (if any) they have due, i.e., routine medications 5, PRNs 6, treatments 7, and follow-ups 8.

In a preferred embodiment, colorful and intuitive icons are used to enable the healthcare provider to quickly assess the needs of each patient and to navigate to a more focused view of a patient. The main screen also displays a medication summary (9) enabling the healthcare provider to assess the current work load, the current medication period (10), last synchronization time (11), and the name of the cart station machine (12). There are a number of functions that can be initiated from this screen by clicking various buttons and icons. These functions are summarized in FIG. 11.

Figure 12:
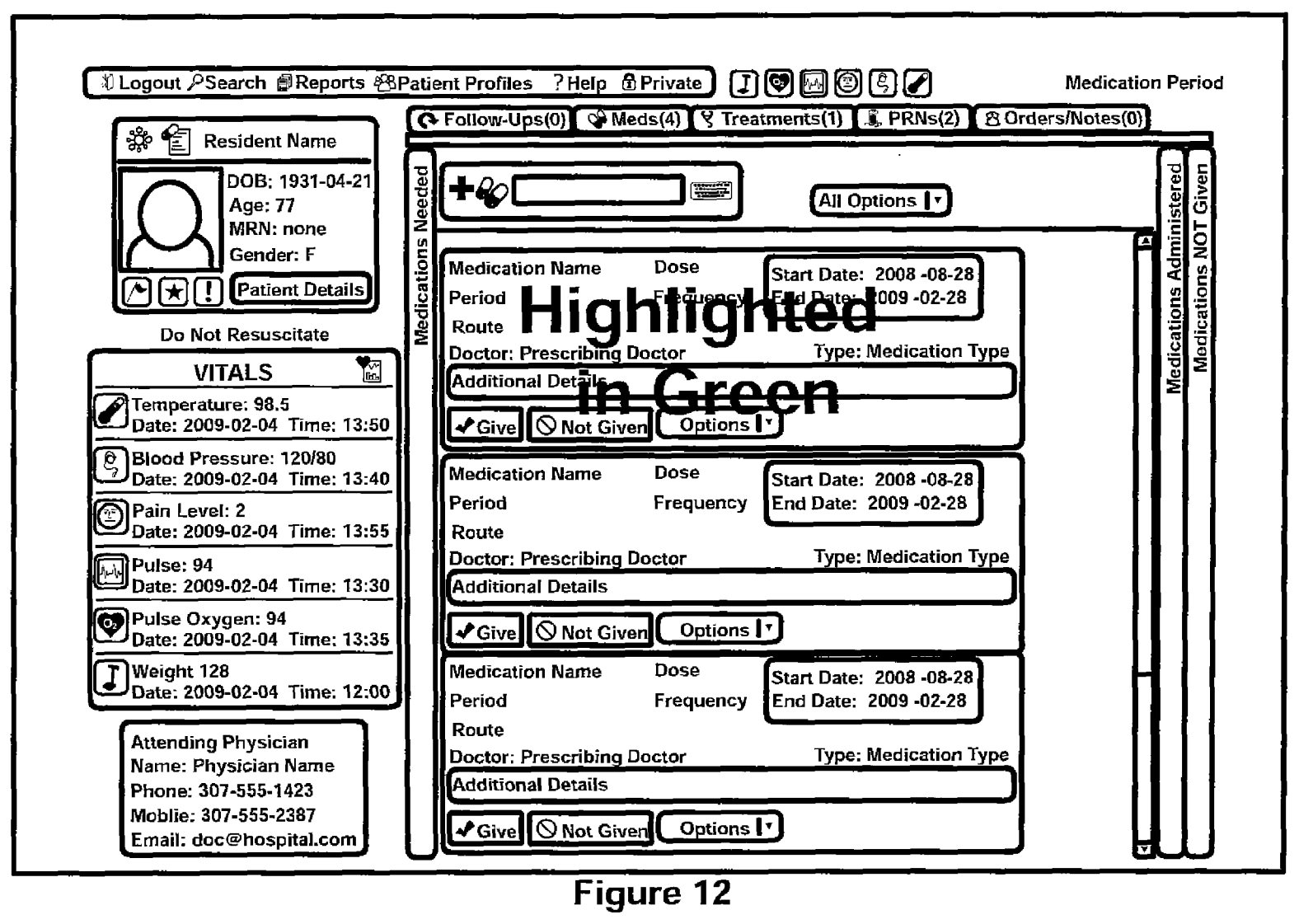

The healthcare provider can use an optional handheld barcode scanner to highlight and then record as administered medications needed or PRNs available (see FIG. 12). For institutions that are nurse-driven or cannot use a barcode scanner, there is convenient auto-completing functionality for highlighting medications. The auto-completer enables the healthcare provider to begin typing in the name or RX number of a needed medication. As characters are typed, a pulldown menu is shown with only the medications whose names (or RX numbers) start with the typed characters. A selection can be made from this pulldown menu at any time.

Figure 11:
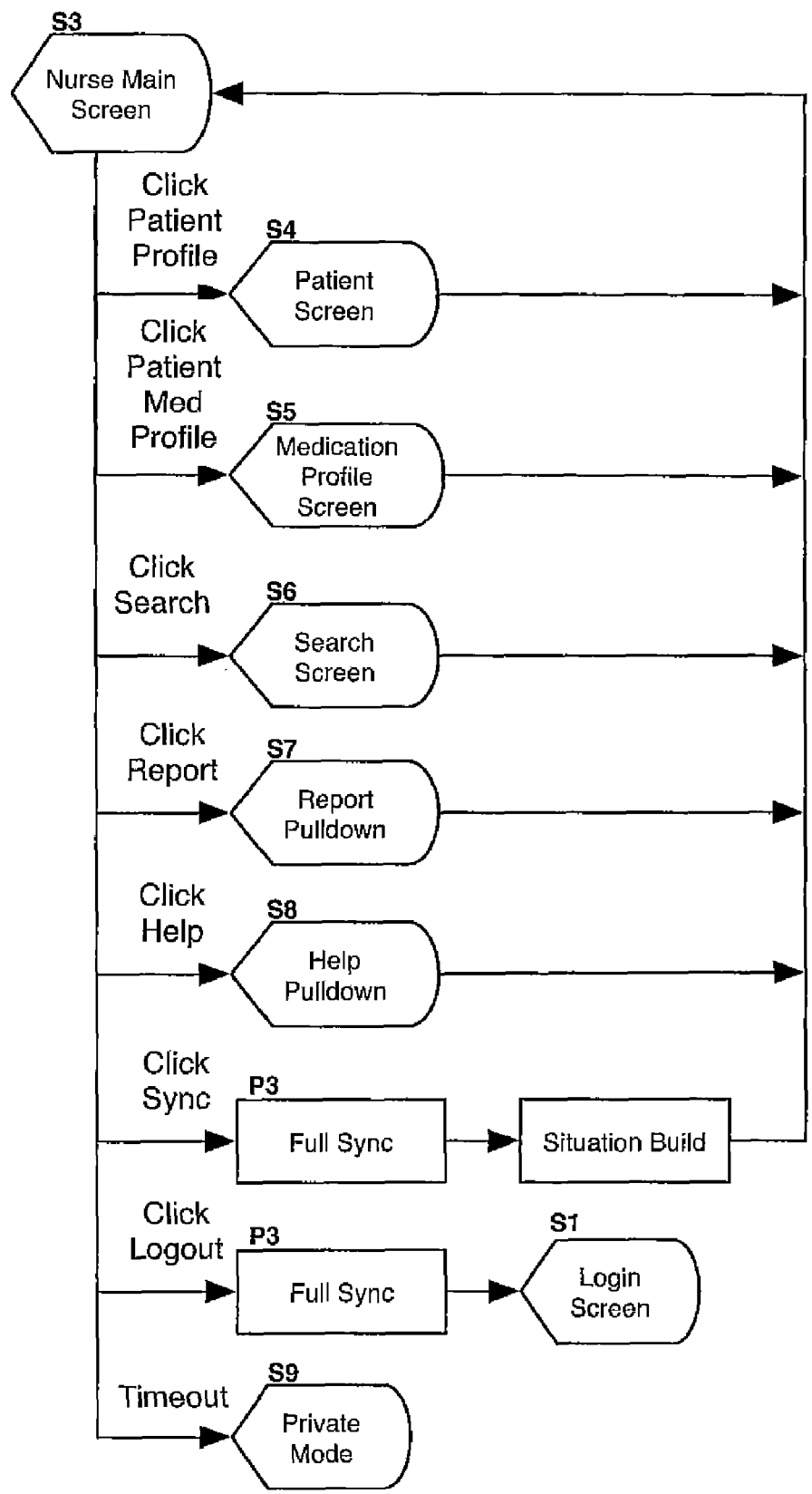
FIG. 11 is a diagram of the flow of the nurse main screen.

Referring to FIG. 11, at step S4, if a patient's picture is clicked, the patient screen is displayed. The patient screen is where more detail can be obtained about individual patients and where activities due for those patients, such as administering a routine medication, can be recorded.

At step S5, if a patient's medication profile icon (36 on FIG. 14) is clicked, the medication profile screen (see FIG. 13) is displayed. The medication profile is a convenient display of a patient's medications 13, PRNs 14, treatments 15, and scheduled procedures 16. The patient's current insulin sliding scale is also shown on FIG. 13 (reference number 17).

Figure 47:
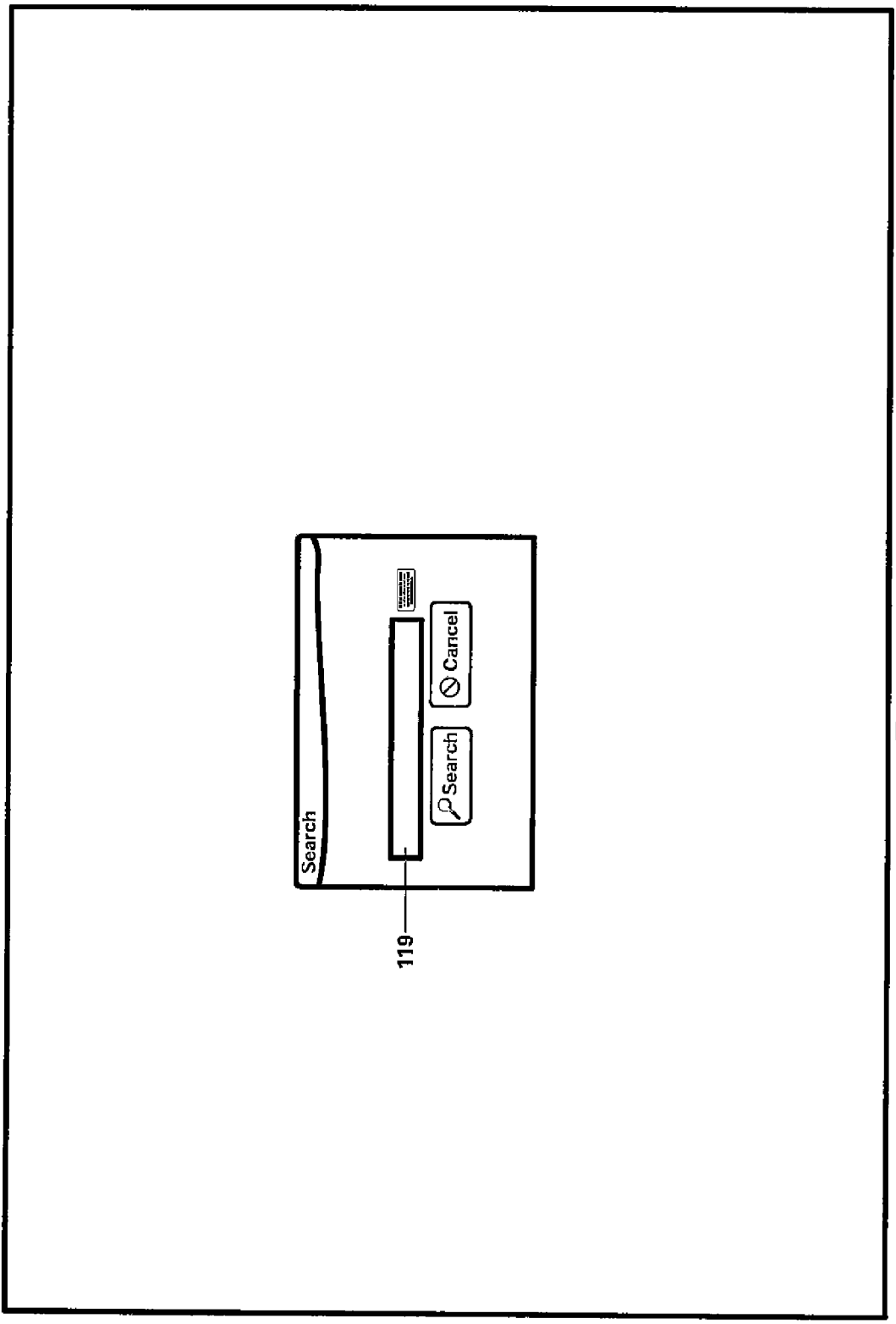
FIG. 47 is a screenshot of the search screen.
Figure 77:
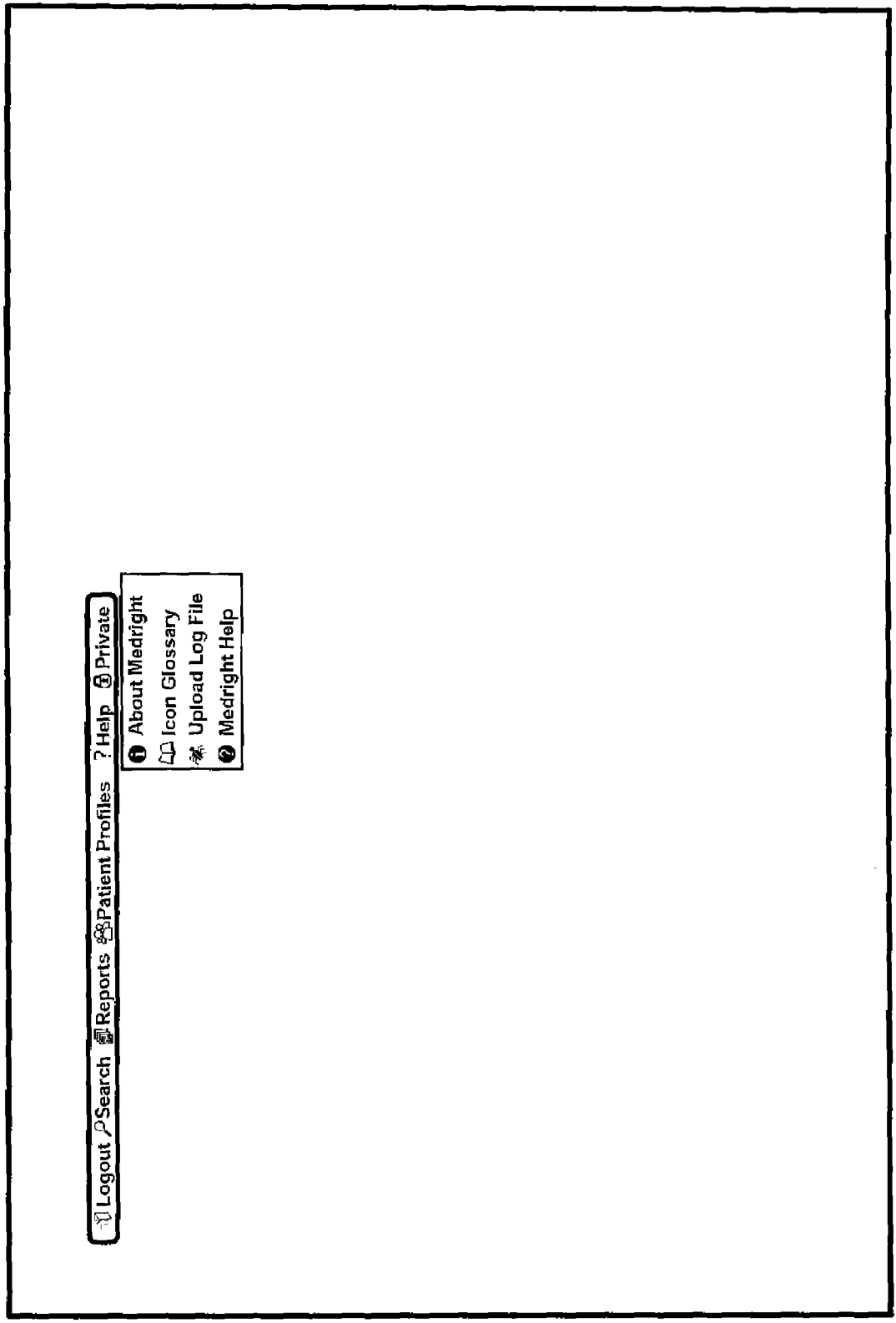
FIG. 77 is a screen shot of the help pulldown menu.

Referring back to FIG. 10, if the logout button 18 is clicked, a full synchronization is performed and the login screen (see FIG. 7) is displayed. If the sync now icon (19 on FIG. 10) is clicked, a full synchronization is performed, and a plan build is performed. If the search button 20 is clicked, the search screen (FIG. 47) is displayed. If the reports button 21 is clicked, the report pulldown menu is displayed (FIG. 49). If the help button 22 is clicked, the help pulldown menu is displayed (FIG. 77). If the private mode button 23 is clicked, the private mode screen is displayed (see FIG. 48).

Figure 14:
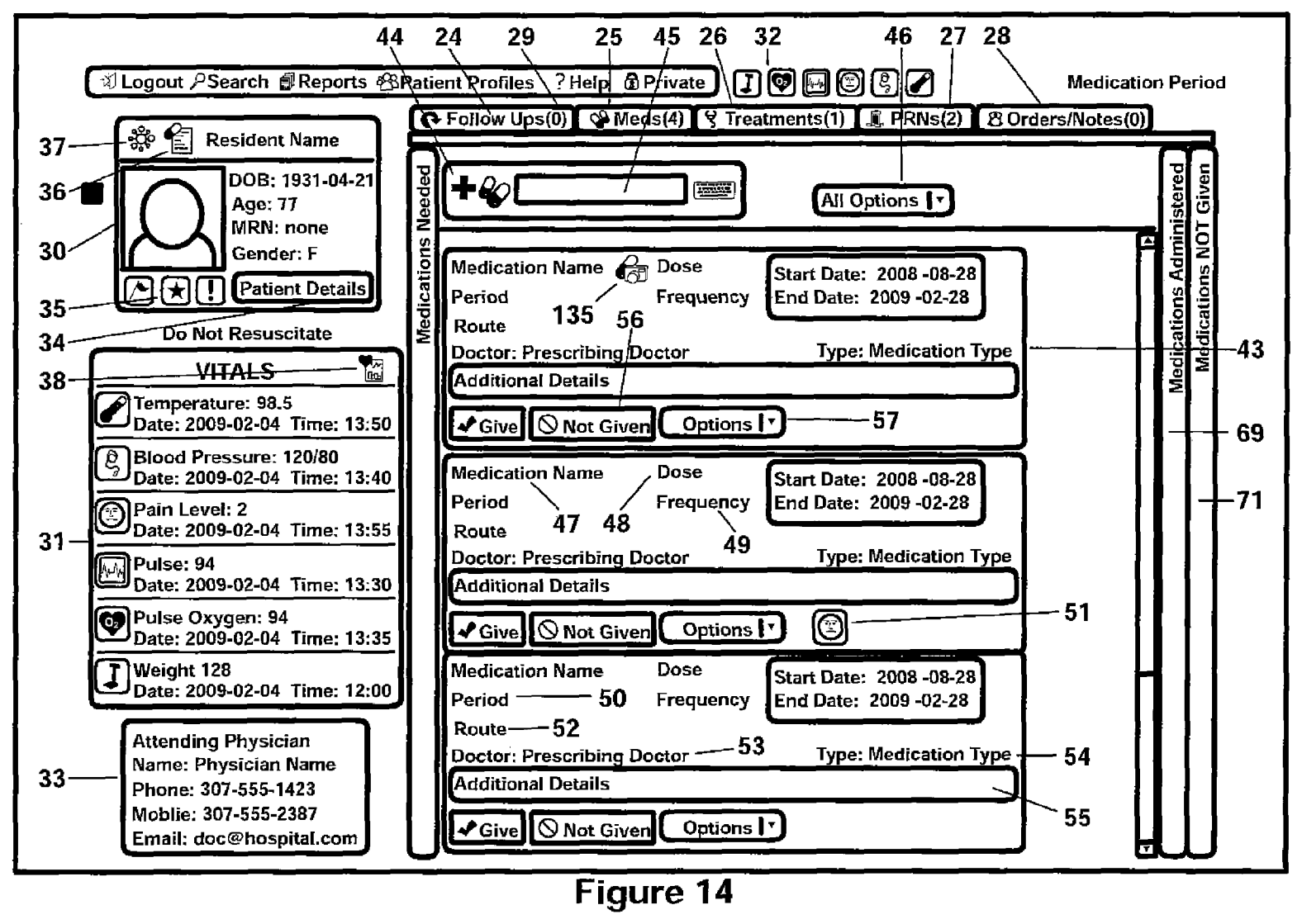
Figure 15:
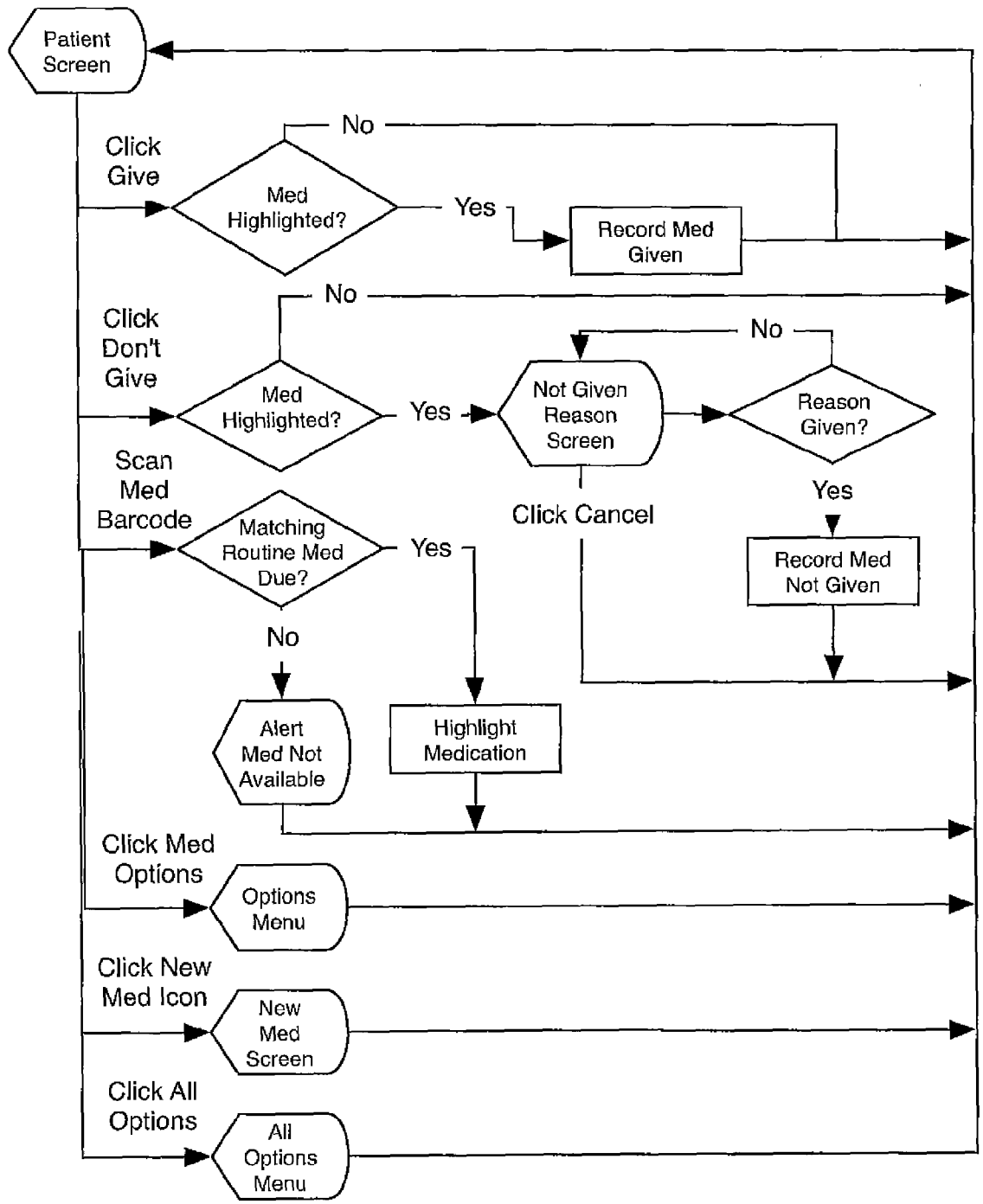
FIG. 15 is a diagram of the flow of the patient screen.

FIG. 14 shows an example of the cart station's patient screen. When this screen is first entered after clicking on a patient's picture on the nurse main screen (FIG. 11), the configuration depends on the current situation for the patient being displayed. The nurse can switch between these different screens (FIGS. 16, 17, 18 and 19) by clicking on the tabs labeled follow-ups 24, routine meds 25, treatments 26, PRNs 27, and notes/orders 28. A summary of the work flow on this screen is shown in FIG. 15. These tabs also contain the counts of how many follow-ups, routine medications, and treatments are due, as well as a count of how many PRNs are available (for example, see reference number 29).

Figure 16:
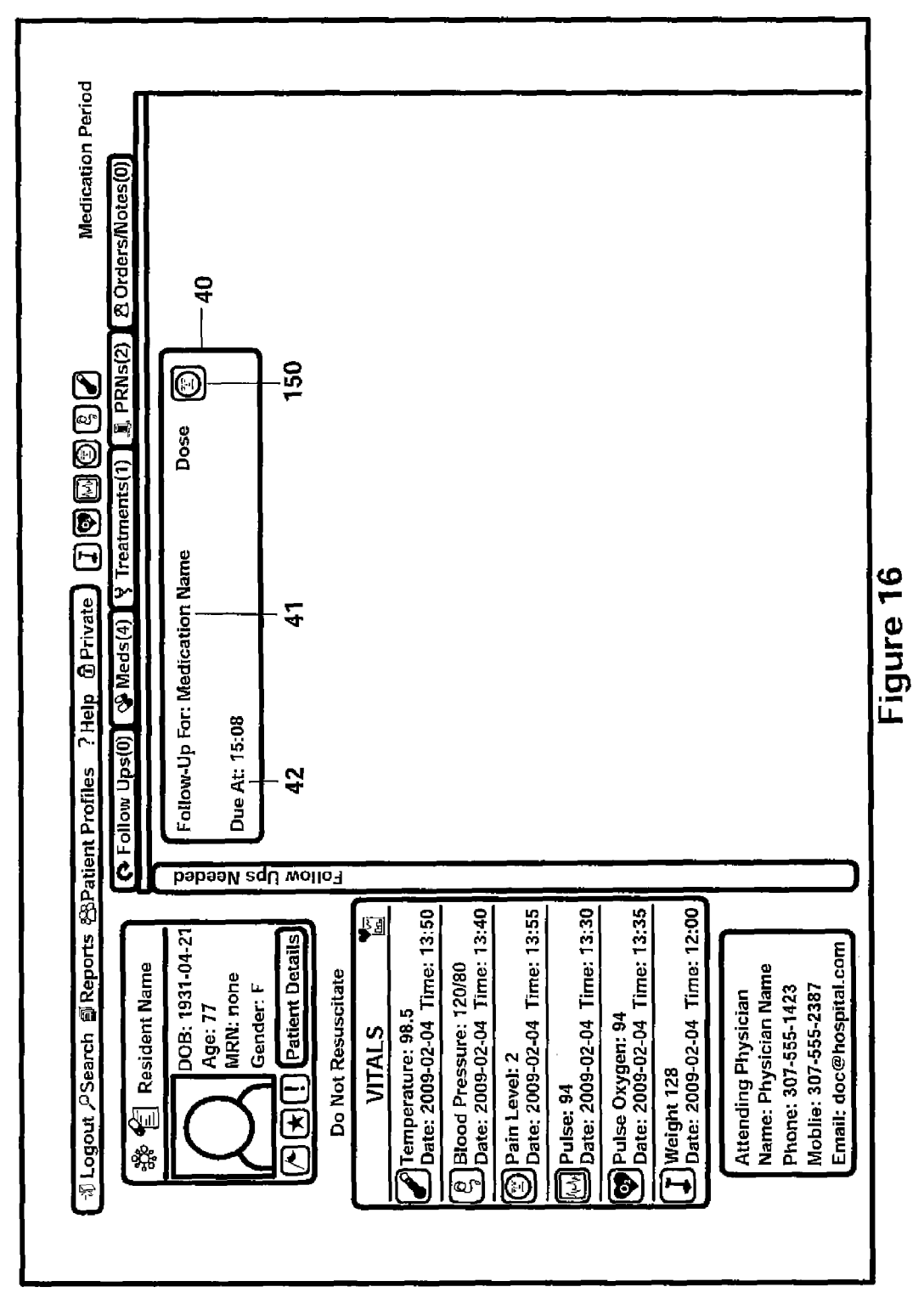
Figure 17:
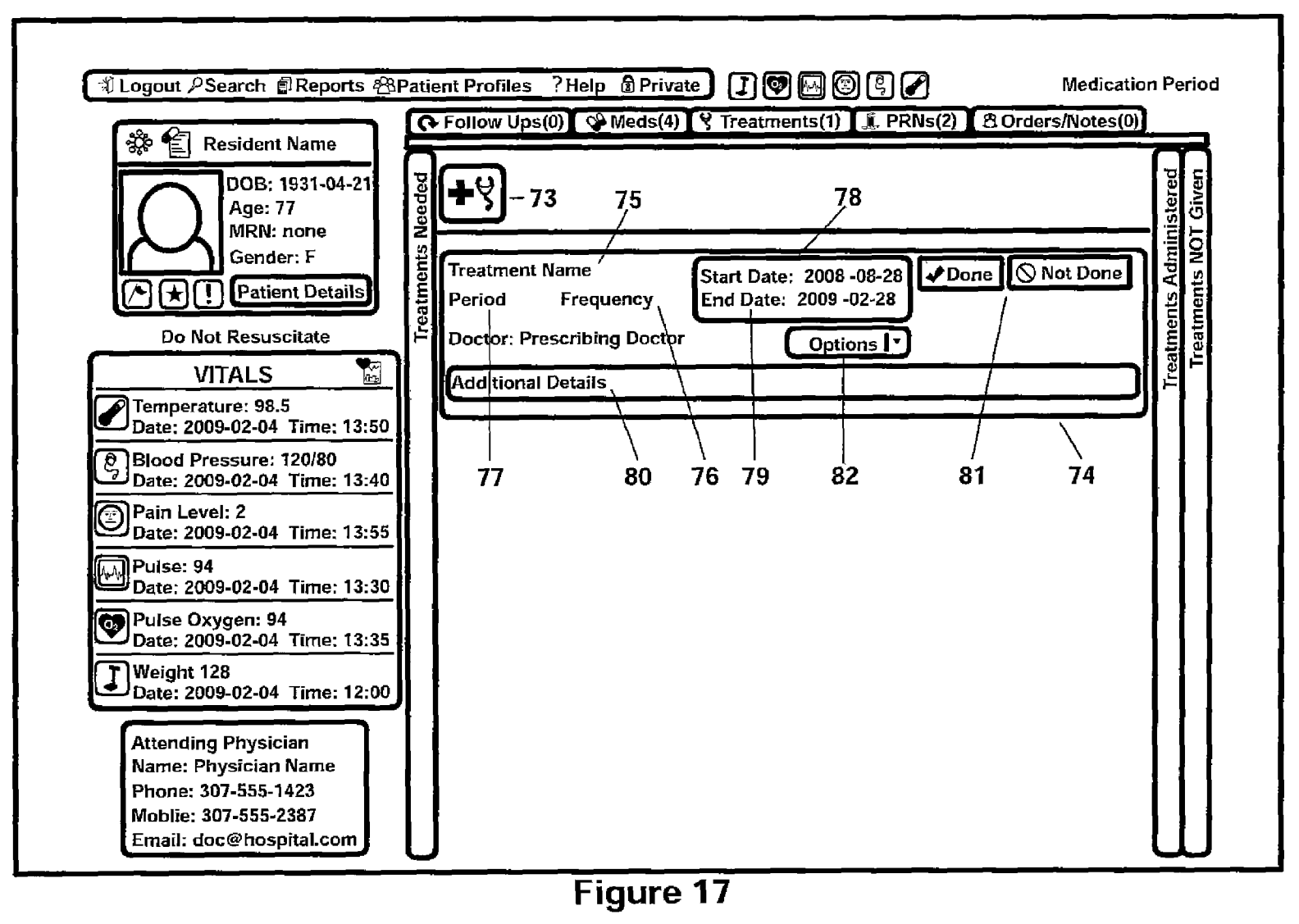
Figure 18:
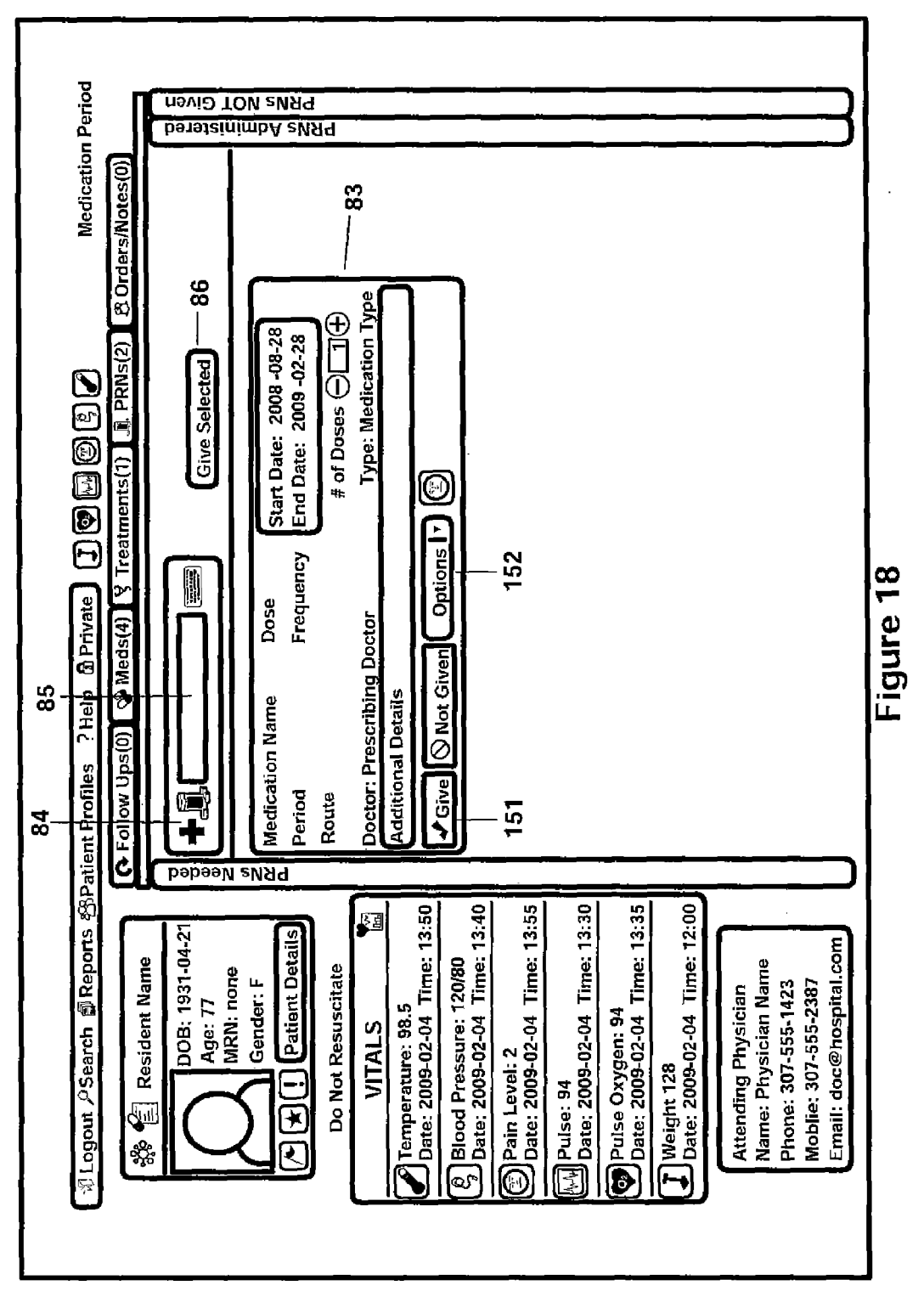
Figure 19:
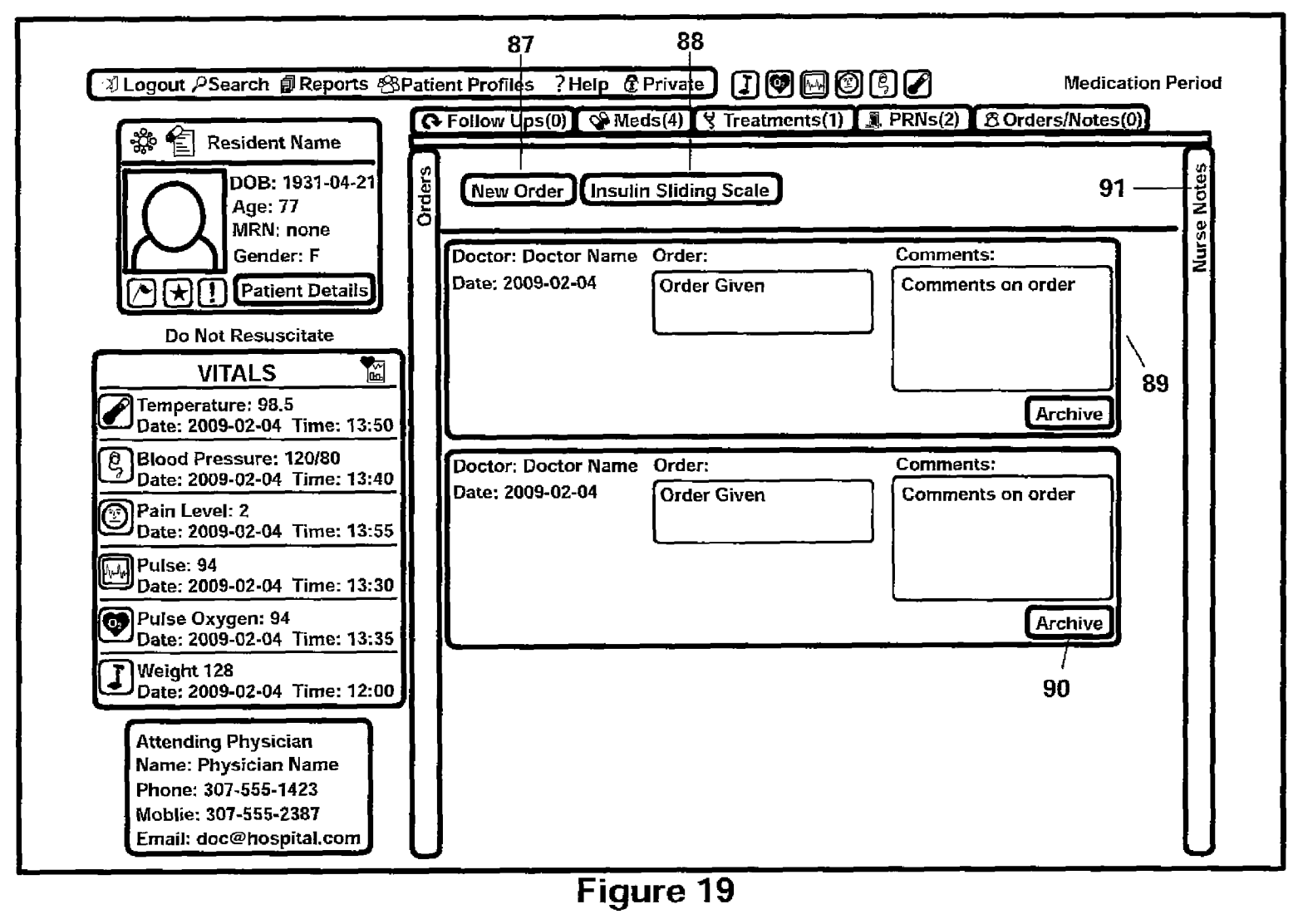

FIG. 16 shows the configuration of the patient screen if the patient has (over)due follow-ups. FIG. 14 shows the configuration if the patient has no (over)due follow-ups but has routine medications needed. FIG. 17 shows the configuration if the patient has no (over)due follow-ups or routine medications due but has treatments due. FIG. 18 shows the configuration if the patient has no (over)due follow-ups, routine medications needed, or treatments due, but has PRNs available. FIG. 19 shows the configuration when the healthcare provider clicks on the notes/orders tab 28 on FIG. 14.

Referring back to FIG. 14, the patient screen also displays information about the patient 30, the patient's vitals 31, any scheduled procedures or prerequisite procedures due in the current period 32, and the patient's physician 33. Access to further information about the patient is provided through displayed icons, including further detailed information (such as contact information) about the patient 34, quick access to different categories of nurse notes on the patient 35, the patient's allergies 36, medication profile 37, and charts of the patient's vital data for up to the last thirty days on which measurements were taken 38. These data and icons are shown on all of the configurations of the patient screen, providing the user with convenient access regardless of which procedure type is currently displayed.

Figure 26:
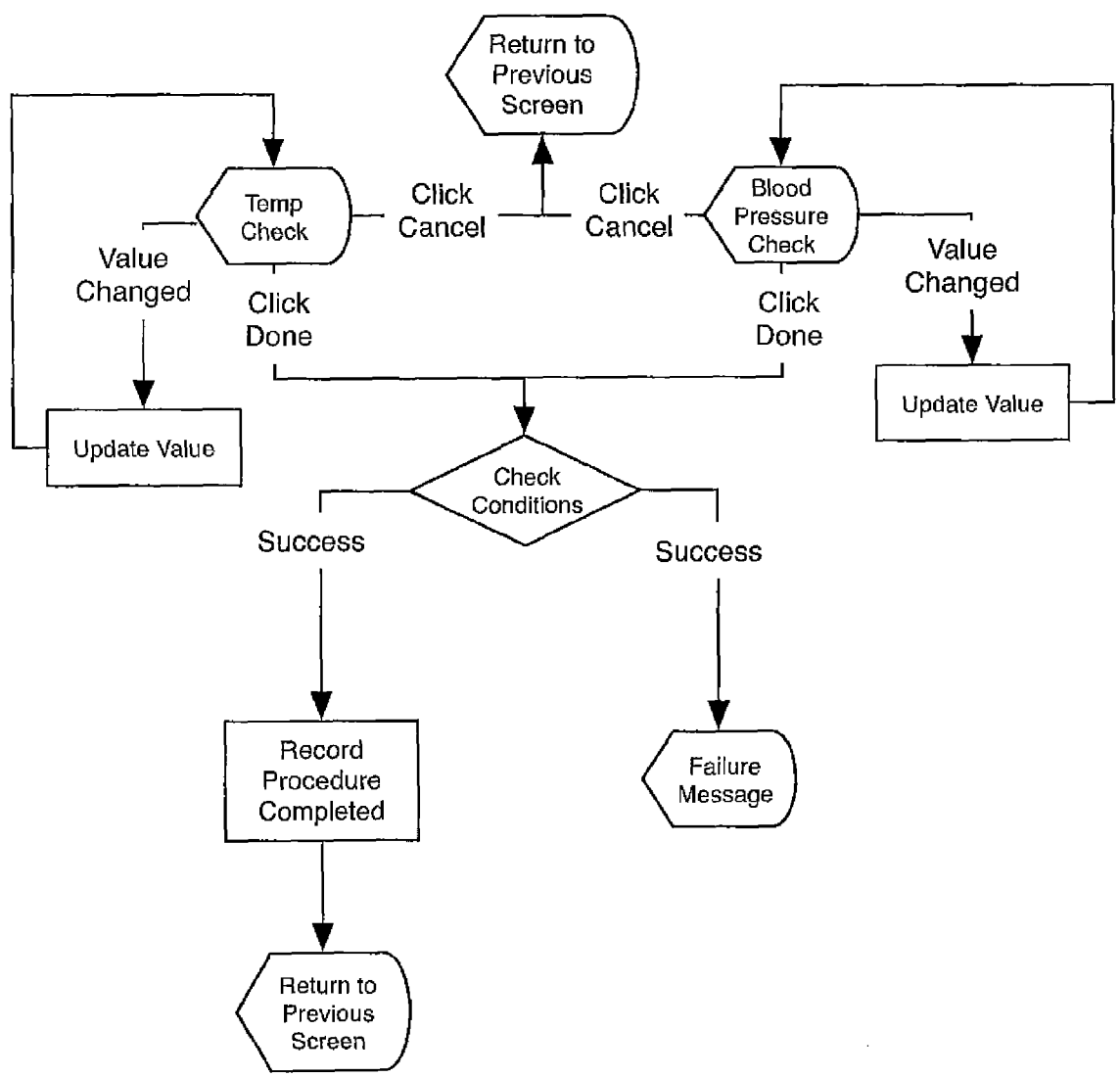
FIG. 26 is a diagram of the flow for the temperature and blood pressure screens.

The vitals panel 31 shows the most recent measurements and when they were taken for all of the patient's vital signs. Icons are provided here for the healthcare provider to enter new values for any of the vitals. The vitals currently included in the present invention are: temperature, blood pressure, pain level, pulse, pulse oxygen, and weight. In addition, the present invention is designed to enable new vitals to be easily added if needed. If a vitals icon is clicked, a screen appears enabling the healthcare provider to enter the current value(s) (see FIGS. 20-25). A summary of the work flow for temperature and blood pressure entry is shown in FIG. 26. The work flow for the other vitals screens is similar.

Also displayed at the top of the patient screen is a list of icons (32 on FIG. 14) for any scheduled procedures and certain types of prerequisite procedures of routine medications due in the current period 32. Clicking on these icons enables the healthcare provider to record the associated procedure as completed. The new values are automatically updated on the vitals panel if they are shown there, and if any of the procedures are prerequisites for currently due routine medications, the prerequisites are recorded as completed.

Figure 27:
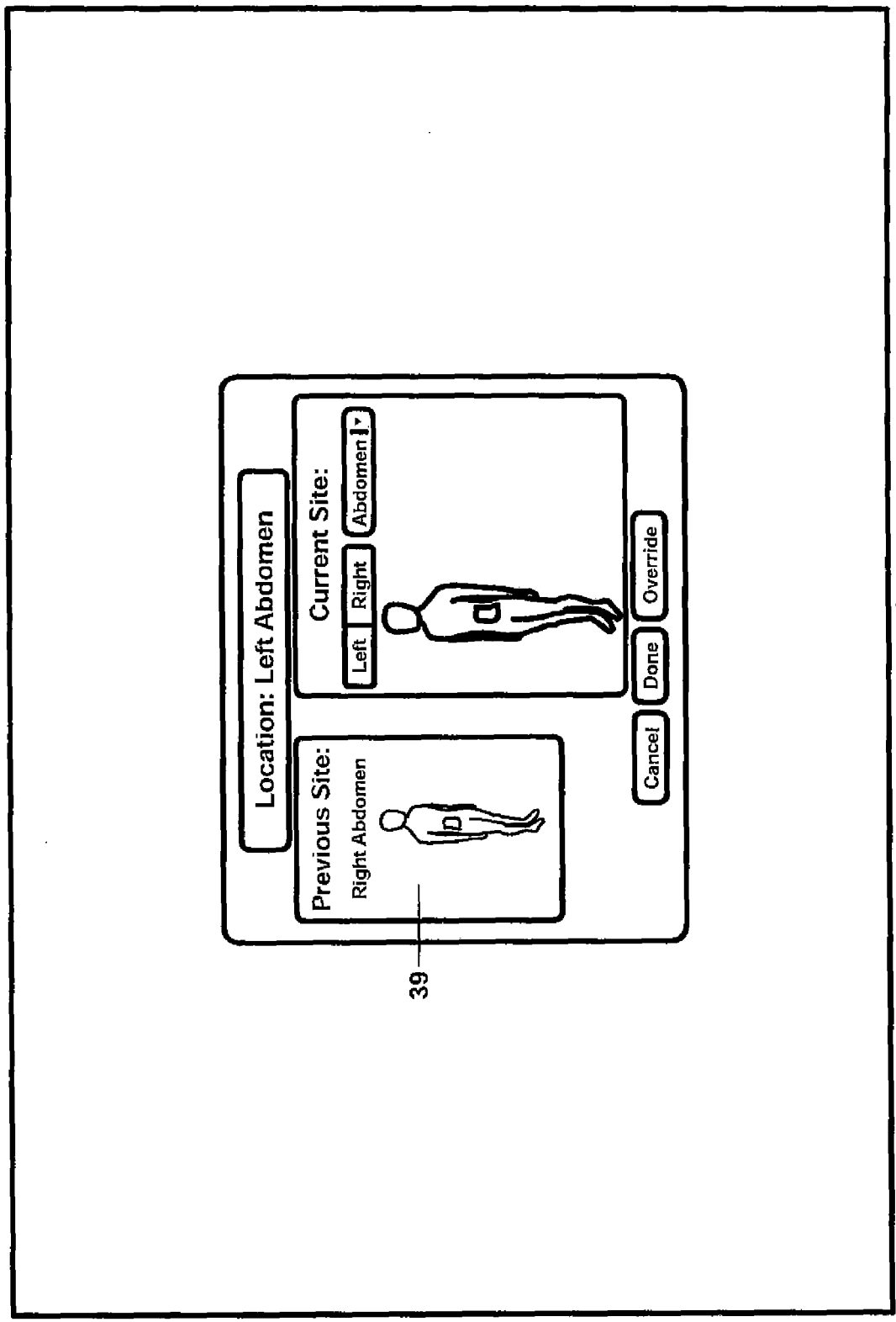
FIG. 27 is a screenshot of the location procedure screen.

In addition to all of the vital signs, the following procedures can also be recorded: location for indicating where on the body shots are given and blood sugar check. FIG. 27 shows the screen for the location procedure that enables the healthcare provider to record where on the patient's body a shot has been administered. It also shows the location of the last administration 39. The blood sugar check can be done in isolation or in conjunction with a potential insulin administration. Only certain types of prerequisite procedures (such as vital checks and blood sugar checks unrelated to insulin administration) may be shared among routine medications and will have an icon shown in this list (32 on FIG. 14).

Figure 20:
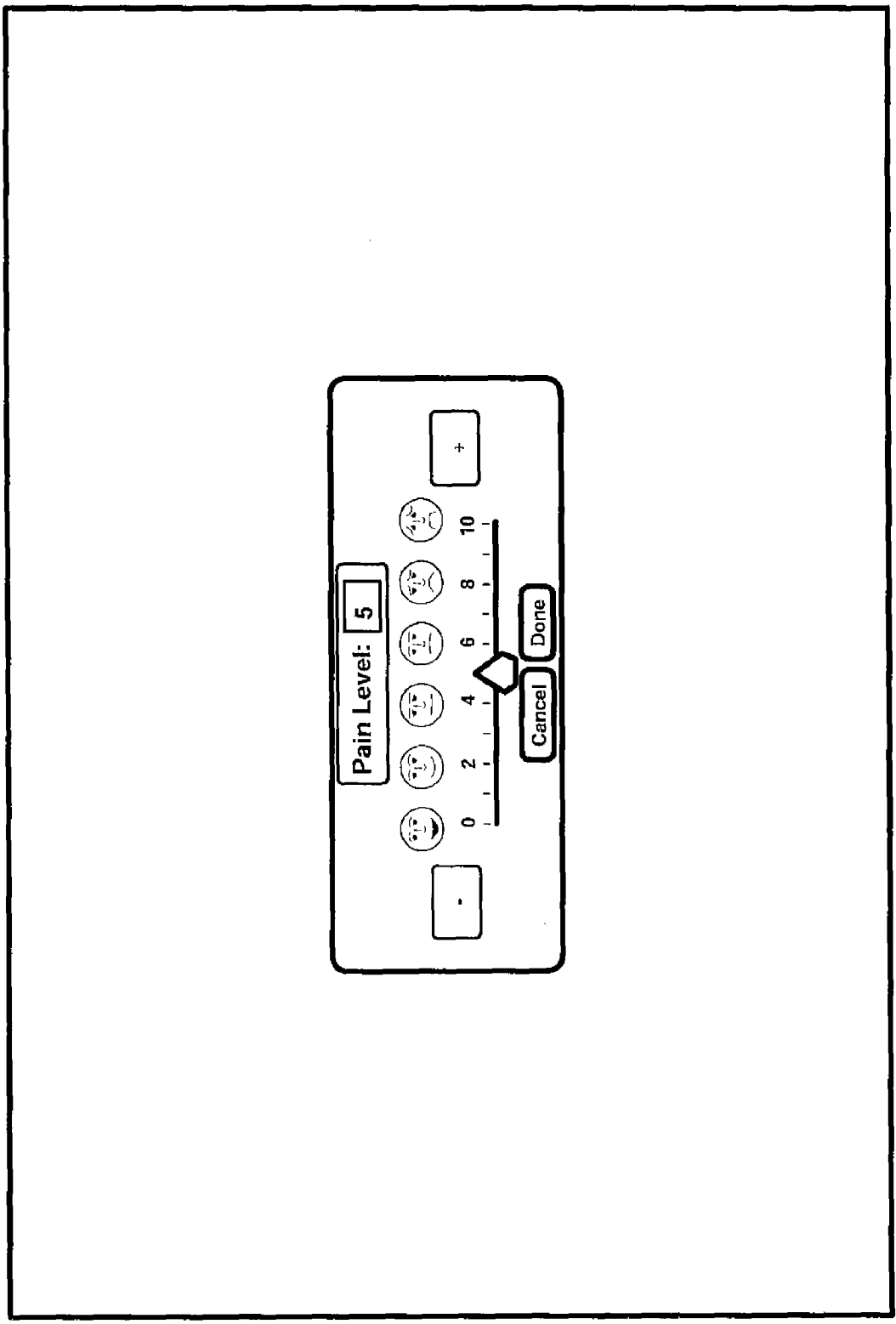
FIG. 20 is a screenshot of the pain check screen.
Figure 21:
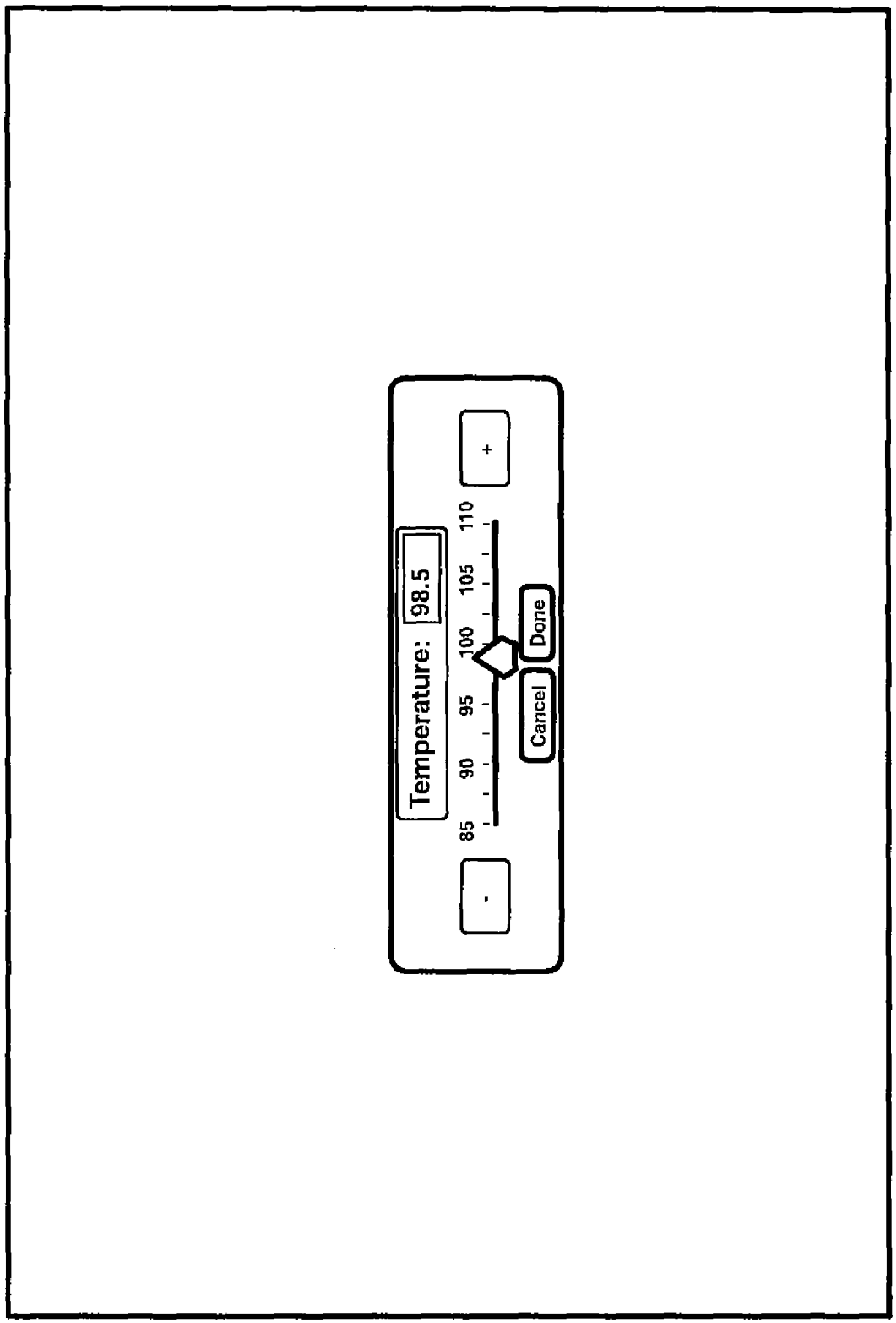
FIG. 21 is a screenshot of the temperature screen.
Figure 22:
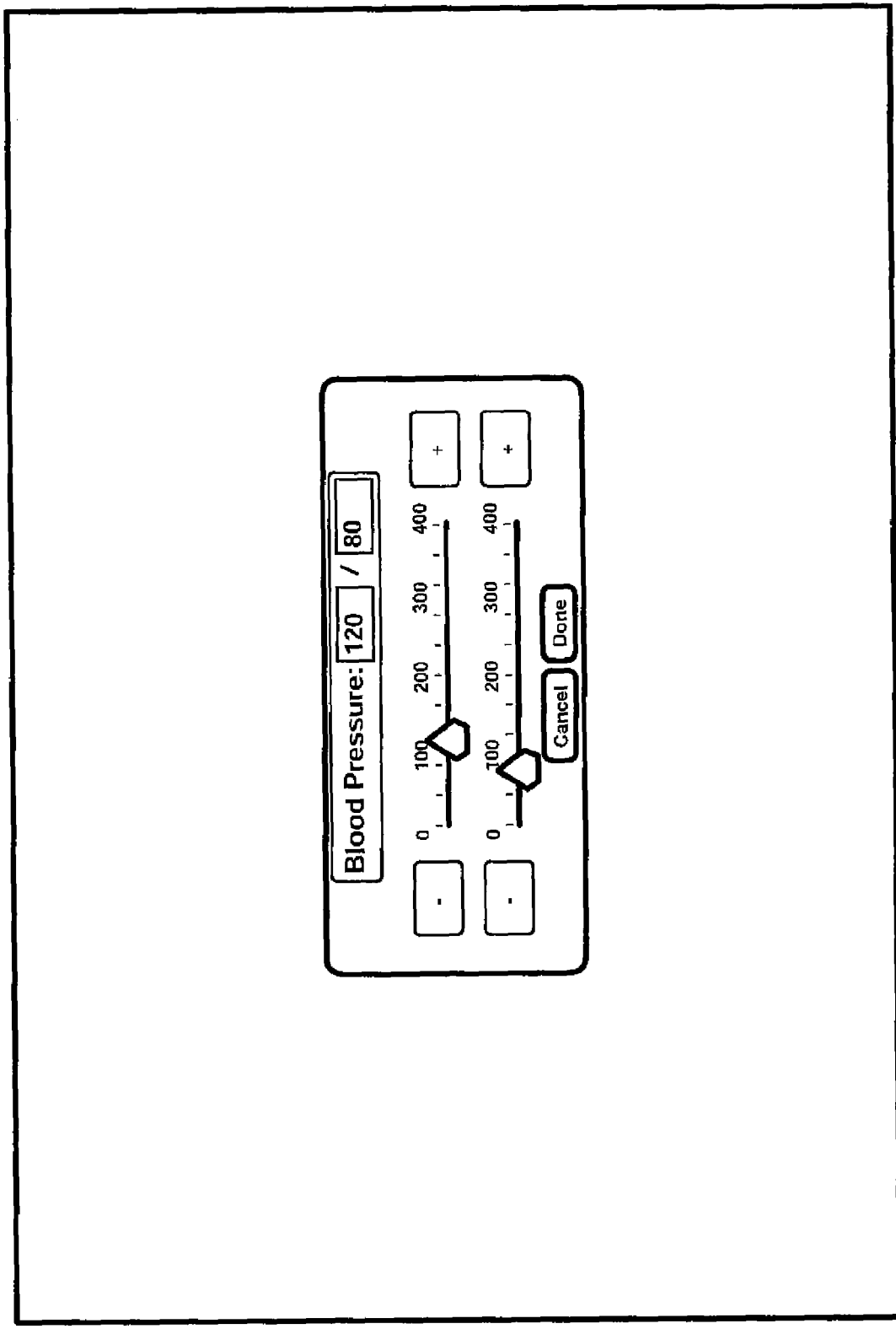
FIG. 22 is a screenshot of the blood pressure screen.
Figure 23:
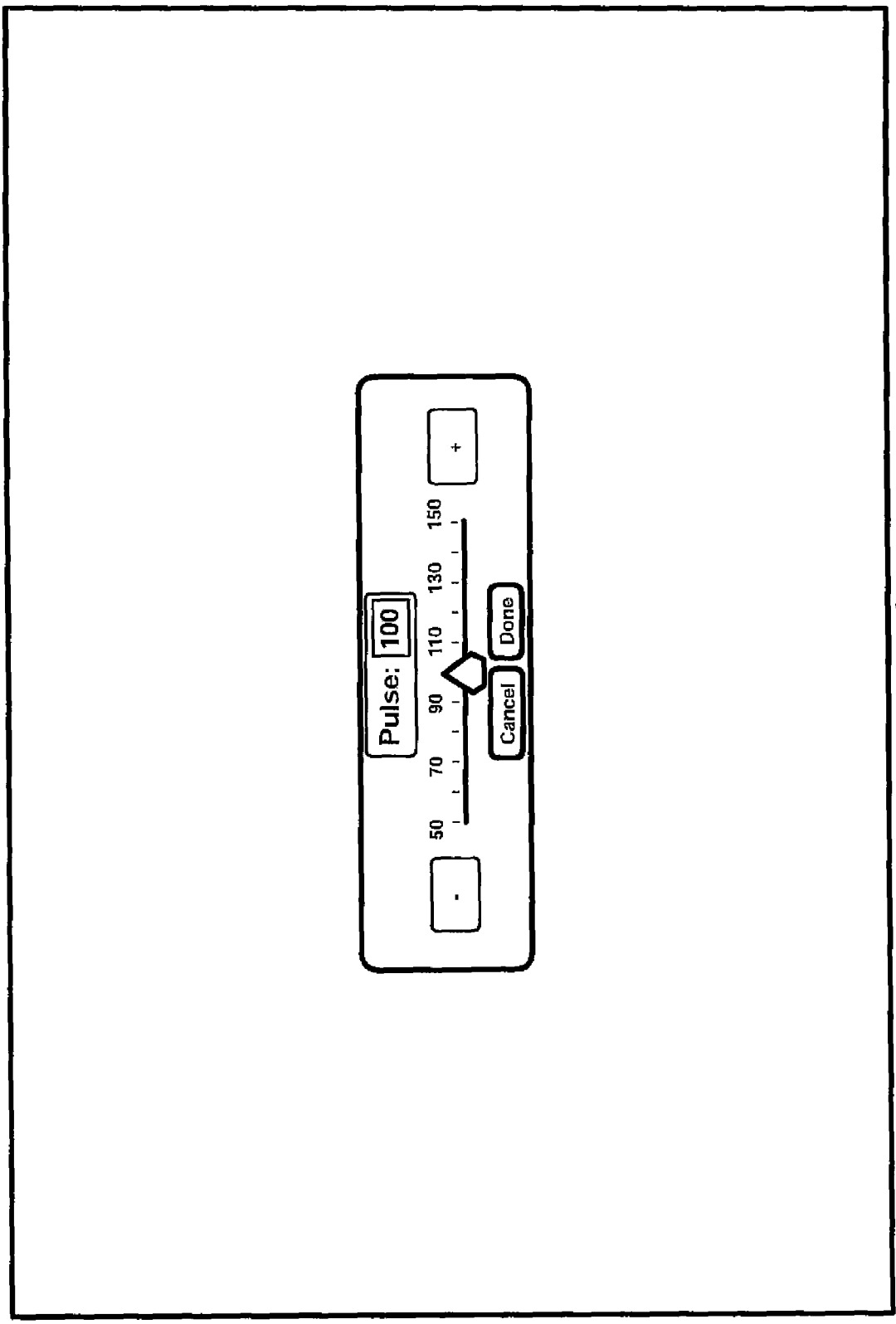
FIG. 23 is a screenshot of the pulse screen.
Figure 24:
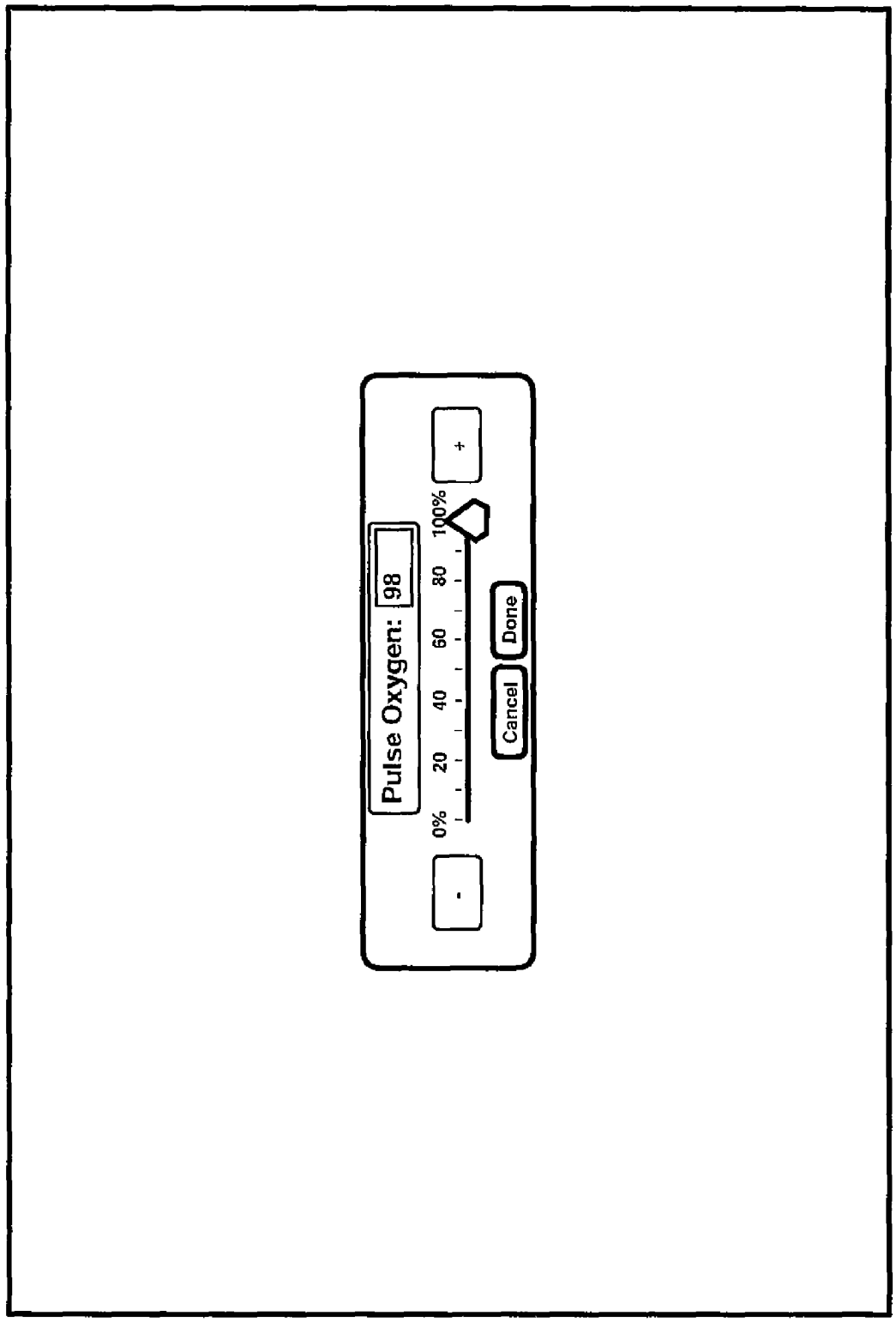
FIG. 24 is a screenshot of the pulse oxygen screen.
Figure 25:
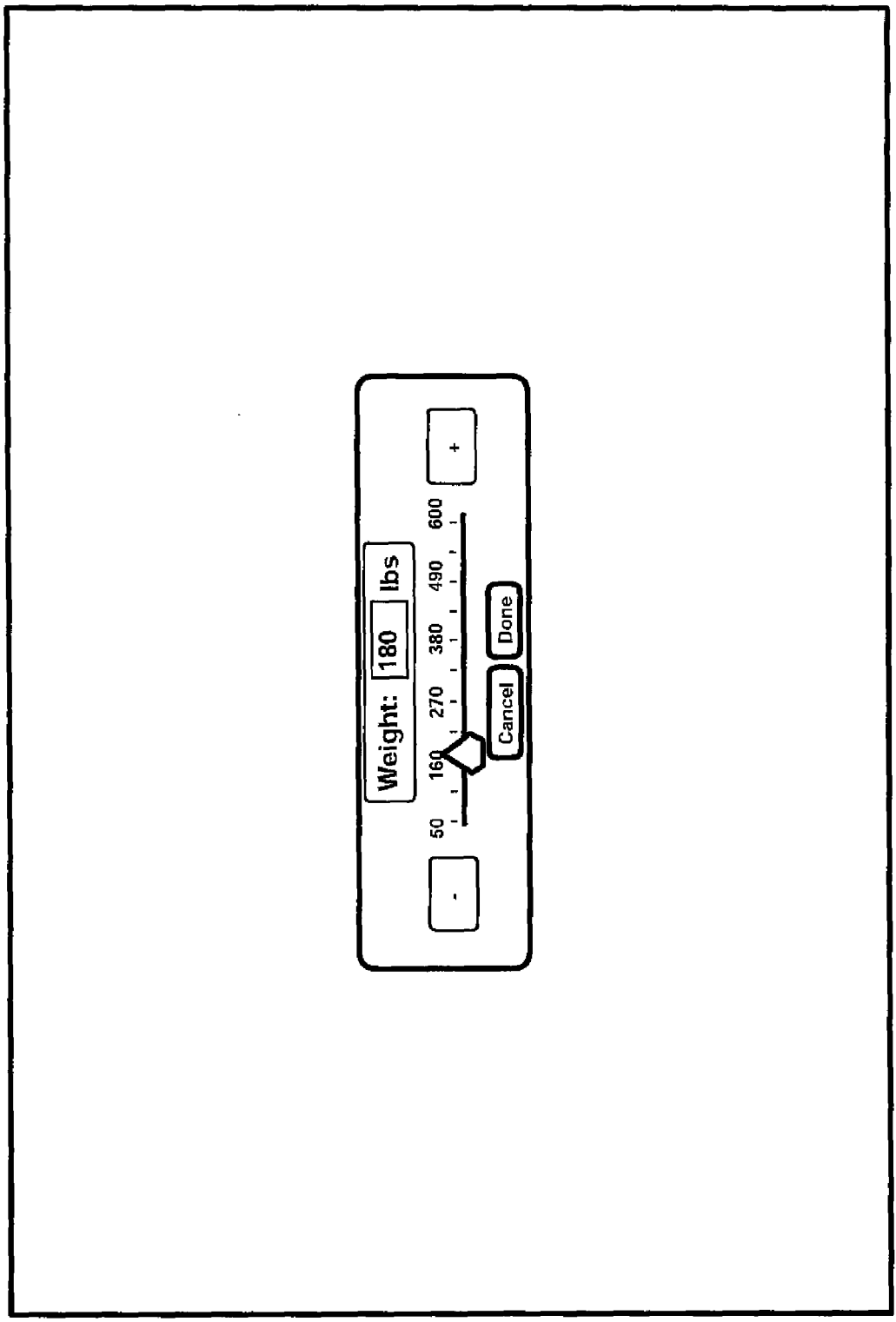
FIG. 25 is a screenshot of the weight screen.
Figure 28:
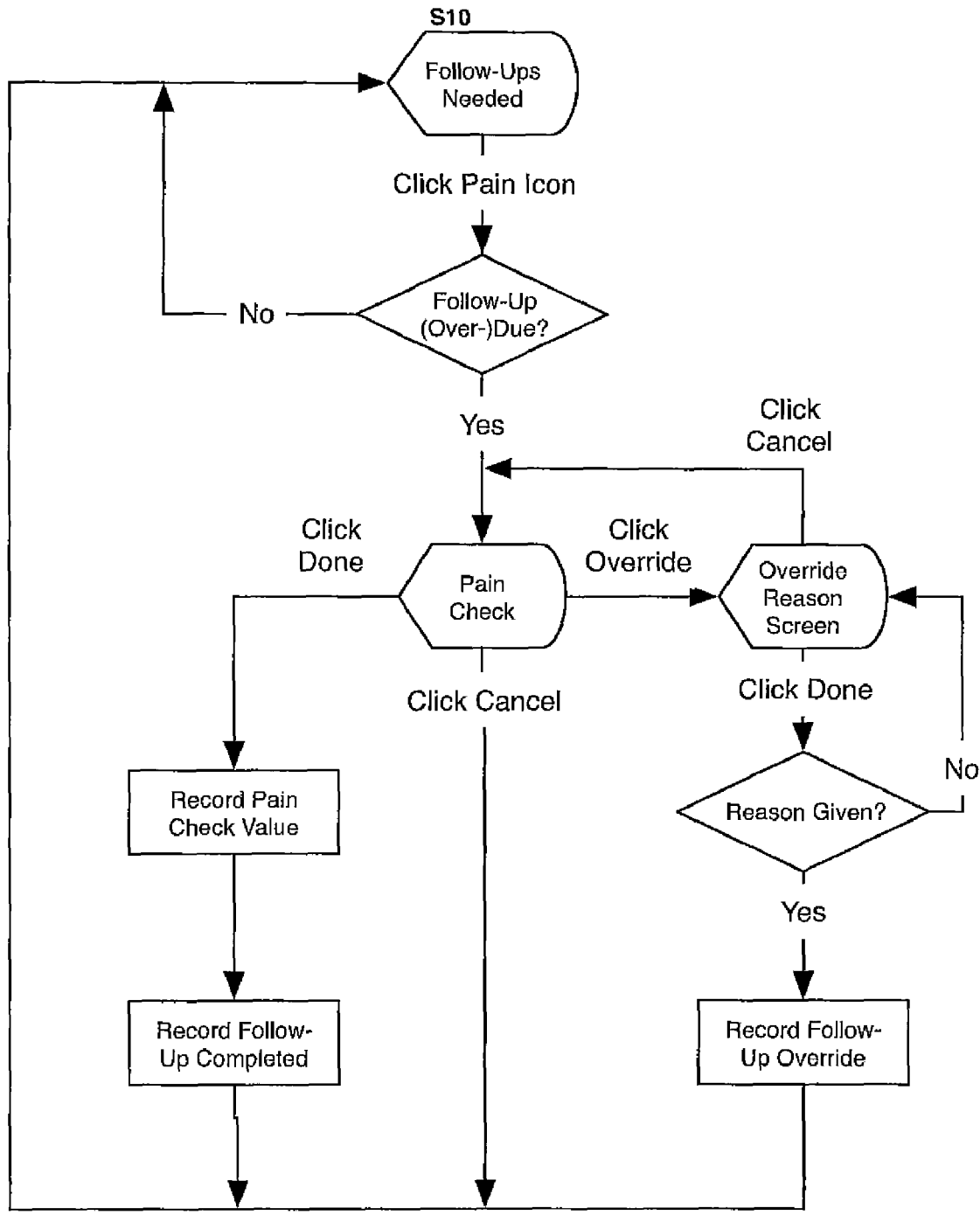
FIG. 28 is a diagram of the flow for the pain check screen.

FIG. 16 shows the current follow-ups for the patient in a list of buttons 40. Each button displays a follow-up and information about the original PRN 41. If a follow-up is not yet due, the time at which it is due is shown on the button 42. Otherwise, the number of minutes by which the follow-up is overdue is shown on the button. FIG. 28 shows the sequence that occurs when the healthcare provider clicks on the pain icon (51 on FIG. 14 in the button of an (over)due follow-up. FIG. 20 shows the screen that is displayed to enable the user to enter the result of the follow-up pain check (150 on FIG. 16).

Figure 29:
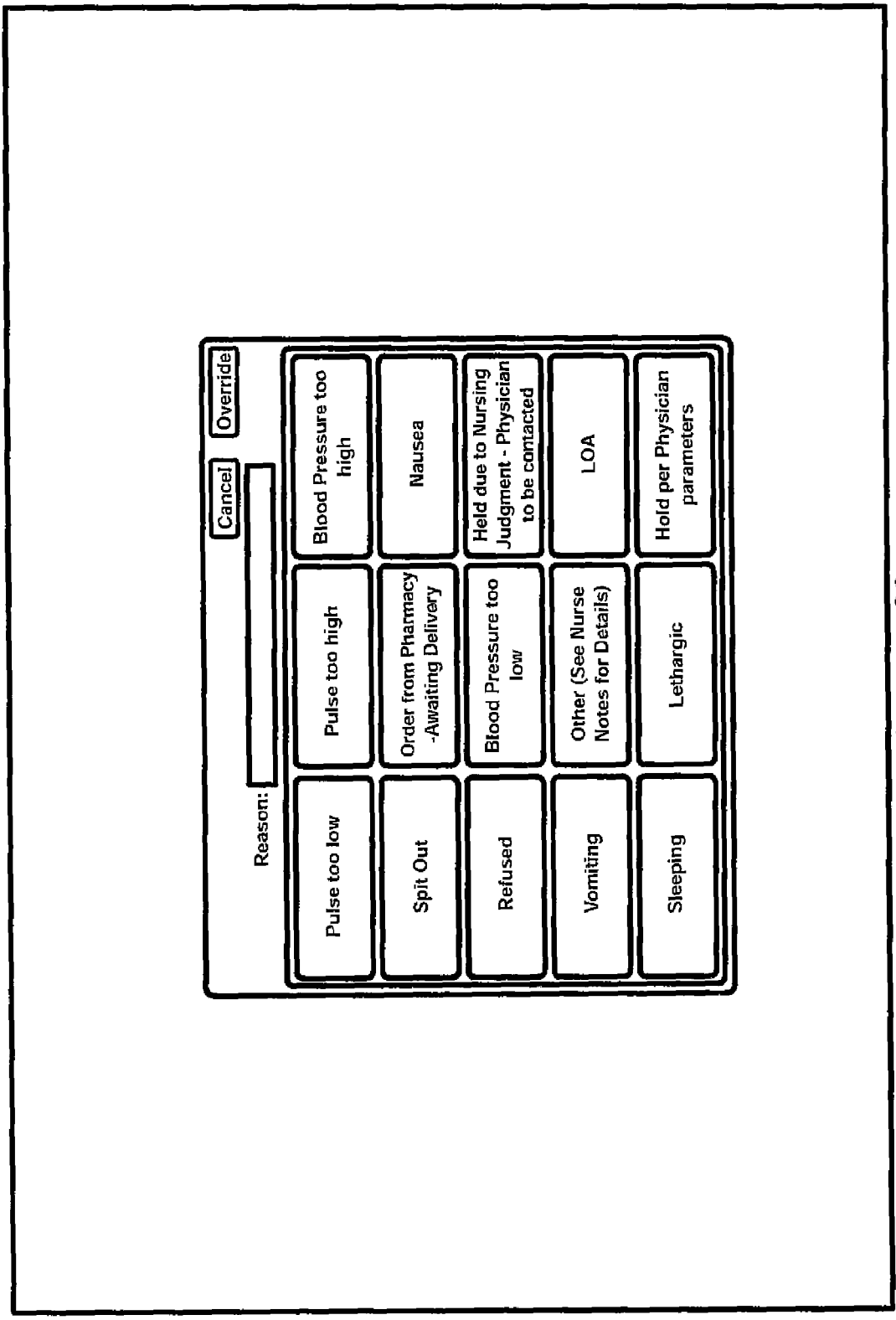
FIG. 29 is a screenshot of the not given reasons screen.

Once the pain check is completed, the follow-up disappears from the display. On the pain check screen, the user enters the result of the follow-up pain check and clicks "done." The user can also click "override," in which case the not given reasons screen (FIG. 29) is displayed, requiring the user to enter a reason for the override. In addition, "cancel" can be clicked to cancel the pain check action, which means the pain check must be done at a later time. Cancel is used when the care provider chooses not to do the pain check at the current time, whereas override is used to indicate that there is a reason that the pain check will not be done at all, in which case the reason is recorded.

FIG. 14 shows the routine medications for a patient. This screen is divided into three sections by an accordion: medications needed (FIG. 14), medications administered (FIG. 30), and medications not given (FIG. 31).

The medications needed section of the patient screen (FIG. 14) displays a list of medication buttons 43 for each routine medication needed, as well as an icon for opening the new medication order screen 44, a text box used to highlight medications in the displayed list 45, and an all options pulldown menu 46. Each medication button contains the name of the medication 47, the dose 48, the frequency 49, the period due if the medication has a period frequency (otherwise it shows the time at which the QH medication is due) 50, icons for any prerequisite procedures not yet completed 51, the route of administration 52, the prescribing physician 53, the type (such as tablet) 54, any comments provided on the script 55, buttons enabling the medication to be given or not given 56, an options pulldown menu 57, and an icon 135 that when clicked displays a picture of the medication (if a picture is available). The text box for highlighting medication buttons is used in two different ways depending on whether the institution is nurse-driven or pharmacy-driven. If it is pharmacy-driven, the user scans barcodes off of drug packages. If the user scans a bar code, the code matches a drug in the list, and the drug is due, the drug's button is highlighted, enabling the drug to be given or not given. If the institution is nurse-driven, the user types the first letter(s) of the name of a drug in the medication list into the text box, and a pulldown menu appears showing the drugs in the medication list starting with those letter(s). The healthcare provider can then quickly choose a drug from the list to highlight.

Figure 30:
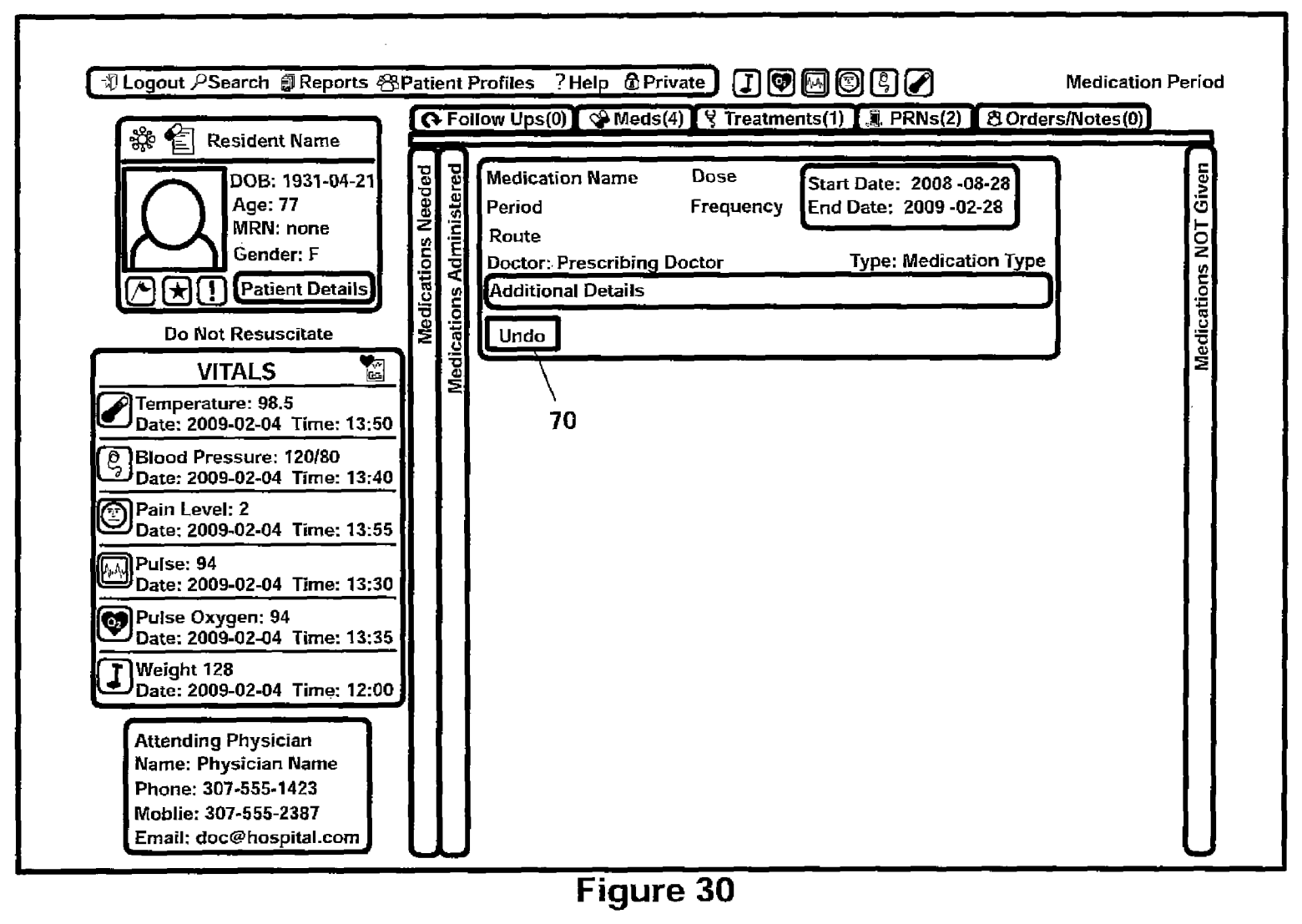

If the caregiver clicks on the give button (151 on FIG. 18) of a highlighted medication and no prerequisites remain, this medication is recorded as given in the cart station's database and is moved to medications administered (FIG. 30). If the medication had a QH frequency, the next application of this medication is added to the plan for this patient. If a medication has remaining prerequisites, an icon for each prerequisite appears on the medication button (51 on FIG. 14). To perform a prerequisite, the user clicks on its icon, and a screen (such as FIG. 21) appears enabling the results of the prerequisite to be recorded.

Figure 31:
FIG. 31 is screenshot of the patient screen showing medications not given.

If the user clicks on the not given button of a highlighted medication, the user is prompted for a reason (FIG. 29), this event is recorded, and the medication is moved to the medications not given screen (FIG. 31).

There is also an options button on each medication button 57. Clicking on this button exposes a pulldown menu providing some additional actions on medications including: postpone, hold, and D/C. If the user chooses postpone, the user is prompted to provide a reason (see FIG. 29), and, if a reason is given, the medication is postponed into the next period if it is a period medication or for the repeat interval if it is a QH medication. Postponing a medication will cause it to move to the medications not given screen, where it is displayed with an indication that it has been postponed. This action is also recorded in the database. When the medication becomes due again, it is automatically moved back to the medications needed screen.

Figure 32:
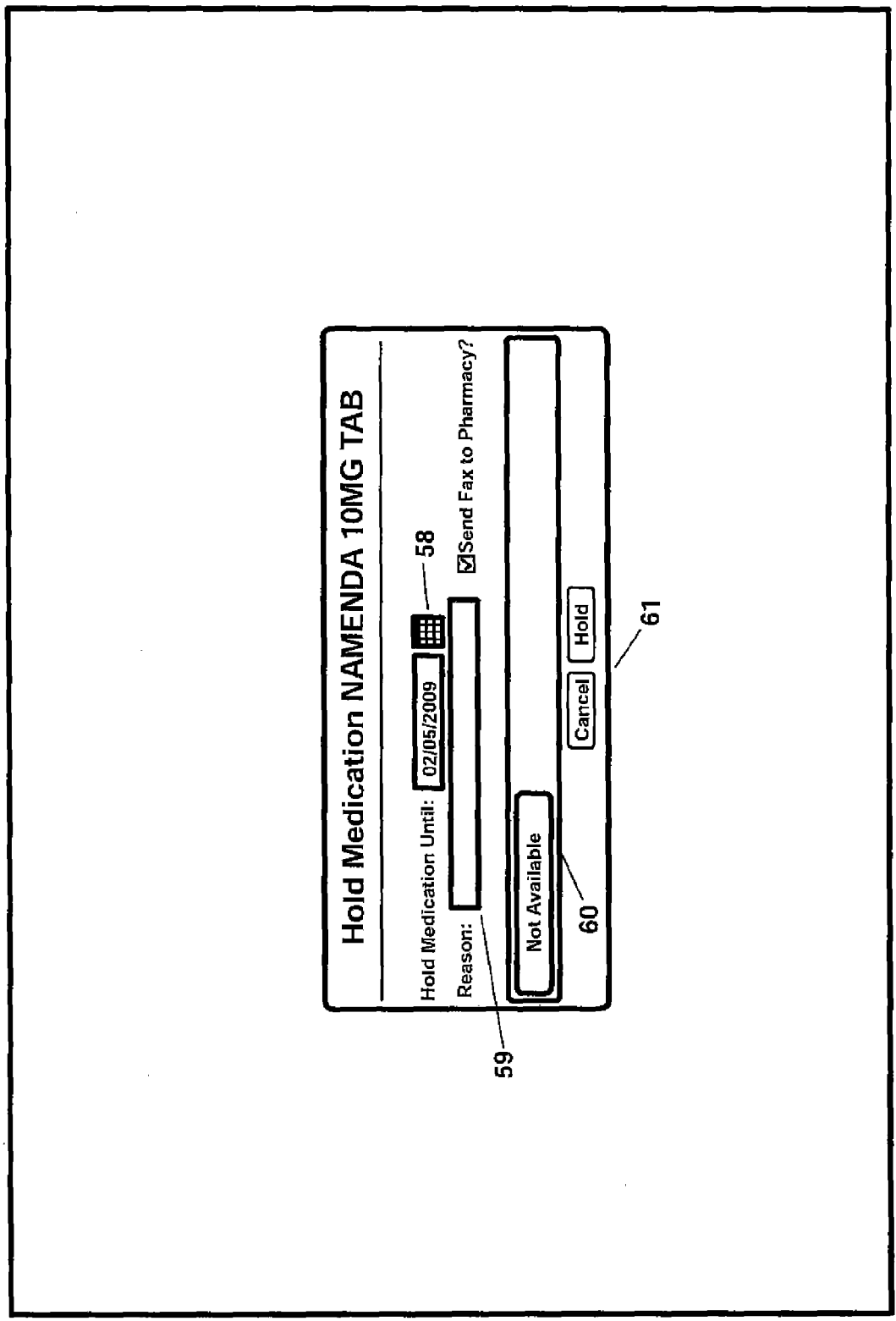
FIG. 32 is a screenshot of the medication hold screen.

If the user chooses hold, the medication hold screen (FIG. 32) is displayed, enabling the healthcare provider to supply a hold date 58 and reason 59. The reason can be typed into 59 and/or selected from a preset list of reasons 60. If the healthcare provider clicks the hold button 61, the medication is held until a date entered by the healthcare provider. This action causes the medication to be moved to the medications not given screen and marked as held; this action is also recorded in the database. If the user chooses D/C (for "discontinue"), the D/C medication screen (FIG. 33) appears, enabling the medication to be discontinued. On this screen, the healthcare provider can select the doctor discontinuing the medication 62, the order date 63, and supply comments 64. The name of the medication 65 being discontinued is also shown. The healthcare provider clicks 66 to submit the D/C order.

Figure 34:
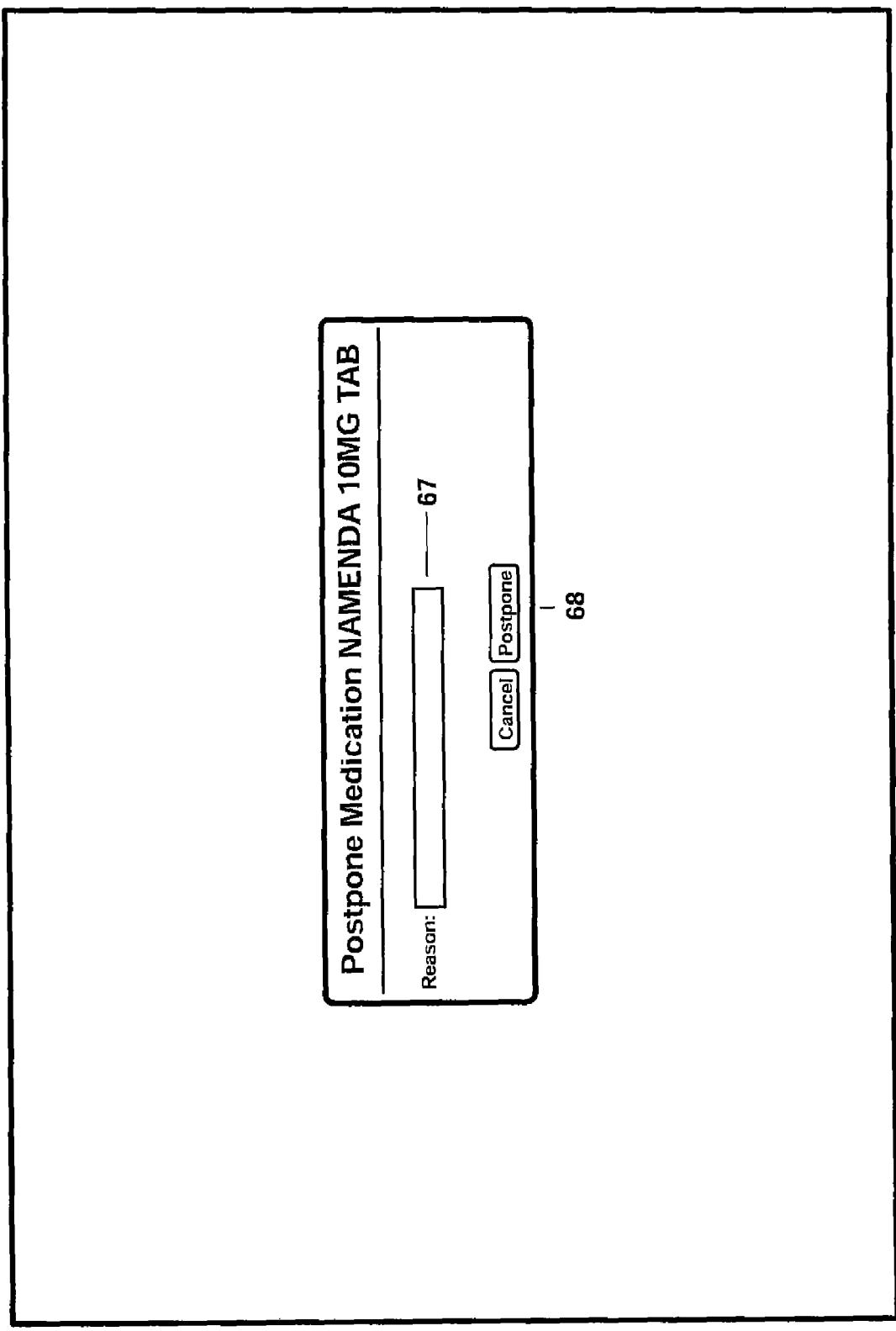
FIG. 34 is a screenshot of the postpone medication screen.

The all options pulldown menu above the button list 46 enables the user to take action on groups of the medications in the list simultaneously. This pulldown menu contains three operations: give all, postpone all, and not give all. Give all is used to give all highlighted medications simultaneously. Postpone all (FIG. 34) requires the user to provide a reason 67, and if a reason is provided and the healthcare provider clicks 68, all of the patient's displayed drugs are postponed. Not give all behaves like postpone all except that it records each displayed routine medication as not given.

FIG. 30 shows the section that slides into view when the user clicks on the medications administered tab 69 on FIG. 14. When there are medications that have been given in this period, they are displayed in a list similar to the one on the medications needed screen; however, the medication buttons in this list provide only an undo button 70 that enables the medication administration to be undone for an institution-defined window of time after it is marked as given or not given. If the user clicks 70 during the allowed time, the undo action is recorded, and the medication is moved back to the medications needed section.

FIG. 31 shows the section that slides into view when the user clicks on the medications not given tab 71 on FIG. 14. When there are medications that have been marked not given in the current period, they are displayed in a list similar to the medications needed screen; however, the medication buttons in this list provide only an undo button 72 that enables the not given operation to be undone for an institution-defined window of time after the original action was taken. If the user clicks 72 during the allowed time, the undo action is recorded, and the medication is moved back to the medications needed tab.

FIG. 17 shows the screen that is displayed when the healthcare provider clicks on the treatments tab 26 on FIG. 14. This screen shows information about and enables caregiver actions on a patient's treatments. Like the medications screen (FIG. 14, it is divided into three sections by an accordion: treatments needed, treatments administered, and treatments not given. The purpose and functionality of these different screens is very similar to FIGS. 14, 30, and 31. The treatments needed screen has an icon at the top 74 for adding new treatments and displays a list of treatment buttons 74 similar to the medication buttons. Each button provides information about a treatment including: the treatment name 75, frequency 76, period or time of application 77, start date 78, end date 79, and any comments provided with the prescription 80. Each button also has done and not done buttons 81, as well as a pulldown menu for additional options 82.

Just as with routine medications, treatments cannot be marked completed until they are due. If the user clicks the done button on a treatment and the treatment is due, it is recorded as completed and moved to the treatments administered screen. If the treatment has a QH frequency, the next application is added to the plan for this patient. If the not done button is clicked and the treatment is due, this action is recorded, and the treatment is moved to the treatments not done screen.

The options pulldown menu on the treatment button provides the same additional operations as on the routine medication button, and these operations work the same way. The treatments administered and treatments not given screens work the same way as FIGS. 30 and 31, respectively. As with medication and PRNs, treatments marked administered or not given can be undone for an institution-defined period of time.

Treatments can be of two types: regular and PRN. Regular treatments work similarly to routine medications. They become due in a specified period or at the specified time of day, and if they are not either marked given or not given, a treatment error is recorded. For treatments with period frequency, treatment errors are recorded at the end of the specified period. For QH treatments, errors are recorded at the end of the institution-defined window after they are due.

PRN treatments are used for treatments that are not required but that can be administered as needed (similar to PRN medications). PRN treatments may only have QH frequencies, and failure to administer such a treatment is never recorded as an error. The time of the first application of the day of this type of treatment is "as needed" unless the last time it was applied yesterday requires it to be allowed only after a certain time today. The times of subsequent applications are scheduled for at least the interval time from the prior application. For example, if the QH frequency of a procedure is Q4H (i.e., at least four hours apart), then the cart station schedules next applications for four hours later than prior applications.

FIG. 18 shows the screen displayed when the healthcare provider clicks on the PRNs tab 27 on FIG. 14. This screen enables the healthcare provider to check and administer available PRNs, undo PRNs marked given, and check on PRNs marked not given. It is organized like and functions similarly to the medications screen (FIG. 14) with three sliding sections in an accordion. Like FIG. 14, the available PRNs section displays a list of medication buttons 83, an icon for opening the new PRN order screen 84, a text box used to highlight PRN buttons in the displayed list 85, and a give selected button 86. PRNs may be highlighted when they are available, and if their prerequisites are complete, they may be marked as administered, in which case they are moved to the PRNs administered section, and the next application is added to the patient's plan. PRNs in the PRNs administered section may be undone for an institution-defined period of time (as explained above for medications and treatments). As with other procedures, all actions taken on PRNs and their prerequisites are recorded by the cart station.

PRN buttons also have an options button (152 on FIG. 18) that, when clicked, lists two possible additional actions that can be taken: hold and D/C. If either of these options is selected, the user is prompted in the same way as for holding and discontinuing routine medications. If a PRN is held or discontinued, this action is recorded, and the button for that PRN is moved to the PRNs not given screen (FIG. 31), where the action can be undone for an institution-defined period of time after the original action was taken.

There is also a give selected button 86 above the button list that enables the healthcare provider to simultaneously record each of the highlighted PRNs as given. If the prerequisites for any of the PRNs highlighted at the time this operation is selected have not been completed, an alert is displayed, and those PRNs are not marked as given.

FIG. 19 shows the screen displayed when the healthcare provider clicks on the orders/notes tab 28 on FIG. 14. This screen is where orders other than new medication, new PRN, new treatment, new scheduled procedure, or D/C medication can be viewed and where nurse's notes can be viewed. It is divided into orders (FIG. 19) and nurse notes (FIG. 35) by an accordion.

Figure 45:
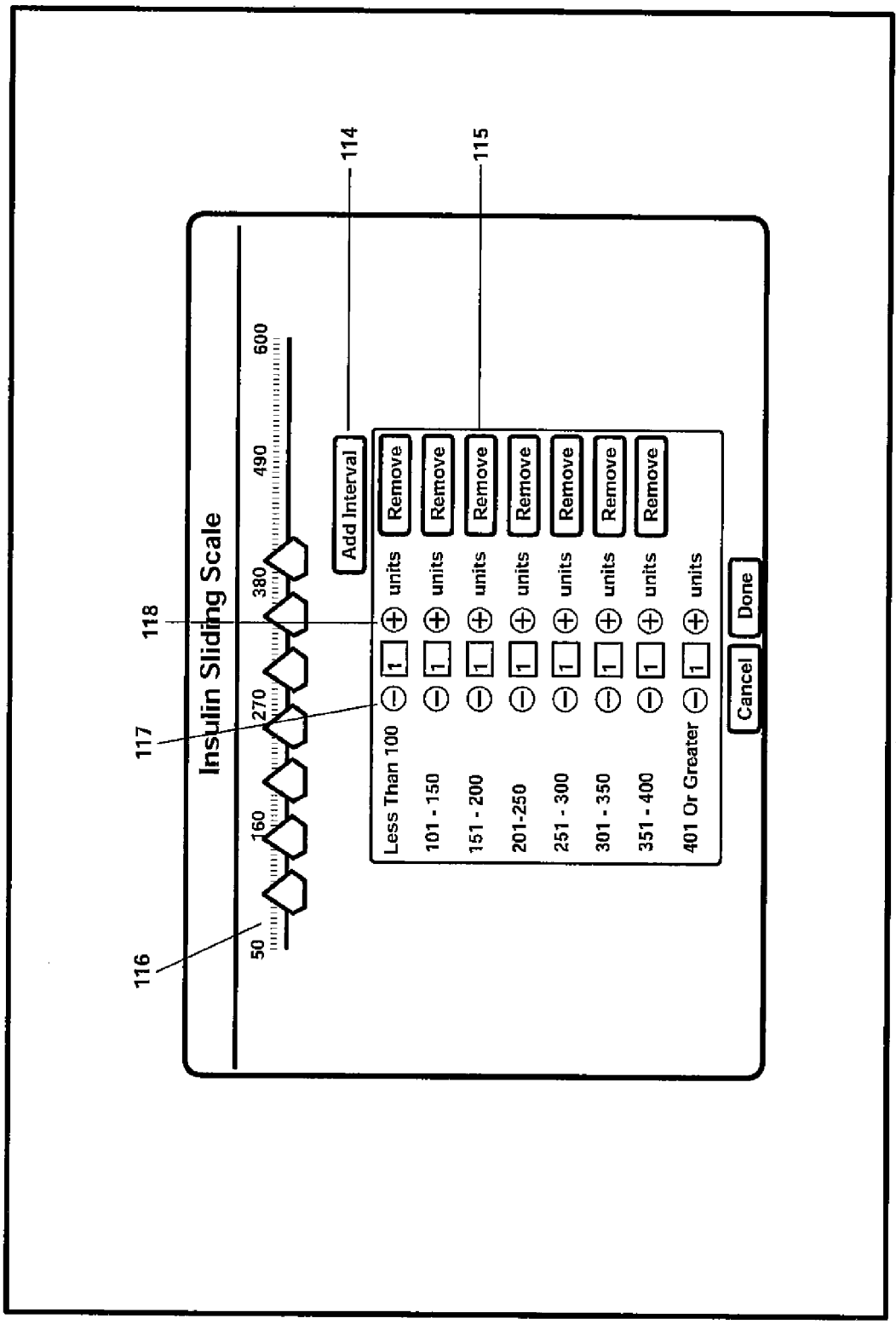
FIG. 45 is a screenshot of the insulin sliding scale screen.

The new order button 87 at the top of this screen provides another access point to the new orders screen. The insulin sliding scale button 88 at the top of this screen calls up the insulin sliding scale screen (FIG. 45). This screen also shows a list of the patient's orders 89. When an order is no longer in effect, it can be archived by clicking its archive button 90.

Figure 35:
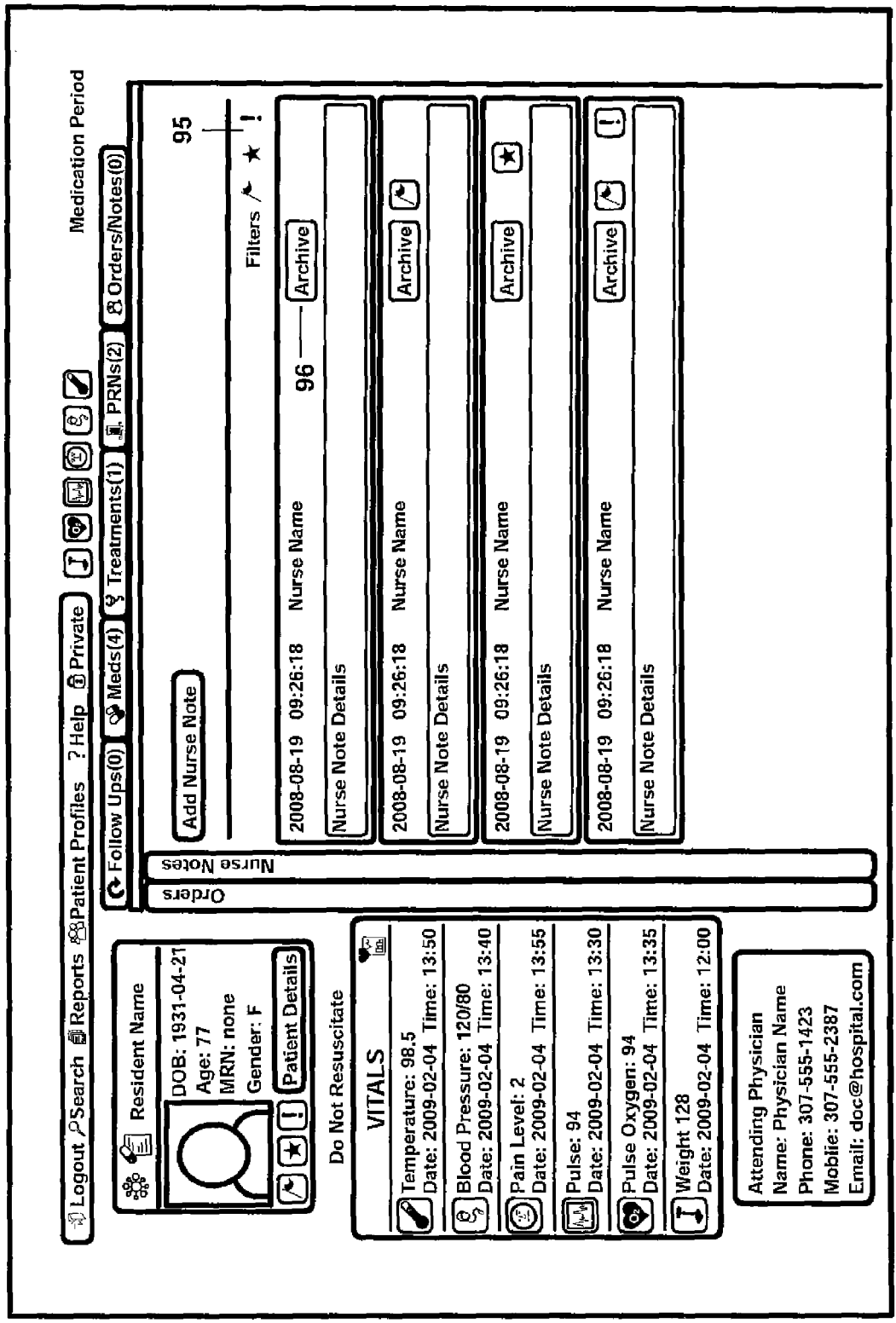
FIG. 35 is a screenshot of the patient screen showing nurse notes.
Figure 36:
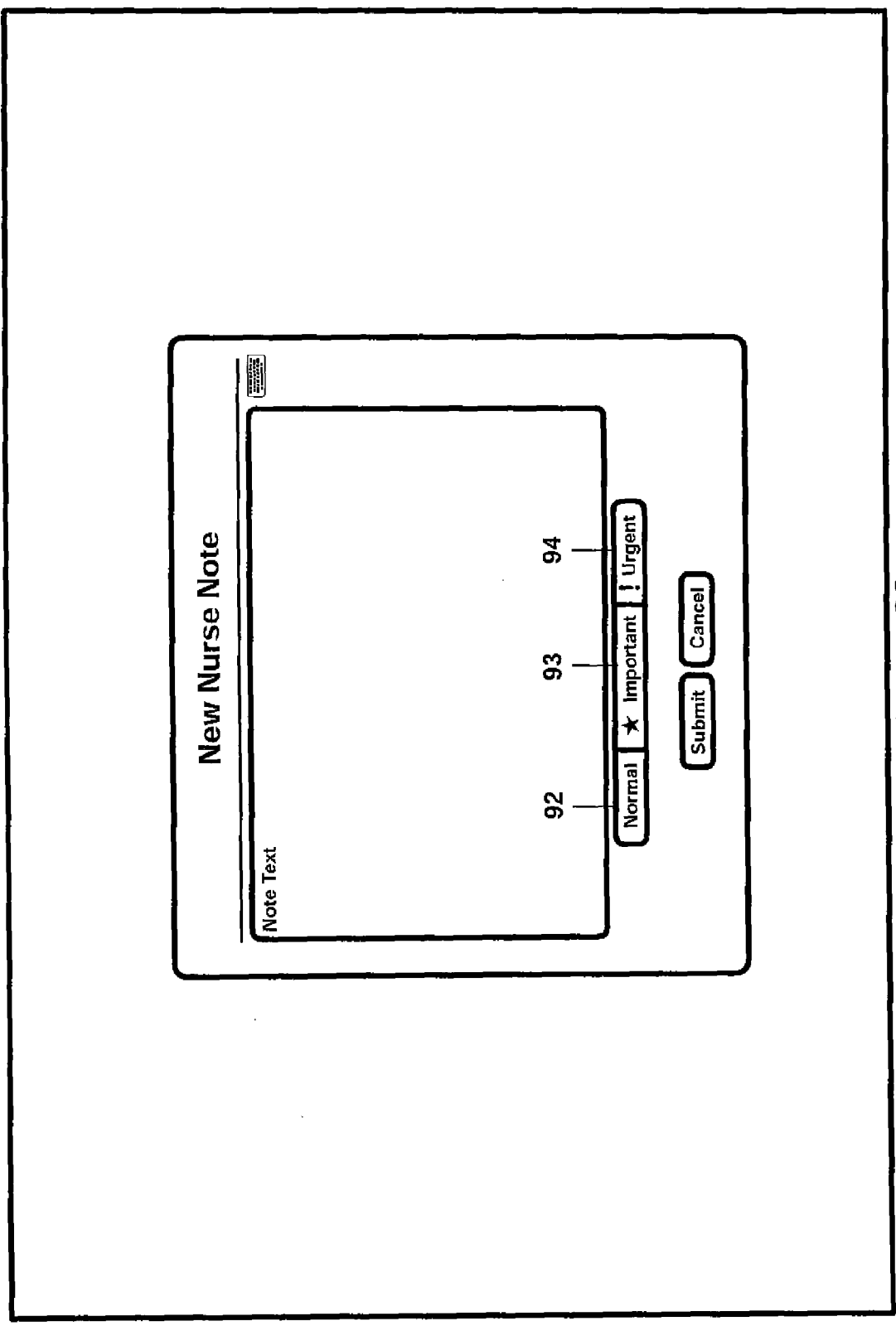
FIG. 36 is screenshot of the new nurse note screen.

FIG. 35 shows the section that slides into view when the healthcare provider clicks the nurse notes tab 91 on FIG. 19. The nurse notes section displays the nurse notes on a patient and enables the healthcare provider to enter new notes. Notes are shown in a list of buttons, each one showing the date entered and the text of the note. On the far right of the button is an archive button and icons indicating whether or not the note is new, important, or urgent. When a note is entered, it can be marked as normal 92, important 93, or urgent 94 (see FIG. 36). A note is considered new for an institution-defined number of days after it is entered.

Which notes are shown in the display and the order in which they are shown is controlled by three filter icons at the top of the button list 95 (see FIG. 35). If all of the filter icons are turned off, all of the patient's notes are shown with new notes first, sorted by urgency with most recent first in each urgency category, then old notes are shown sorted by urgency with most recent first. If all filter icons are on, all new notes plus any note that is flagged urgent or important is shown. The notes are sorted first by urgency, with the most recent note in each category shown first. If the urgent or important control icon is on by itself all notes in that category are shown sorted with most recent first. If only the new icon is on, all new notes are shown sorted first by urgency and then by date, with newest first. If any pair of control icons is on, all notes that are in either icon category are shown sorted by urgency and then by creation date. The archive button 96 enables notes to be archived, in which case they are removed from the cart station display and recorded as archived.

Figure 39:
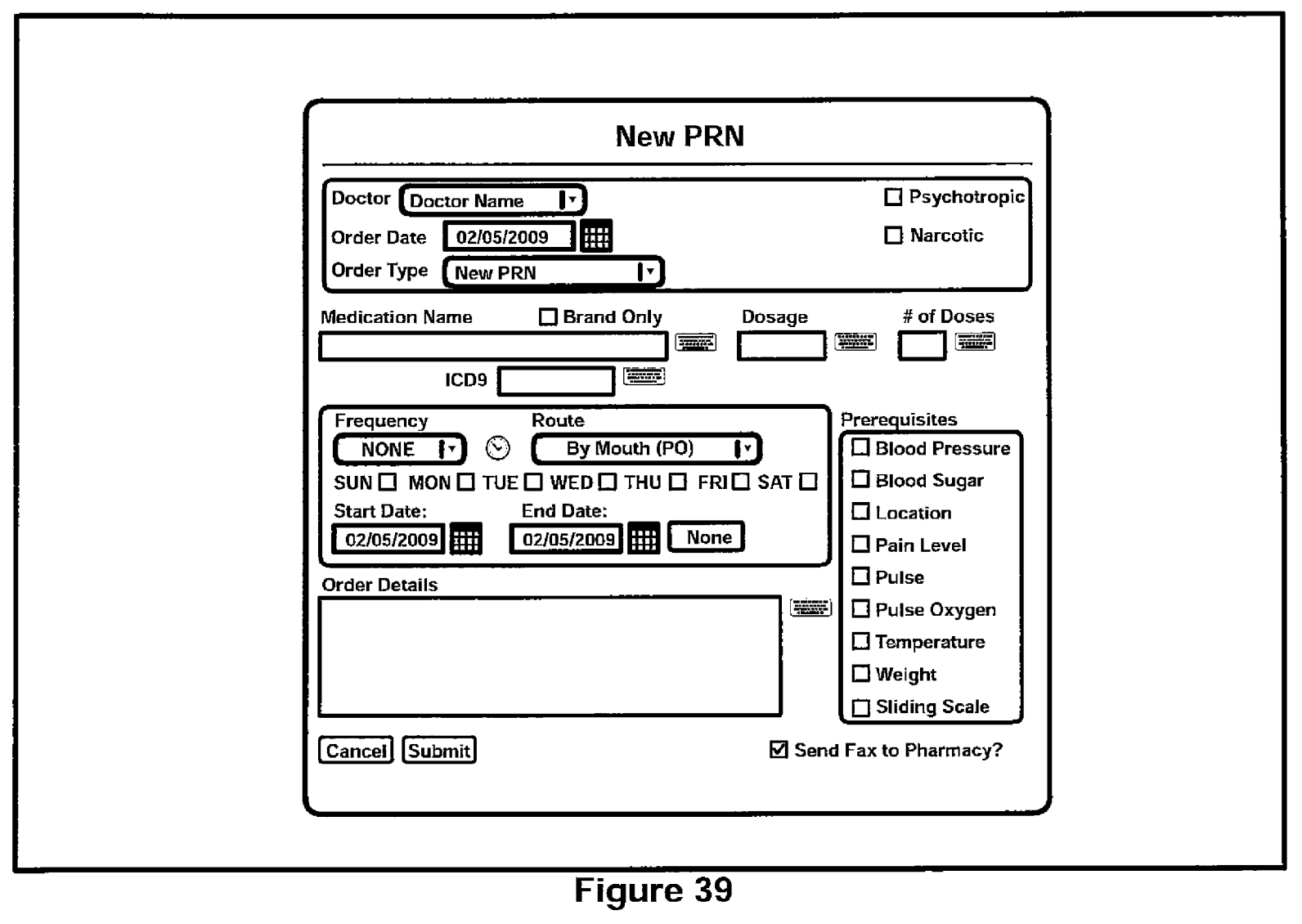
Figure 43:
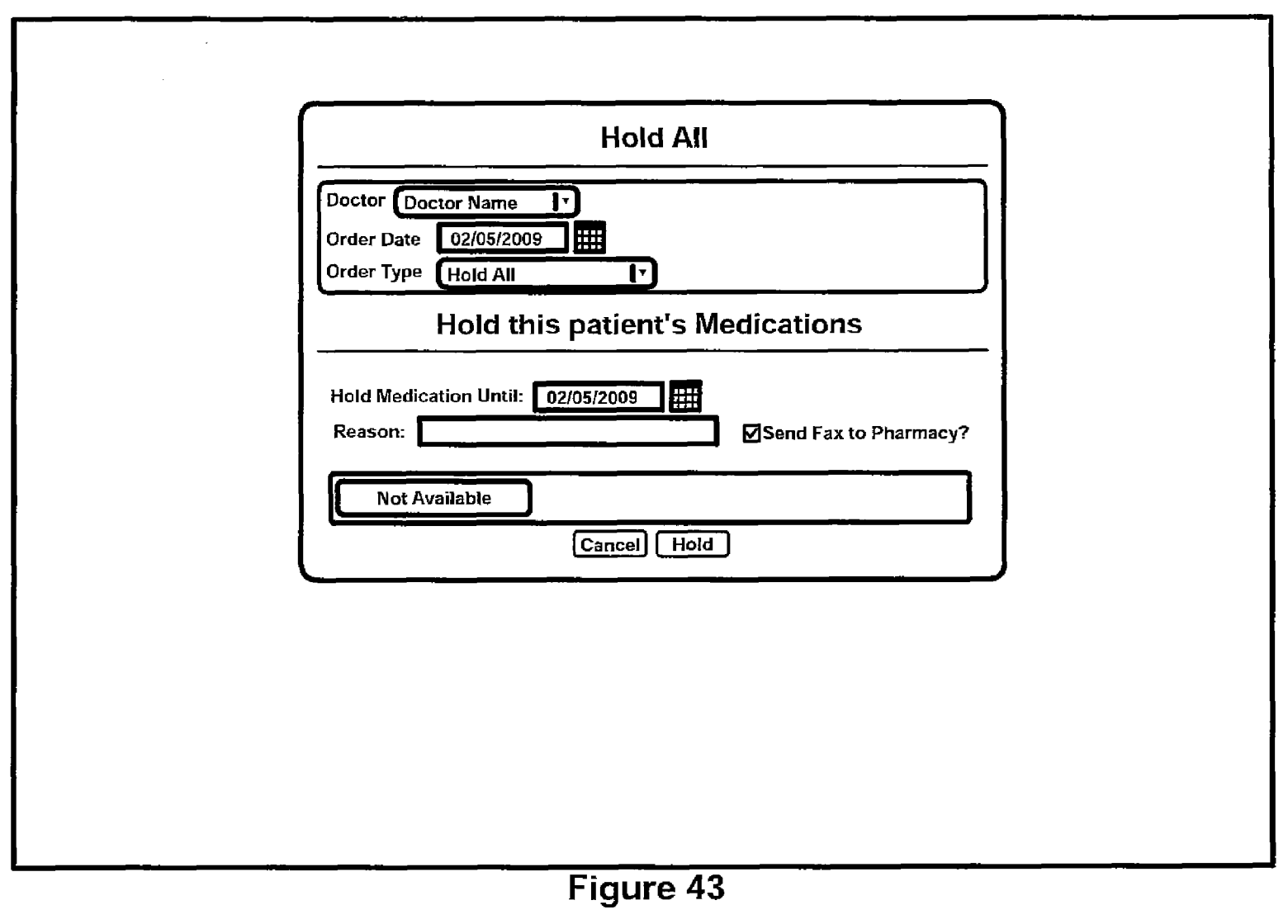
Figure 44:
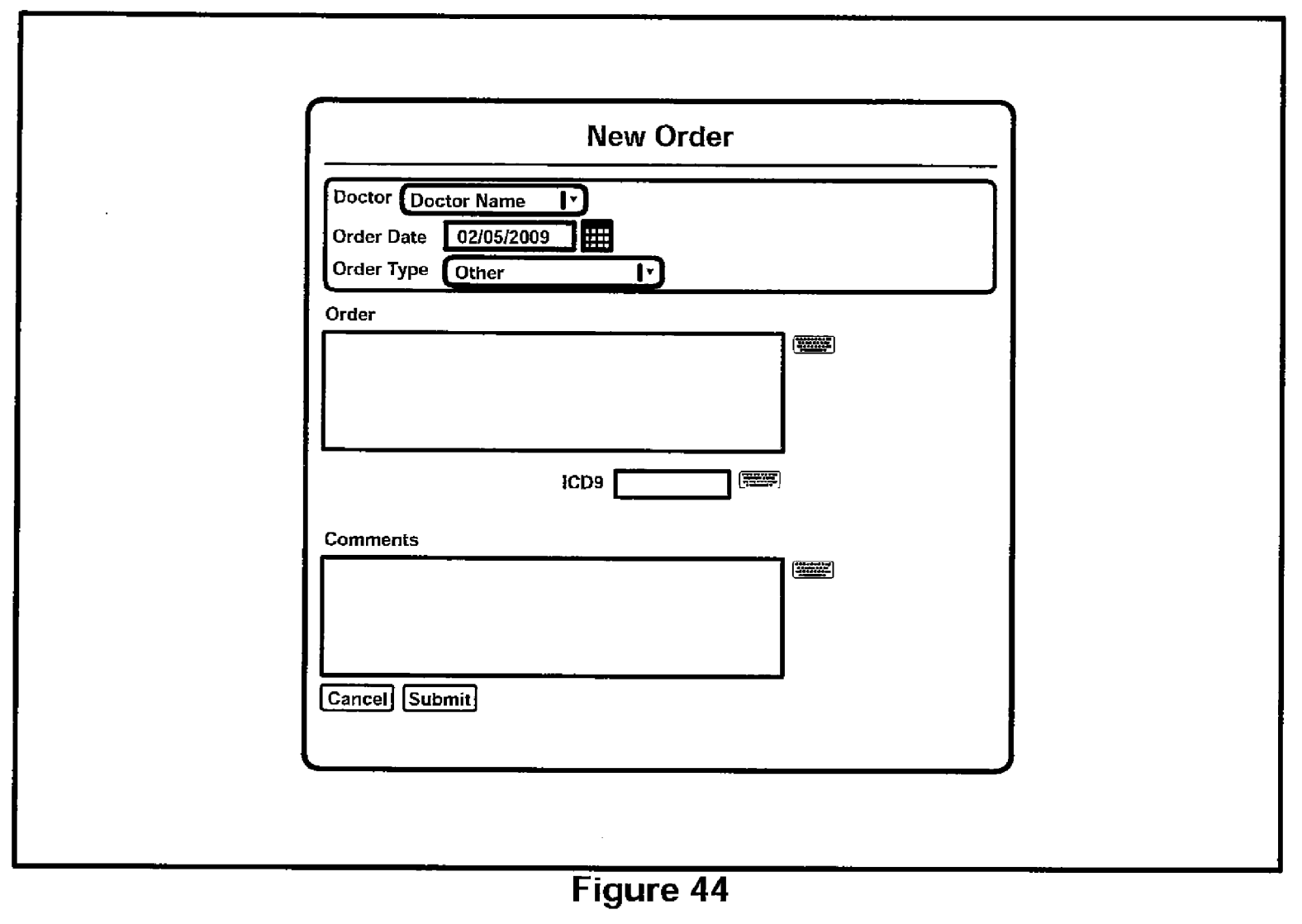

The new order screen (FIG. 37) enables a healthcare provider to enter any of several types of new orders including: new medications, new PRNs, new treatments, new scheduled procedures, D/C medications, D/C all medications, hold all medications, and a special "other" category for other types of orders not fitting into any of the categories. Initially, the new order screen contains a pulldown menu for selecting the doctor 97, a date field for selecting the date of the order 98, and a pulldown menu to select the type of order 99 (i.e., those types listed above). Once the healthcare provider selects an order type, the display changes to one of: new medication order screen (FIG. 38), new PRN order screen (FIG. 39), new treatment order screen (FIG. 40), new scheduled procedure screen (FIG. 41), D/C medication screen (FIG. 33), D/C all medications screen (FIG. 42), hold all screen (FIG. 43), and other order screen (FIG. 44). This enables the healthcare provider to enter the information specific to each order type and then submit the order. When the submit button is pressed, the order is checked to ensure that all required fields are filled in, and if so, the order is entered. Otherwise, an alert message is displayed informing the healthcare provider about missing information.

Figure 37:
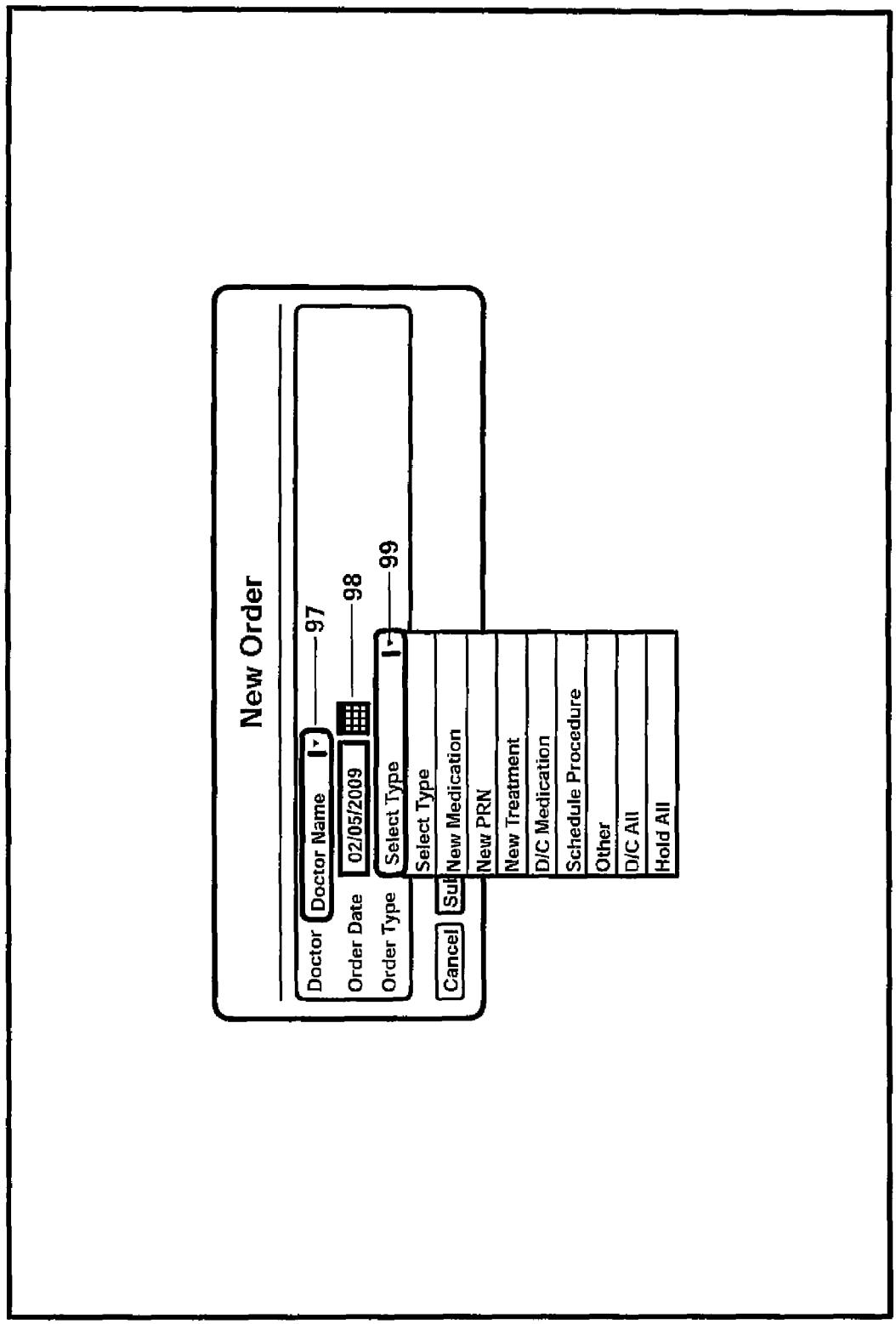
FIG. 37 is a screenshot of the new order screen.

The new order screen can be navigated to by clicking on the new order button on the orders screen (FIG. 37). In addition, the healthcare provider can click on the new medication icon on the routine medications needed (44 in FIG. 14) or PRNs available (84 on FIG. 18) screens. In these cases, a pulldown menu is displayed, allowing the healthcare provider to select medications from the ER box or to go directly to the new medication order screen. If the ER box is selected, submenus are shown in the pulldown menu, allowing the healthcare provider to pick a medication from the ER box. Then the new medication order screen is shown with the medication filled in. The healthcare provider then proceeds to include the other details of the order and submit.

The healthcare provider must include the medication name in the auto-completing text box 100. For convenience, as the healthcare provider begins typing the medication name, possible completions are shown in a pulldown menu. By default, the name of the medication displayed on the buttons on the routine medications needed and PRNs available screens (e.g., 83 on FIG. 18) show both the medication's brand and generic names. If the healthcare provider clicks the brand only box 109, only the brand will be shown.

The healthcare provider must also select the frequency of the medication 101. If a period frequency is selected, the periods of administration are the institution defaults for the frequency. If different periods are desired, the healthcare provider clicks on 102, and a popup is displayed, enabling the appropriate number of periods to be selected. If the healthcare provider checks any of the boxes for days of the week 103, then the medication will only be given on those days. If no days are checked, then the medication is given every day, unless the period prescribes that it should be given only every certain number of days (e.g., every three days). If the medication has prerequisites, this fact is indicated by checking the appropriate prerequisite boxes 104. If the medication name supplied is known to the cart station as a narcotic or a psychotropic, then the appropriate boxes 105 are automatically checked; otherwise, the healthcare provider can check the appropriate boxes to indicate that the medication is a psychotropic or a narcotic. The healthcare provider also chooses the route of administration of the medication by selecting from the pulldown menu 106.

The ICD9 box (110) enables the healthcare provider to input the ICD9 insurance code for the new order. This information is recorded along with the new order. Similar boxes are provided on many of the order screens.

If the healthcare provider clicks on the new treatment icon on the treatments needed section (FIG. 17), the new treatment screen (FIG. 40) will display. The healthcare provider fills in the required information as with the other order screens. The treatments appearing in the pulldown menu of possible treatments are defined for the institution on the administration web pages. A box is also provided for indicating that the treatment is PRN 112.

If the healthcare provider selects "schedule procedure" from the "select type" pulldown menu on the new order screen (FIG. 37), the new schedule procedure screen is displayed (FIG. 41). This screen is filled out similarly to the other order screens, except that the healthcare provider must choose which procedure is desired 113.

If "D/C medication" is selected from the pulldown menu on FIG. 37, the D/C medication screen (FIG. 33) is displayed, enabling the healthcare provider to discontinue one of the patient's medications. This screen requires the selection of the doctor ordering the discontinuation, the date of the discontinuation, the medication to be discontinued, comments associated with the order, and whether or not the D/C order should be faxed to the pharmacy. The "D/C all medications" selection on the new order screen (from the pulldown menu on FIG. 37) displays the D/C all medications screen (FIG. 42), which enables the healthcare provider, after supplying the same information as on the D/C medication screen, to discontinue all of a patient's medications. If "hold all" is selected on the new order screen (from the pulldown menu on FIG. 37), the hold all screen (FIG. 43) is displayed. Here, after supplying the ordering doctor, the order date, the hold until date, providing a reason for the hold, and selecting whether or not this order should be faxed to the pharmacy, the healthcare provider can hold all of a patient's medications. If "other order" is selected on the new order screen (from the pulldown menu on FIG. 37), the new other order screen (FIG. 44) is displayed. This screen is used to submit orders that do not fit into any of the categories discussed above. The information required on this screen is similar to the rest of the order screens, except that the healthcare provider simply includes the text and the comments of the order.

The insulin sliding scale screen (FIG. 45) enables a healthcare provider to enter information specifying how much insulin a patient should be given based on his or her blood sugar. The desired number of intervals can be defined by adding 114 or removing 115 intervals from this display. The range of each interval is set by sliding the indicators 116 on the scale. The number of units of insulin to be given for blood sugar values in each interval is set by clicking the appropriate minus 117 and plus 118 boxes.

Figure 71:
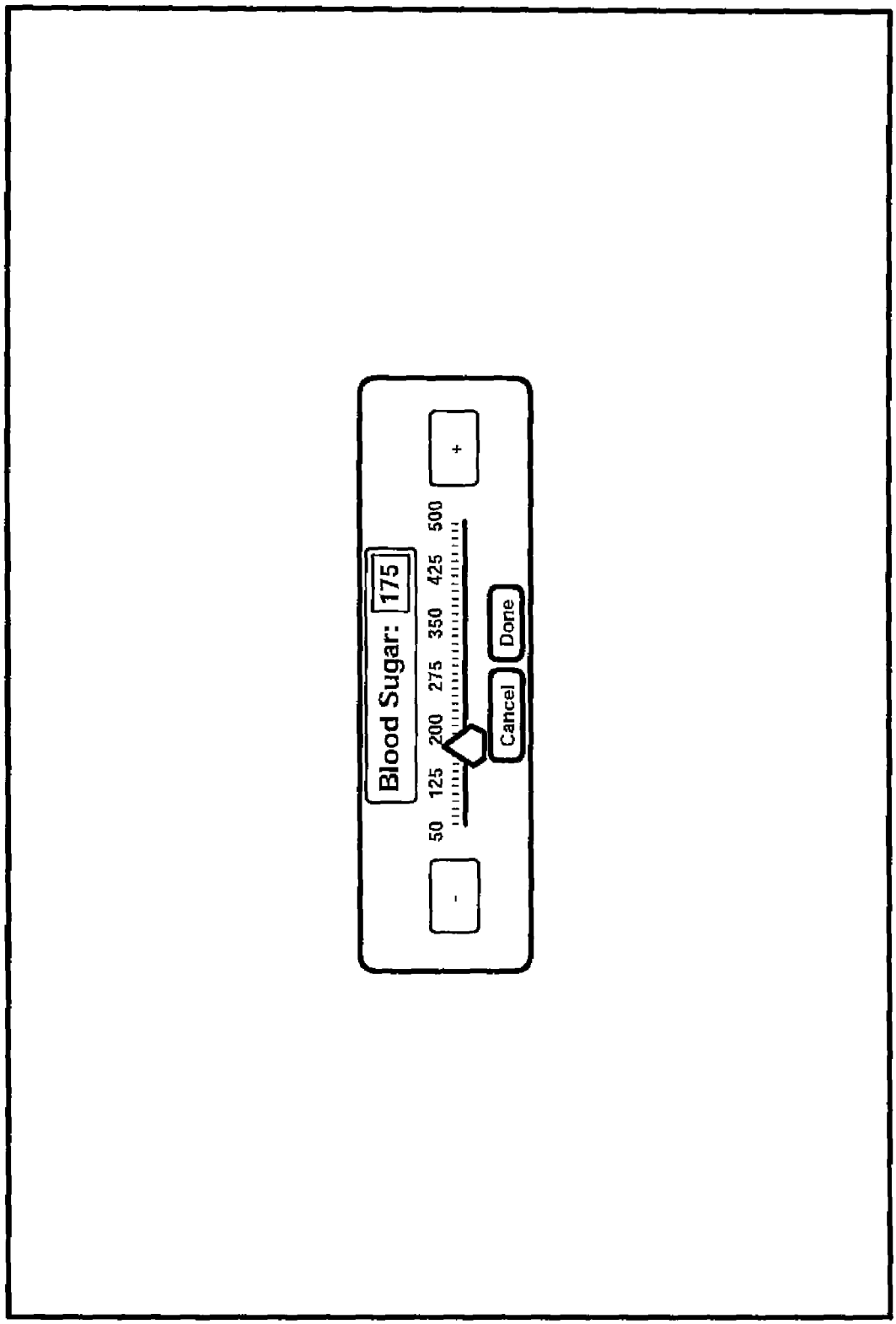
FIG. 71 is a screenshot of the blood sugar screen.

When insulin appears on the medications needed screen, it is automatically assigned a blood sugar prerequisite. The healthcare provider completes this prerequisite by measuring the patient's blood sugar and entering the value into a screen provided (FIG. 71). The values set for the insulin sliding scale are consulted, and if insulin is required, a message pops up telling the healthcare provider how many units to administer if insulin should be given. A patient's current insulin sliding scale is displayed on the medication profile screen (FIG. 13).

Figure 46:
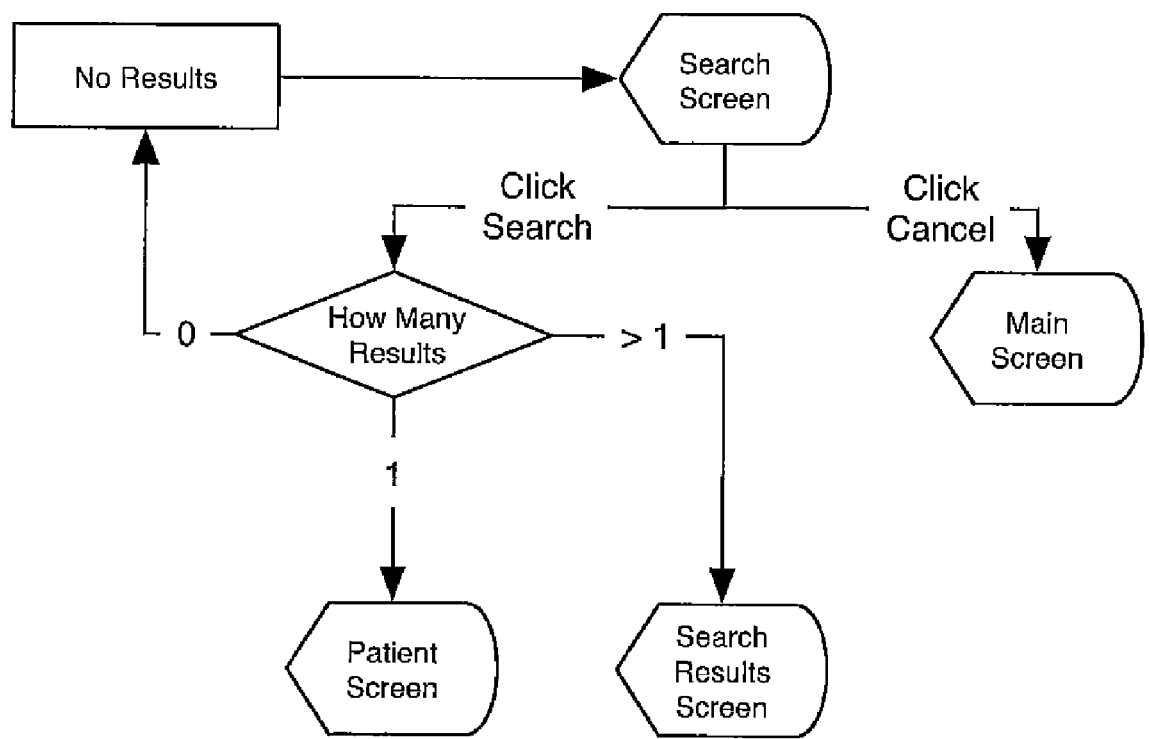
FIG. 46 is a diagram of the flow of the search screen.

If the search button is clicked on the main screen (20 on FIG. 10), the search screen (FIG. 47) is displayed. FIG. 46 shows a flow diagram of the search screen sequence. The healthcare provider can type a string of characters into the text box 119 provided and hit the search button. In response, a search results screen is displayed that is similar to the nurse main screen, except that it shows only the patients whose name or room number contains the typed text string. The healthcare provider can click on any of the patients in this display, and the patient screen (FIG. 14) will be displayed for that patient. If the result of the search is a single patient, the patient screen for that patient is displayed directly. If there are no results from the search, an alert to that effect is displayed.

Figure 48:
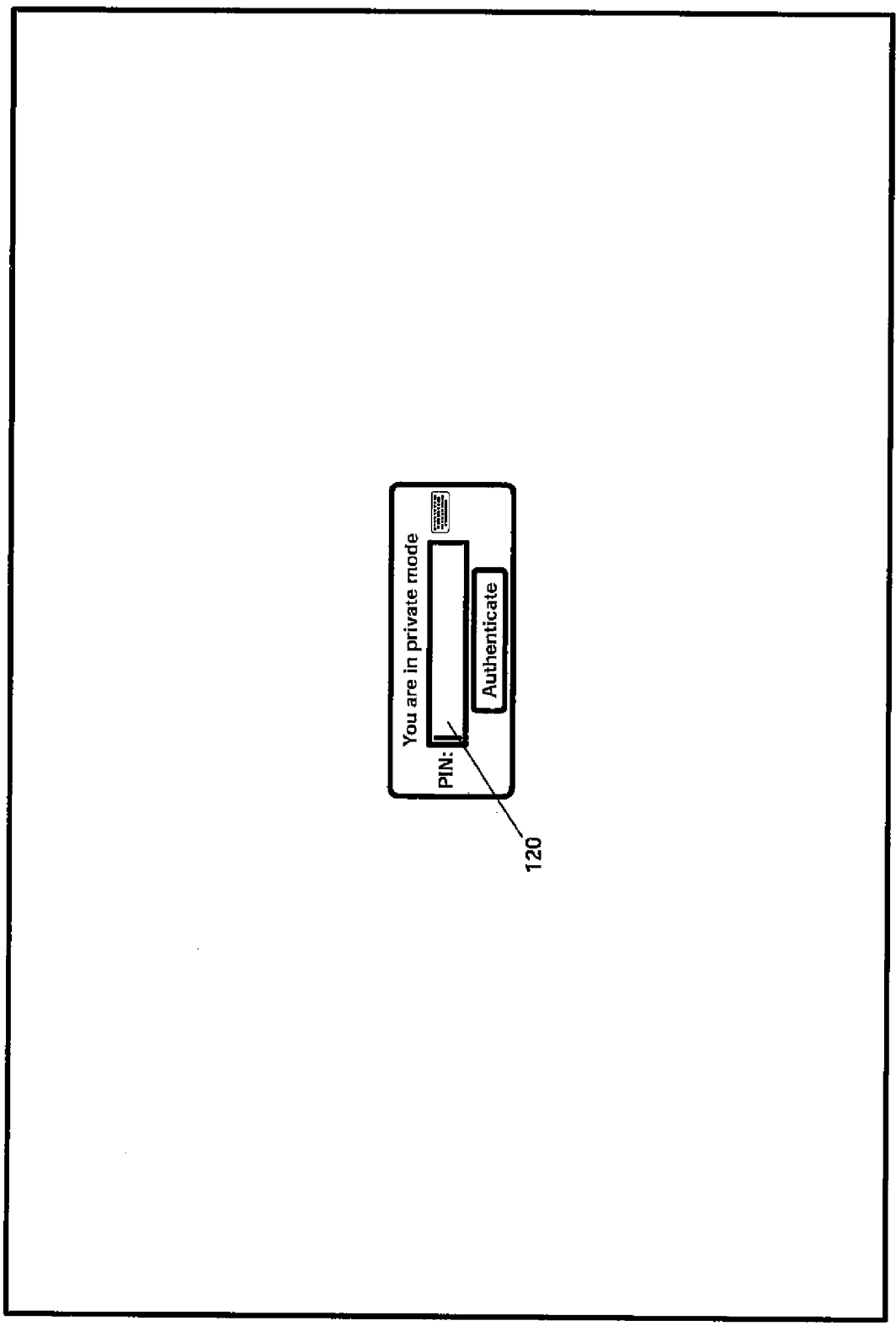
FIG. 48 is a screenshot of the private mode screen.
Figure 49:
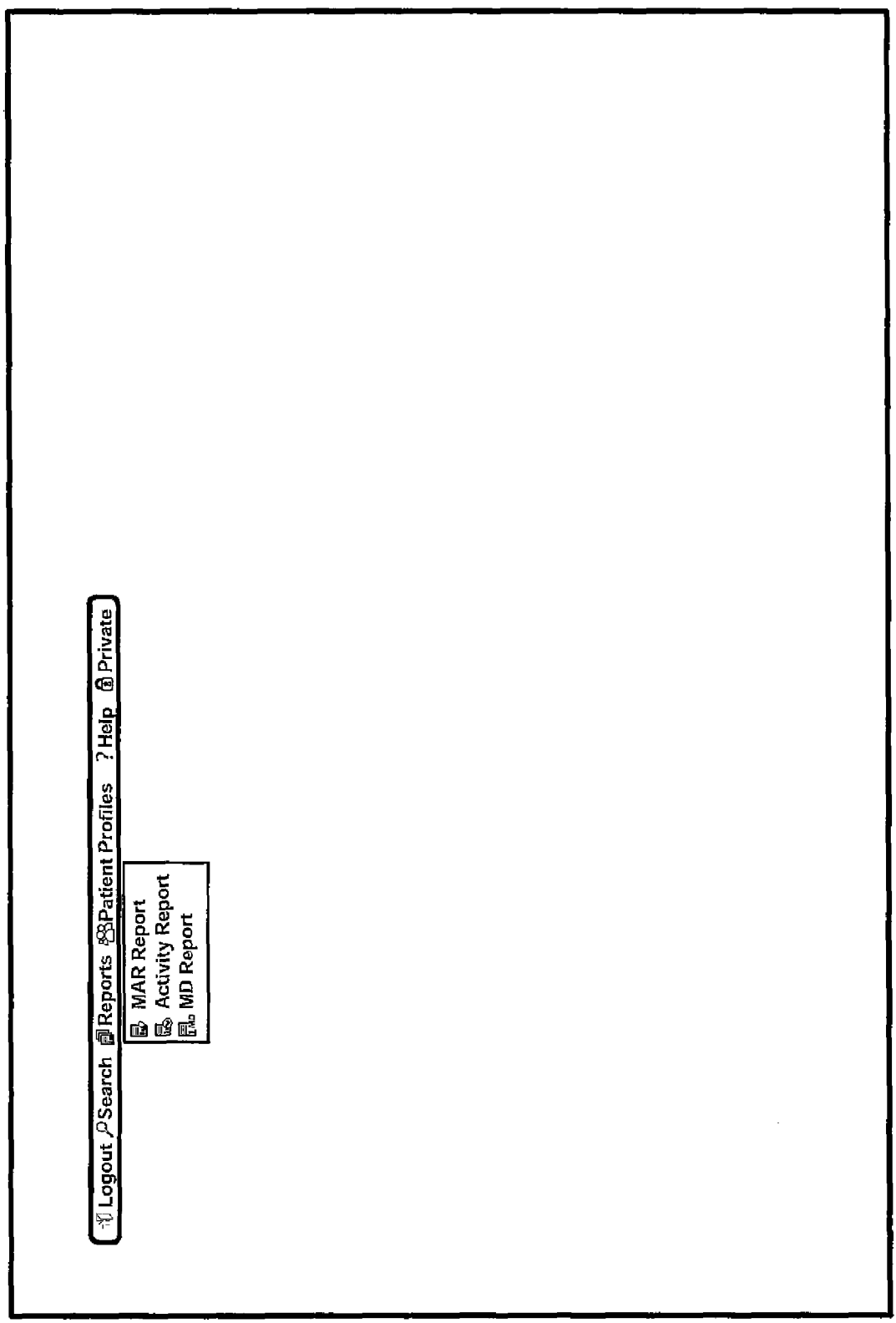
FIG. 49 is a screenshot of the reports pulldown menu.

After an institution-defined period of non-activity on the cart station or when the private mode button 23 on FIG. 10 is clicked, the cart station enters private mode, displaying FIG. 48. To leave private mode and resume normal operation, the healthcare provider must type his or her PIN into the text box 120 provided, and if the institution requires fingerprint scans, he or she must also scan his or her fingerprint.

When the reports button 21 on FIG. 10 is clicked, a pulldown menu (FIG. 49) appears, where the healthcare provider can select from MAR report, activity report, and MD report. A MAR report describes all activities on patients over a specified period of time, including vital signs recorded, procedures given, procedures not given, postponements, and medication errors. For each of these events, the time and healthcare provider are displayed. If a procedure is not given, a reason is displayed. As noted above, MAR reports are required by regulatory agencies.

Figure 50:
FIG. 50 is a screenshot of an exemplary medication administration report.
Figure 51:
FIG. 51 is a screenshot of an exemplary activity report.
Figure 52:
FIG. 52 is a screenshot of an exemplary MD report.

An activity report displays information similar to the MAR report, except that it displays this information for a particular healthcare provider. This report is used by the healthcare provider to report activities mainly at shift changes. An MD report is sent with patients when they go to appointments with physicians. This report includes all prescribed medications, a small number of the most recent vital signs taken, and medications given. Examples of the three types of reports described above are shown in FIGS. 50-52, respectively.

Figure 53:
FIG. 53 is a screenshot of the patient details basic info screen.
Figure 54:
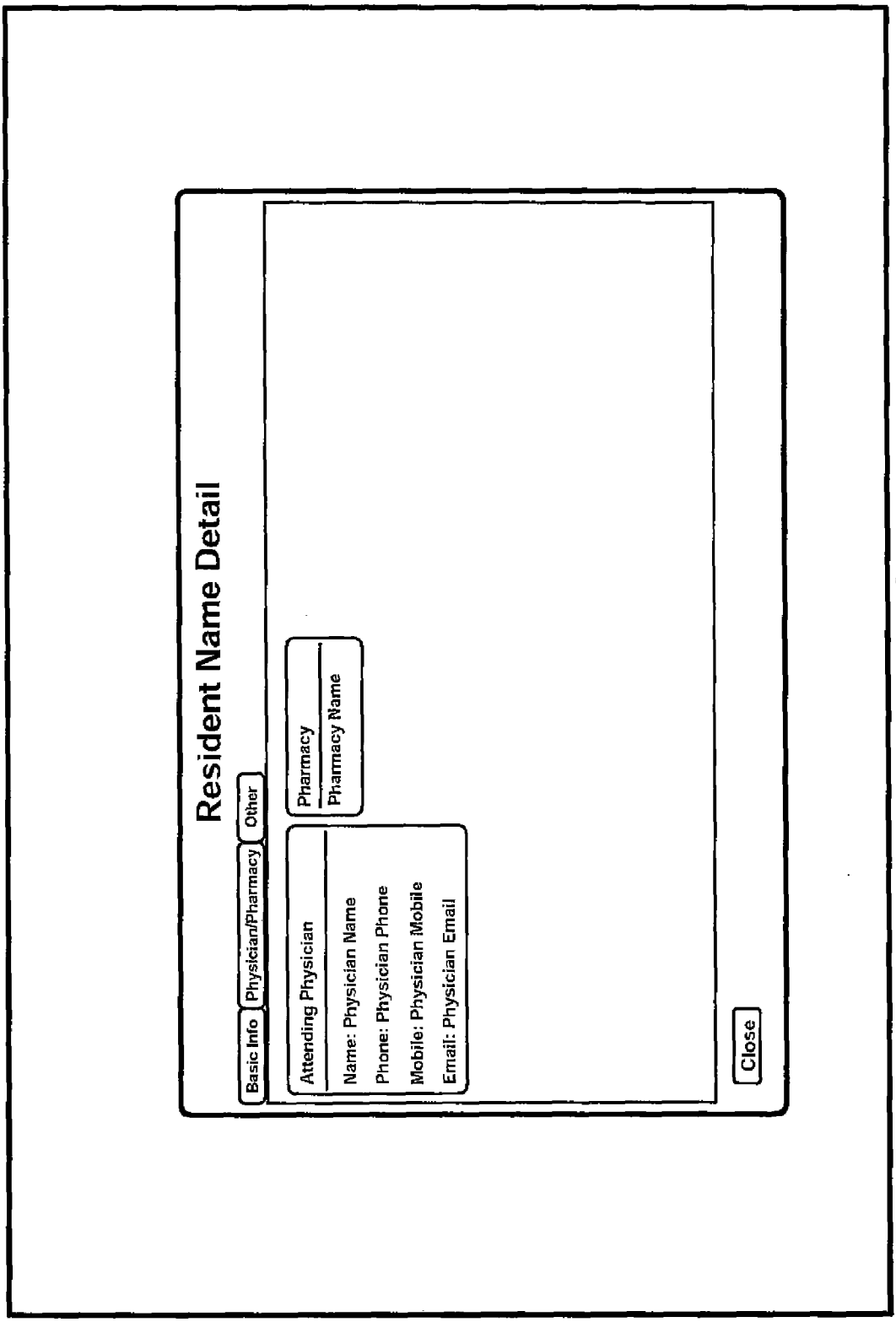
FIG. 54 is a screenshot of the patient details physician/pharmacy screen.

When the patient details button is clicked on the patient screen 34 on FIG. 14, the patient details screen (FIG. 53) is displayed. This is divided by tabs into basic info (FIG. 53), physician/pharmacy details (FIG. 54), and other (FIG. 55). Basic information includes name, room, date of birth, age, gender, weight, height, civil status, Social Security number, admission date, where the patient was admitted from, home address, emergency contact, and directives. Physician/pharmacy details includes information on the patient's physician and pharmacy. Other information includes medical record number, Medicare number, Medicaid number, insurance information, insurance contact, diet restrictions, admission notes, allergies, and diagnosis.

Figure 56:
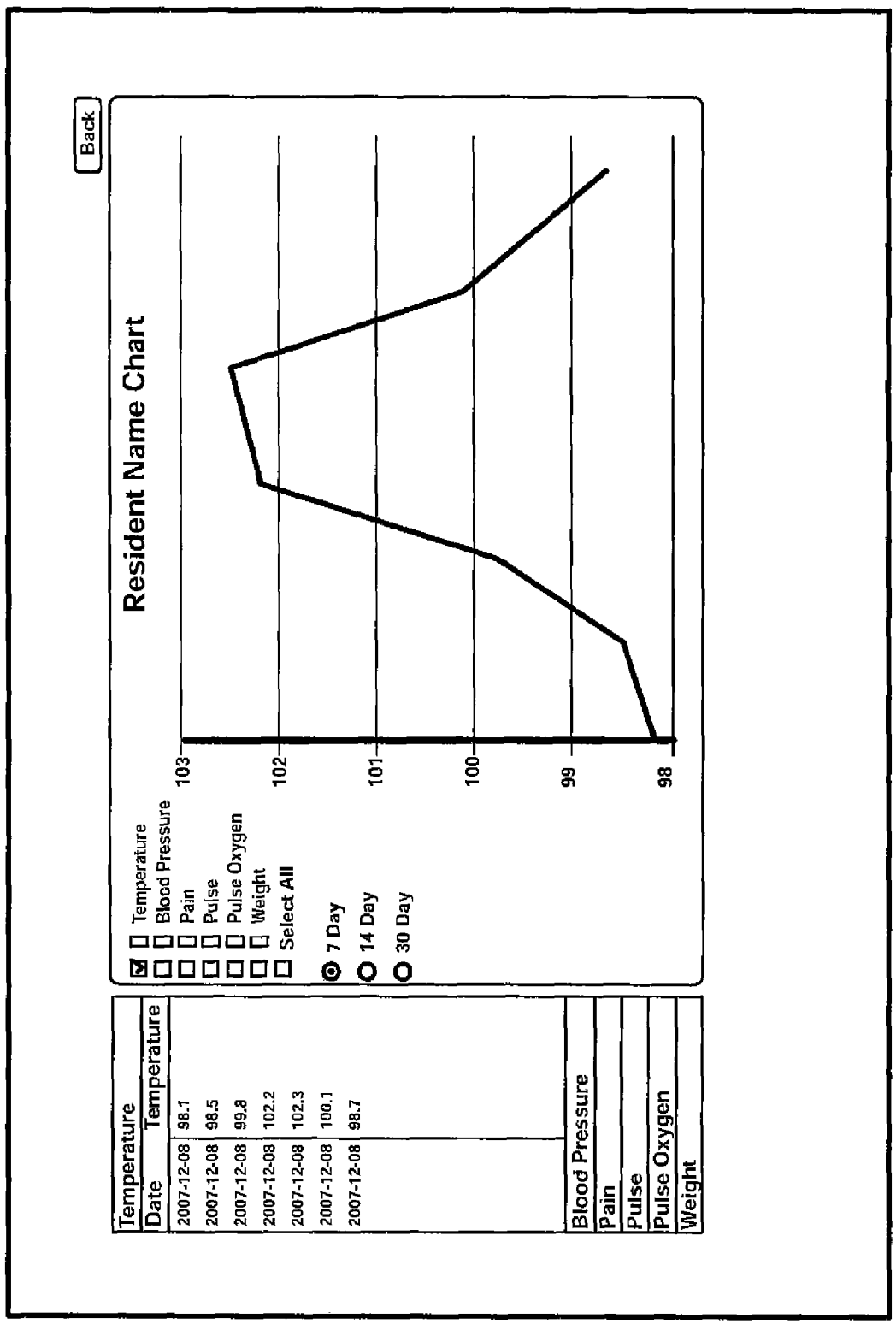
FIG. 56 is a screenshot of the chart screen.

By clicking on the cart icon 38 on the patient screen (FIG. 14), the healthcare provider can display charts of a patient's historical vitals data. An example of the cart screen is shown in FIG. 56. By clicking on the checkboxes, charts of any combination of a patient's vitals can be displayed. The charts of different vitals are distinguished by color coding, e.g., the chart of a patient's daily temperatures is colored orange. By clicking on the radio buttons, data for the last 7, 14, or 30 days on which data was recorded can be displayed. The screen also shows tables of the vitals data.

D. The Healthcare Server

The healthcare server is housed in a secure off-site facility running the synchronization software of the present invention. It maintains accurate and timely data for all institutions that use the present invention. The Internet is a convenient world-wide network, but it is often unreliable ("the Internet is down"), has limited bandwidth (local area networks have tens or hundreds of times the capacity of even fast Internet connections), and suffers from high latency (as data packets may be routed around the world). These factors vastly complicate the communication protocols, as well as the applications that rely on them.

The cart stations and the healthcare server need access to common data, such as the medications required by certain patients or the medications given to patients on a specific day. Because communication with the server is not guaranteed to be available at all times, the information in the cart station and in the healthcare server needs to be synchronized. The present invention synchronizes whenever the care provider logs into or out of the cart station, whenever the care provider clicks on the "synchronize now" button on the cart station (19 on FIG. 10), or whenever the cart station is idle for an institution-defined period of time.

E. Synchronization

Traditional syncing algorithms, such as the ones that synchronize contact and calendar data between desktop applications and hand-held devices, operate by keeping track of changes between the different devices. Existing general-purpose sync operations between a client and a server consider (1) the data currently in the client, (2) the data currently in the server, and (3) the data in the client and server the last time a sync operation was performed. Maintaining this third data set is a significant overhead of syncing because it implies that a copy of the data must be kept for each client that connects to the server. And if this copy is misplaced or damaged, the client will be unable to sync properly. Typical errors include duplicate entries in the client, lost modifications, and even lost entries. Consequently, a major portion of prior art synchronization algorithms relates to maintaining the integrity of these copies, even while other clients attempt to sync to the server. This is achieved by preventing simultaneous access to certain portions of the syncing algorithm, so-called critical regions of the algorithm. Obviously, the larger the critical region, the fewer clients that can connect to the host within a given period of time, i.e., having a large critical region in the syncing algorithm limits the scalability of the algorithm.

The present invention's syncing algorithm minimizes this problem by considering only the data currently in the cart station's database and the data currently in the healthcare server. A database is comprised of tables, which in turn are comprised of records. A record is a single piece of information such as a patient or a medication. These records are annotated with timestamps that mark the last time a sync operation was performed on the records. The algorithm syncs the data using these timestamps, requiring only a single line in the critical section of code-the line that increments the server's timestamp. Thus, the algorithm is scalable to hundreds of thousands of cart stations per server.

This algorithm, however, is special purpose because it exploits the fact that duplicate processing of updates is harmless. One of the consequences of having such a small critical region of code is that it is possible, when two cart stations attempt to sync at the same time, to end up with non-consecutive timestamps. The result is that some updates may be processed more than once in either the client cart station or the server.

Figure 5:
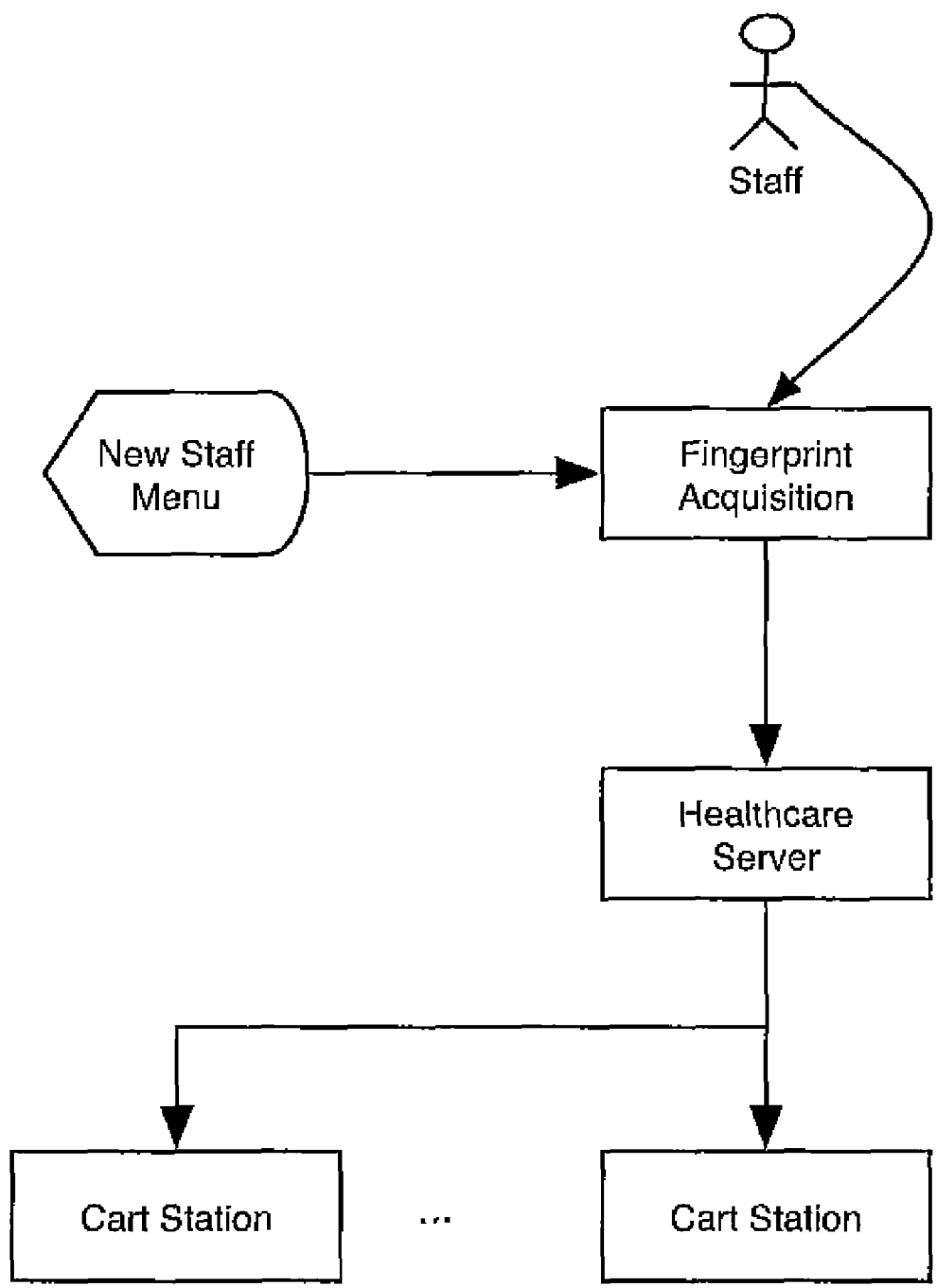
FIG. 5 is a diagram illustrating how fingerprint files are distributed to multiple cart stations.

The flexibility of the syncing algorithm can be demonstrated by the present invention's treatment of fingerprint acquisition for new employees. Entry of a new employee at an institution that uses fingerprint authentication requires the employee to provide their fingerprint for subsequent authentication. The present invention enables the fingerprint acquisition on any institution cart station. A natural property of the sync algorithm is that the acquired fingerprint file will automatically be uploaded to the healthcare server and distributed to the other cart stations of the institution, enabling the employee to login to all of the cart stations after a single acquisition, see FIG. 5 for a graphical depiction of this process.

The synchronization sequence is used to move records from the healthcare server to the cart stations and vice versa. The sequence is divided into three main phases. First, the cart station collects the data that needs to be sent and ships it to the healthcare server. Second, the healthcare server processes the station's data and determines what new data must be sent to the station. Since multiple stations may be accessing the healthcare server at the same time, it is important that this second phase be as scalable as possible. Third, the cart station receives the data from the healthcare server and incorporates it into its database.

These phases are described in the accompanying diagrams, and the details are discussed below.

1. Phase 1: Preparation of Cart Station for Synchronization

Each cart station is identified by a unique ID. This ID is used by the server to keep track of which records are relevant to the client, e.g., which patients a particular cart station serves.

The cart station maintains several dozen tables that need to be kept in sync with the healthcare server. Much of the data in these tables comes originally from the healthcare server, e.g., the list of patients that the cart serves. The data is input either from the pharmacy or through the administration web pages. And some of the data is collected at the cart station, e.g., a record of drug administrations.

In addition to the timestamp on each record, each table also has a timestamp, which is an integer that encodes the last time that the particular table was synchronized with the server. What the cart station ensures is that it has appropriately updated all data received from the server up to that timestamp and that it has sent the server any records whose timestamp is greater than the table timestamp. (If the station needs to receive a complete refresh of the data, it can perform a synchronization with a zero timestamp.) Note that the synchronization time of one table may be different than the synchronization time of another table because all tables do not need to be updated at once.

Figure 6A:
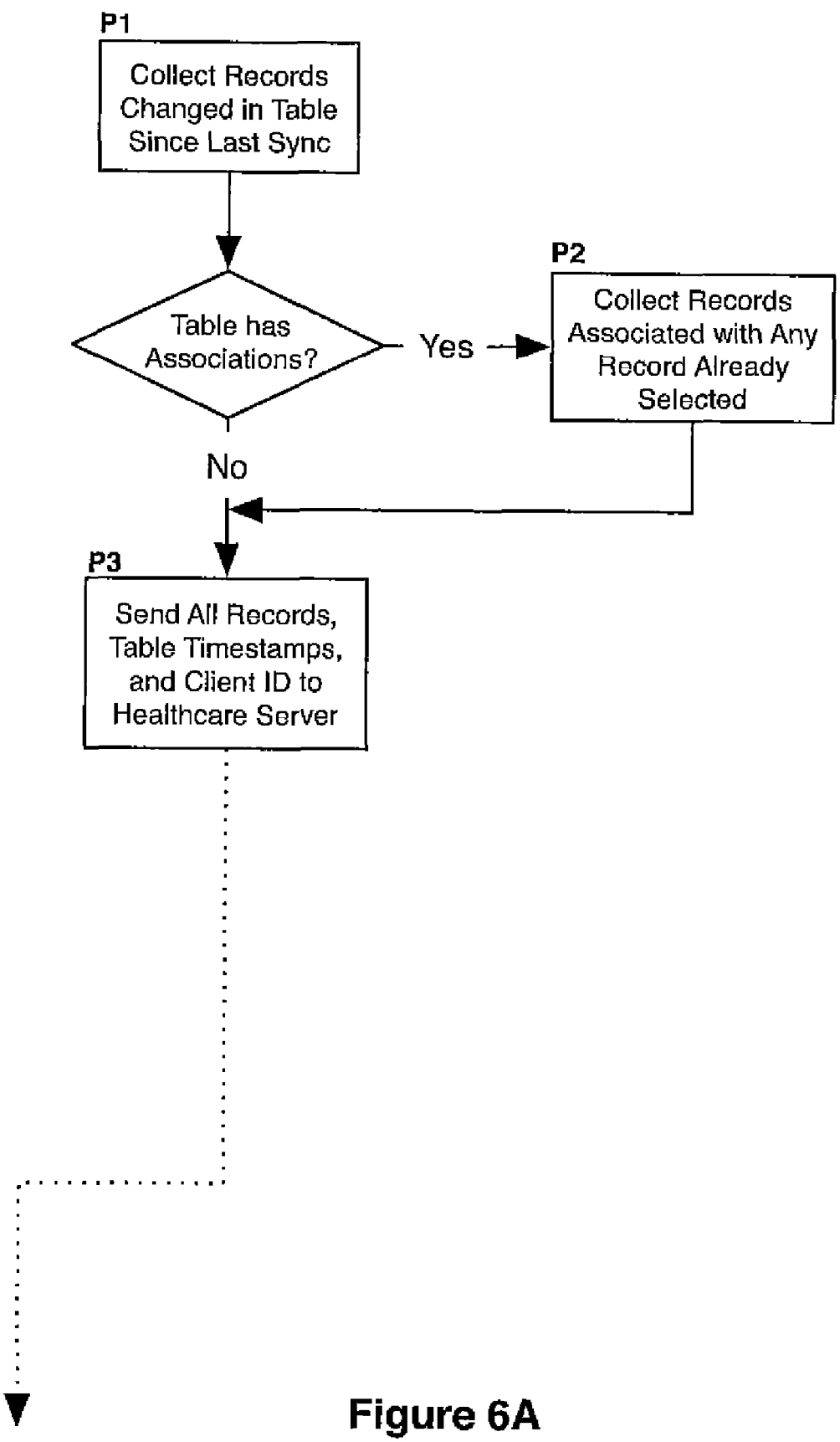
FIG. 6A is a diagram of the first phase of synchronization.

The records of some tables, however, need to be updated together because they contain related records. For example, one table reflects the procedures (such as a medication) that a patient should receive. Another table describes the details of this procedure, such as the actual medication, dosage, special instructions, etc. The related records of these two tables should be updated together to ensure that all instructions for a particular medication are received prior to dispensing medication. Tables with such records are referred to as associated tables, and the synchronization algorithm treats them specially by synchronizing all related records of associated tables in a single call, as seen in the algorithm presented below. This first phase of synchronization is shown in FIG. 6A.

Step P1 is the starting place for the synchronization process. Each record in the database is marked with a timestamp so that the cart station can easily and quickly determine which records have been inserted or modified in the cart station since the last time this particular table was synchronized with the server. (Note that this makes use of the timestamp kept on a per-table basis.) These records may be processed as necessary to convert them into the format shared with the server. For example, the cart station may precompute some values to speed up its recurring computations, such as the plan builder; however, such values are completely redundant because they can be calculated from the other values in the cart station's database. These redundant values do not need to be stored in the server because they can be recomputed any time they are required.

Step P2 is performed only if the table that is being synchronized also has associated tables. In this case, the cart station's database is consulted to find any records in those associated tables that are related to the records that have been selected to send to the server. Note that all related records of associated tables will be sent to the server, as opposed to just the most recently updated records. This ensures that the server and the stations perform updates to associated tables transactionally so that no details related to a procedure are ever lost.

At step P3, once the data is collected, it is sent to the healthcare server. This is accomplished via a secure communication channel, using point-to-point encryption, as well as secure http. The actual data is encoded using web services, in accordance with a pre-generated web service description language (WSDL) specification.

2. Phase 2: Synchronization of the Healthcare Server

The server maintains copies of all the stations' data, as well as other information that is never sent to the cart stations but is used merely to support the server's processing. For example, the server maintains a table of registered cart stations, which includes each cart station's unique ID, as well as the facility to which the cart station belongs, the patients served by the facility, etc.

The server also keeps a global timestamp, which is used as the official notion of time (as far as synchronization is concerned) for the server and all the stations. Each record of each table is also annotated with a timestamp, marking the value of the server timestamp on the last time that record was modified, whether it was modified by a synchronization operation, the administration web pages, or through an update from the pharmacy.

Figure 6B:
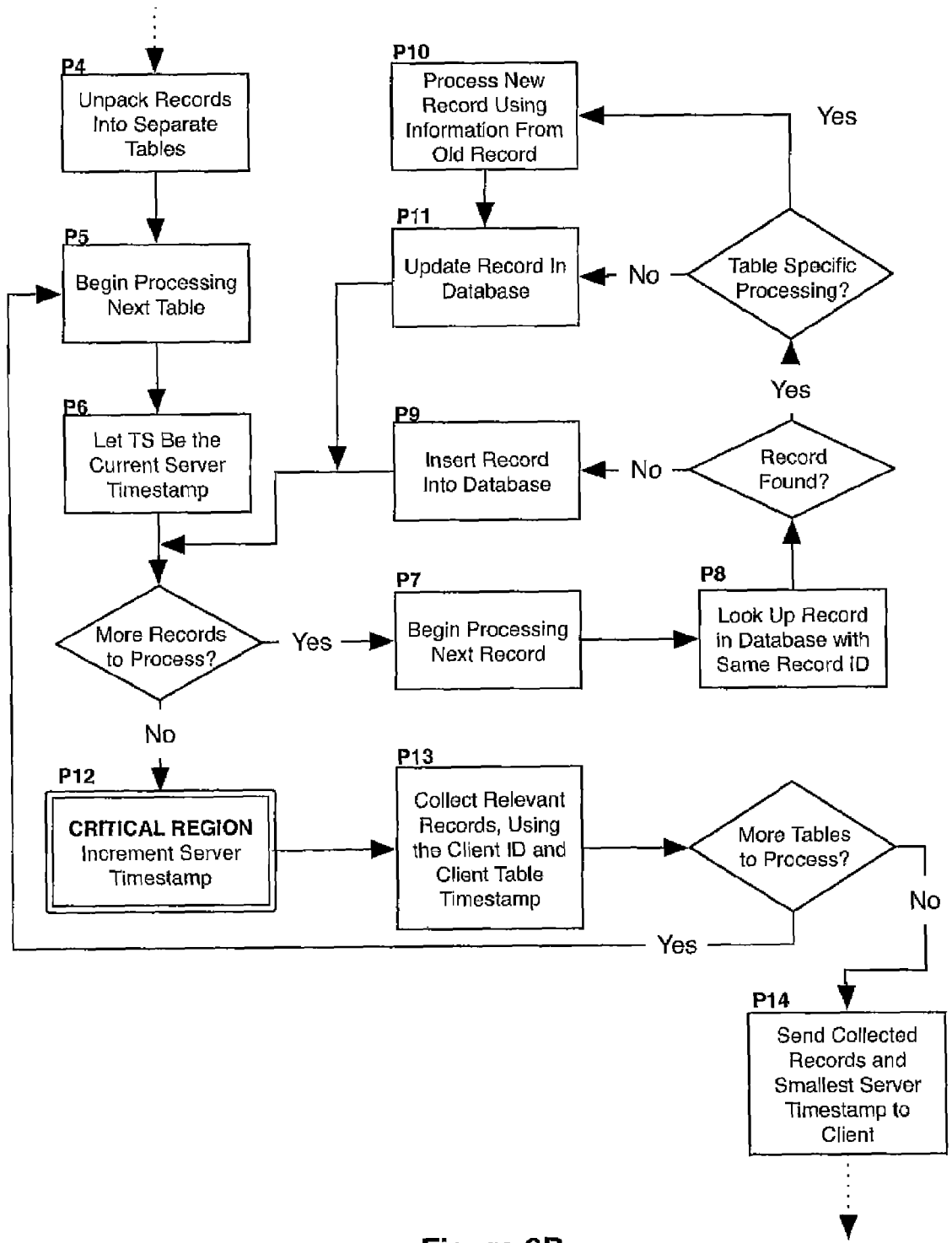
FIG. 6B is a diagram of the second phase of synchronization.

The key challenge faced by the server is supporting multiple cart stations simultaneously. This amount of concurrency is critical to supporting a large installed base of users; however, the concurrency is limited by the amount of server code that needs to be executed in isolation. This section of code is called the "critical region" of the algorithm, and it is the nature of critical regions that only one process may be executing the critical section at a time. This phase of synchronization is shown in FIG. 6B.

Step P4 marks the beginning of the synchronization phase from the perspective of the server. Recall that the cart station sends records from one or more tables (in the case of associated tables). The server unpacks these records into their separate, constituent tables. Then it proceeds to update each table on the server side.

At step P5, the synchronization algorithm proceeds by synchronizing one table at a time. This step simply selects the current table to update, which may be either the main table that is being synchronized in this request or one of its associated tables. At step P6, the system simply requests the current value of the server timestamp. This information will be used to mark all records that are updated as part of the current synchronization sequence. Note that the server timestamp is a global value, but it can be read independently of any other synchronization operations that may be happening simultaneously. This step does not require locking of the data and is not part of the critical region. At step P7, the system simply selects the next record received from the cart station so that it can process that record.

Each record is assigned a globally unique identifier. At step P8, the system looks up records in the tables of the healthcare server's database with the same record ID. Because this identifier is global, it can be used to find the record in the server or any of the cart stations. In this manner, the server can easily determine if the record sent from the cart station is a new record or an existing record in its own database.

Step P9 is performed when the record received from the cart station is not already on the healthcare server's database. In this case, the record is simply inserted into the database. Recall that each record has a timestamp associated with it. This timestamp is set to the current server timestamp, retrieved in step P6.

Step P10 is performed when the record received from the cart station is not already on the database and the table to which the record belongs defines specific record processing. The processing involves setting fields in the record that may not be available to the cart stations. For example, the record on the server may contain information that should only be viewed by DONs. Naturally, this information is not sent to the cart stations during a synchronization operation, nor does the cart station update this information; however, when the cart station performs all update on the record, the server must take steps to preserve the value of this extra information. This is precisely the function performed during this step. Each table can register custom processing steps that merge information from an existing record in the server with the updated record from the cart station. These custom steps, if declared for the table being updated, will be called during this step.

Step P11 is performed when the record received from the cart station is already on the database. At this point, the record from the cart station has been processed by any custom processing steps defined for the table. The existing record in the healthcare server's database is then updated to match the (possibly modified) record from the cart station.

Step P12 is the only step in the critical region of code; that is, this is the only step that cannot be performed simultaneously by more than one synchronization operation at a time. Thus, this is the only step that can limit the scalability of the synchronization algorithm. The step consists of only one line, namely, incrementing the server's idea of the timestamp. Note that the new value of the timestamp is not necessarily one more than the timestamp retrieved during step P6. The reason for this is that other synchronization processes that may have occurred simultaneously may have already incremented the timestamp.

During step P13, the server determines which records need to be sent to the cart station. There are two different aspects that are taken into consideration at this step. First, the cart station only receives data that is relevant to the patients it is assigned to treat. The server determines which data this is based on the ID provided by the cart station. This ID uniquely identifies a specific cart station at a facility, and the server can use this information to find the facility rooms that are serviced by this cart station, the patients assigned to those rooms, and the medications, treatments, etc., that those patients should receive. Second, the cart station only receives data that has been modified since the last synchronization sequence. This is determined by using the timestamp provided by the cart station. Essentially, the server selects any relevant records whose record timestamp exceeds the cart station's timestamp.

Note that it is impossible for the server to distinguish records that have a high timestamp but that are nevertheless known to the cart station. For example, all records sent by the cart station during the current synchronization operation have a timestamp that may be larger than the cart station's timestamp. This will certainly happen, for example, when another cart station synchronizes with the server. These records will then be sent to the cart station as part of the result; however, this does not result in duplicate records in the cart station because each record has a globally unique ID, which the cart station can use to determine whether it is a new record or an update to an existing record.

The final step (P14) in the server's synchronization sequence is to send the relevant records back to the cart station. These records are packaged together and sent back using the same WSDL described in step P3. The server also sends the current server timestamp to the cart station. This is the timestamp selected in step P6; however, since the server may have updated multiple tables as part of this request, only the smallest timestamp is sent. This is the only value that the server can guarantee meets the cart station's invariant, namely, that the cart station knows all relevant records since the timestamp it associates with a table. The result may be that some records will be sent to the cart station multiple times, but as noted in the discussion of step P13, the algorithm works correctly even if records are sent multiple times.

3. Phase 3: Completion of Cart Station Synchronization

Figure 6C:
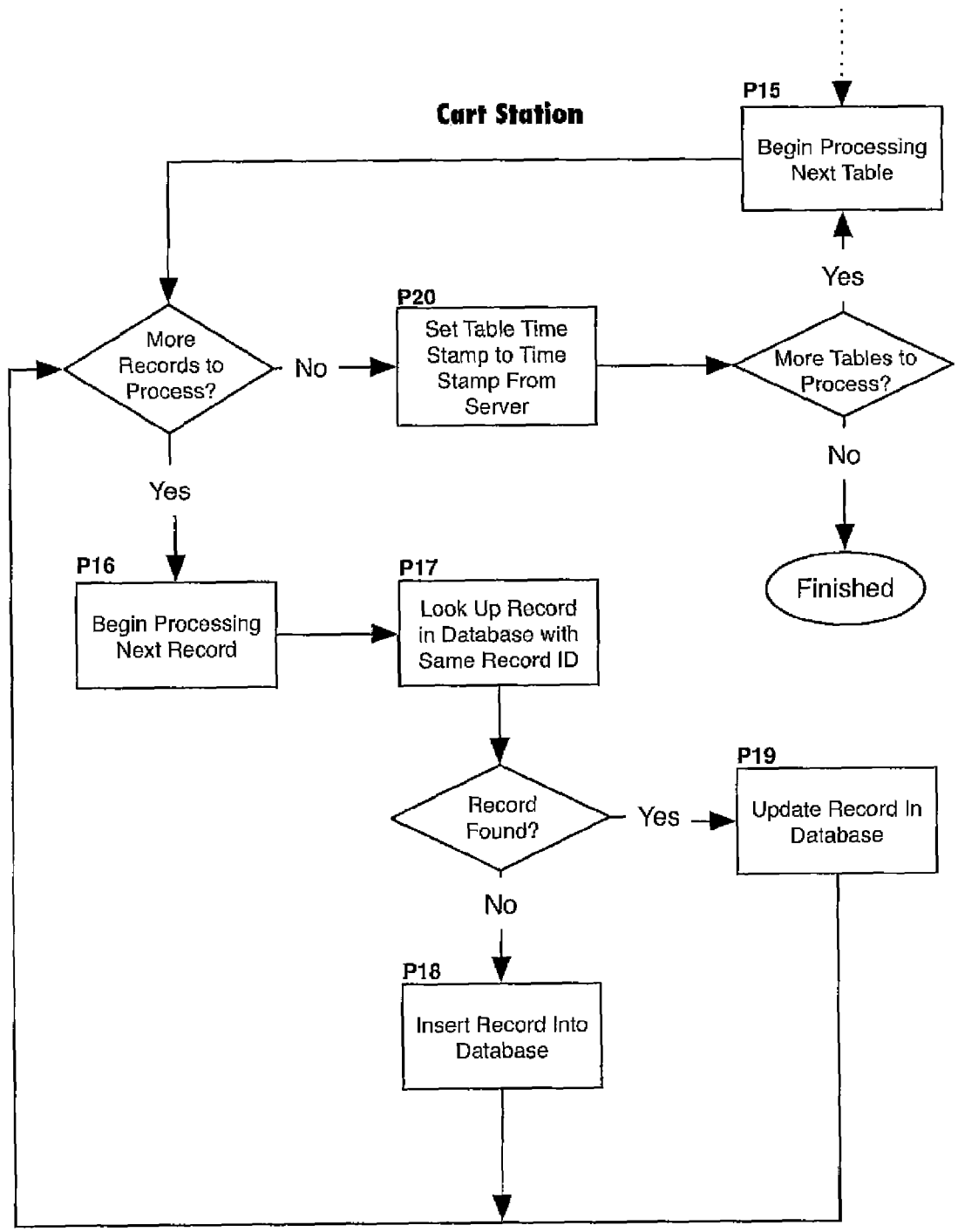
FIG. 6C is a diagram of the third phase of synchronization.

After sending new or modified records to the server, the cart station waited while the server processed the records and determined which records to send to the cart station for insertion. Once the server finishes its response, the cart station stores any new or modified records from the server into its database. The steps performed are very similar to the server's processing. FIG. 6C shows this sequence.

At step P15, the cart station processes the server's response one table at a time. This step simply selects the next table that should be processed, which will be either the main table being synchronized or one of its associated tables. At step P16, the cart station processes one record at a time; this step simply selects the next record from the current table to process.

At step P17, the cart station simply searches its database to see if there is already a record with the given ID. Recall that each record has a globally unique identifier. If so, the server has sent an update to an existing record. If not, this is the first time the cart station has seen this particular record, so it should be inserted into its database. At step P18, the record is inserted into the cart station's database if it is not already found there. At step P19, the record in the database is updated to match the information provided by the server.

At step P20, the timestamp associated with the current table is updated. Recall that the cart station keeps a timestamp for each table that it stores. This value, which is sent by the server in step P14, is now stored by the cart station, and it will be used in the next iteration of the synchronization operation in step P1.

The synchronization algorithms for the cart station and healthcare server are presented in detail below:

Cart Station Synchronization Algorithm:
  Input:
    MainTable—the table to update
    MainTable.timestamp—the last time MainTable was synchronized
    ClientID—unique ID of cart station
  Local Variables:
    ModRecords—Array of records in MainTable (and associated tables) that have been modified locally since the last sync
    AssocTables—other database tables that are strongly associated with MainTable
    t—placeholder for a table
    t.timestamp—the last time table t was updated
    r—placeholder for a record
    r.guid—the globally unique identifier of record r

---

1. ModRecords = records in MainTable with timestamp > MainTable.timestamp
2. AssocTables = tables in database strongly associated with MainTable
3. Foreach table t in AssocTables:
4.     append records in t with timestamp > t.timestamp to ModRecords
5. Call Server Synchronization on MainTable with ClientID, ModRecords, and MainTable.timestamp
/* Wait for server response */
/* Server responds with a collection of records and a new timestamp */
6. Foreach table t in AssocTables and MainTable:
7.     Foreach record r returned by the server for t
8.         If there is an existing record in t with guid = r.guid
9.             Then
10.                 Update existing record with values from r
11.                 Write updated record to the database
12.         Else
13.             Insert record r into the database
14.     t.timestamp = timestamp returned by the server

---

Healthcare Server Synchronization Algorithm:
  Input
    SyncTable—the table to synchronize
    ModRecords—array of records from SyncTable (or its associated tables)
    last_sync—the last time SyncTable was synchronized by the calling cart station Local Variables:

AssocTables—other database tables that are strongly associated with SyncTable
t—placeholder for a table
r—placeholder for a record sent by the cart station
r.guid—the globally unique identifier of record r
r.timestamp—the last time record r was updated
ts—the current timestamp of the server
mints—smallest timestamp of the server
ReturnRecords—array of records from SyncTable (or its associated tables) modified in the server since last sync

```
1. mints = infinity
2. ReturnRecords = empty array
3. AssocTables = tables in database strongly associated with SyncTable
4. Foreach table t in AssocTables and SyncTable:
5.      ts = current server timestamp
6.      mints = minimum of ts and mints
7.      Foreach record r sent by the cart station for t:
8.          r.timestamp = ts
9.          If there is an existing record in t with guid = r.guid
10.         Then
11.             Let r2 be the existing record
12.             If there are table specific processing steps for t
13.             Then
14.                 Perform specific processing steps for r and r2
15.             Update existing record r2 with values from r
16.             Write updated record r2 to the server database
17.         Else
18.             Insert record r into the server database
19.     Begin Critical Region
20.         Increment current server timestamp
21.     End Critical Region
22.     append records in SyncTable or any table in AssocTables that
are relevant to the cart station and with timestamp > last_sync to
ReturnRecords
23. Return ReturnRecords and mints to the cart station
```

F. Administration Web Pages

The healthcare server provides a web interface that can be accessed from any computer at the institution (over a secure connection) using a web browser. This account- and password-protected interface, called the administration web pages, implements the present invention's administrative function, which allows (i) setting or changing institution data such as the institution's name, default pharmacy, and name of the DON, (ii) setting or changing institution preferences for the behavior of the cart station(s), (iii) setting or changing patient or staff data, (iv) viewing reports, (v) doctors to view patient orders, (vi) doctors to prescribe medications and orders, and (vii) scheduling of labs, scheduled procedures, assessments, etc., for patients throughout the facility.

Figure 57:
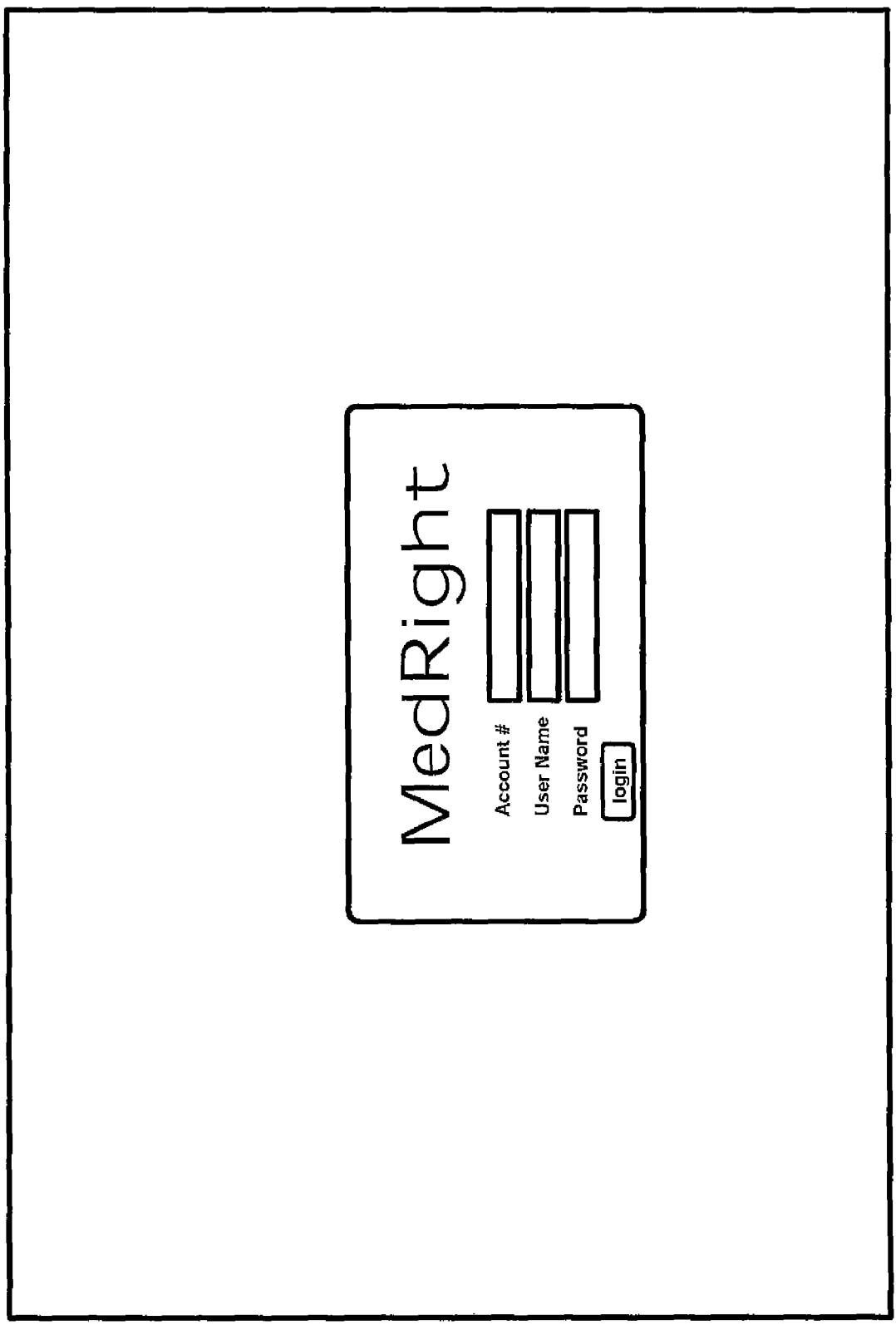
FIG. 57 is a screenshot of the administration web pages login screen.
Figure 58:
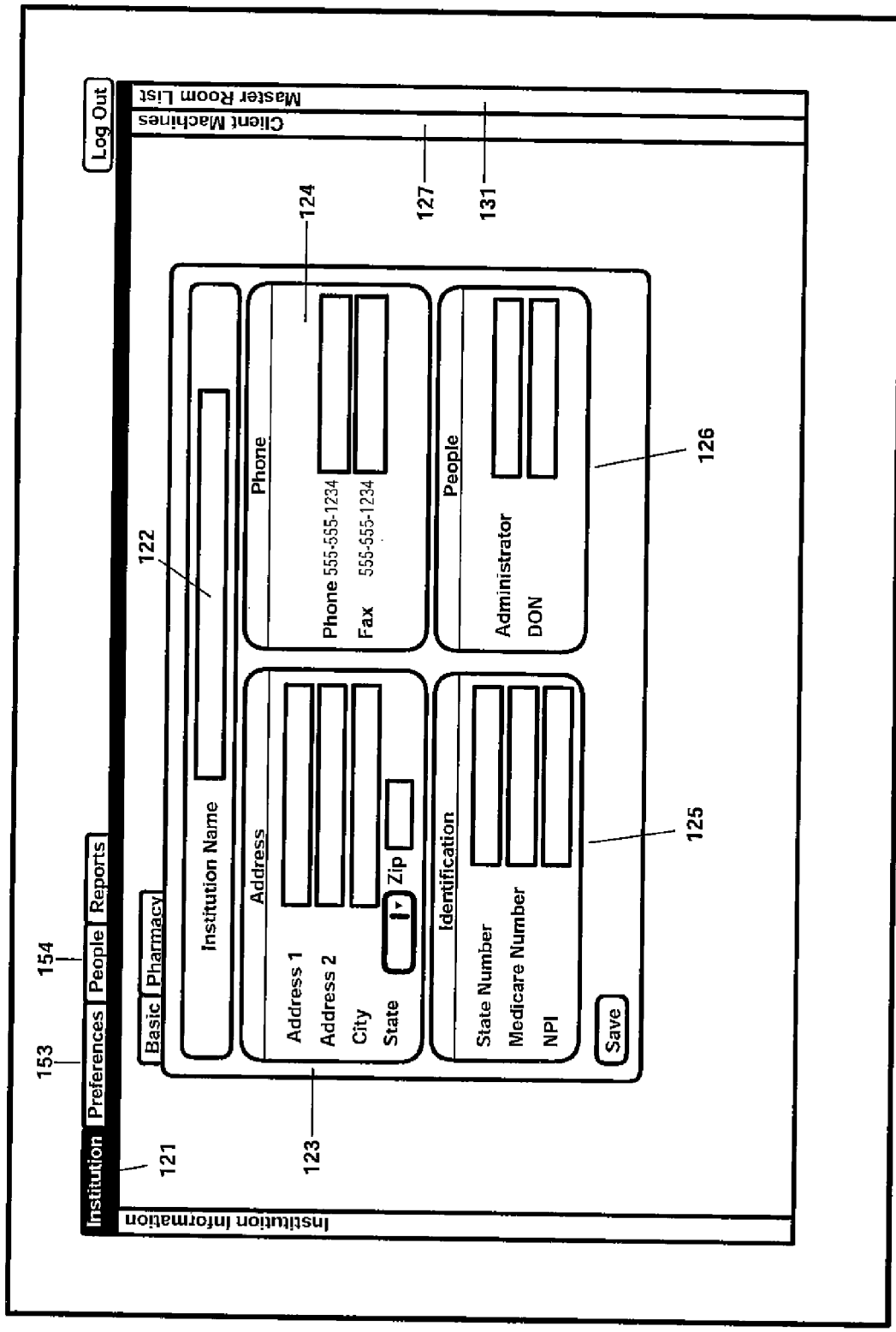
FIG. 58 is a screenshot of the institution information screen.
Figure 59:
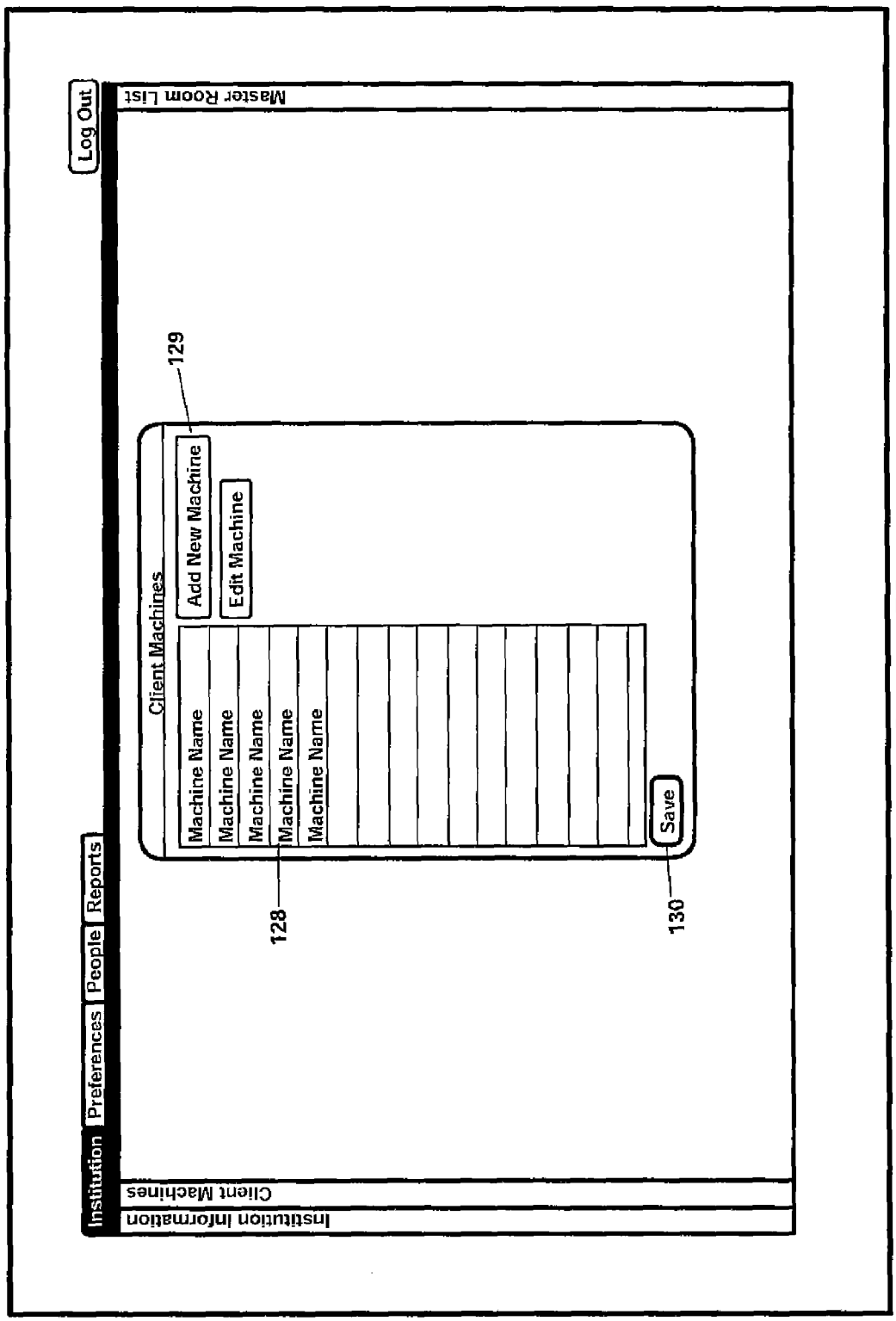
FIG. 59 is a screenshot of the cart station machines screen.
Figure 60:
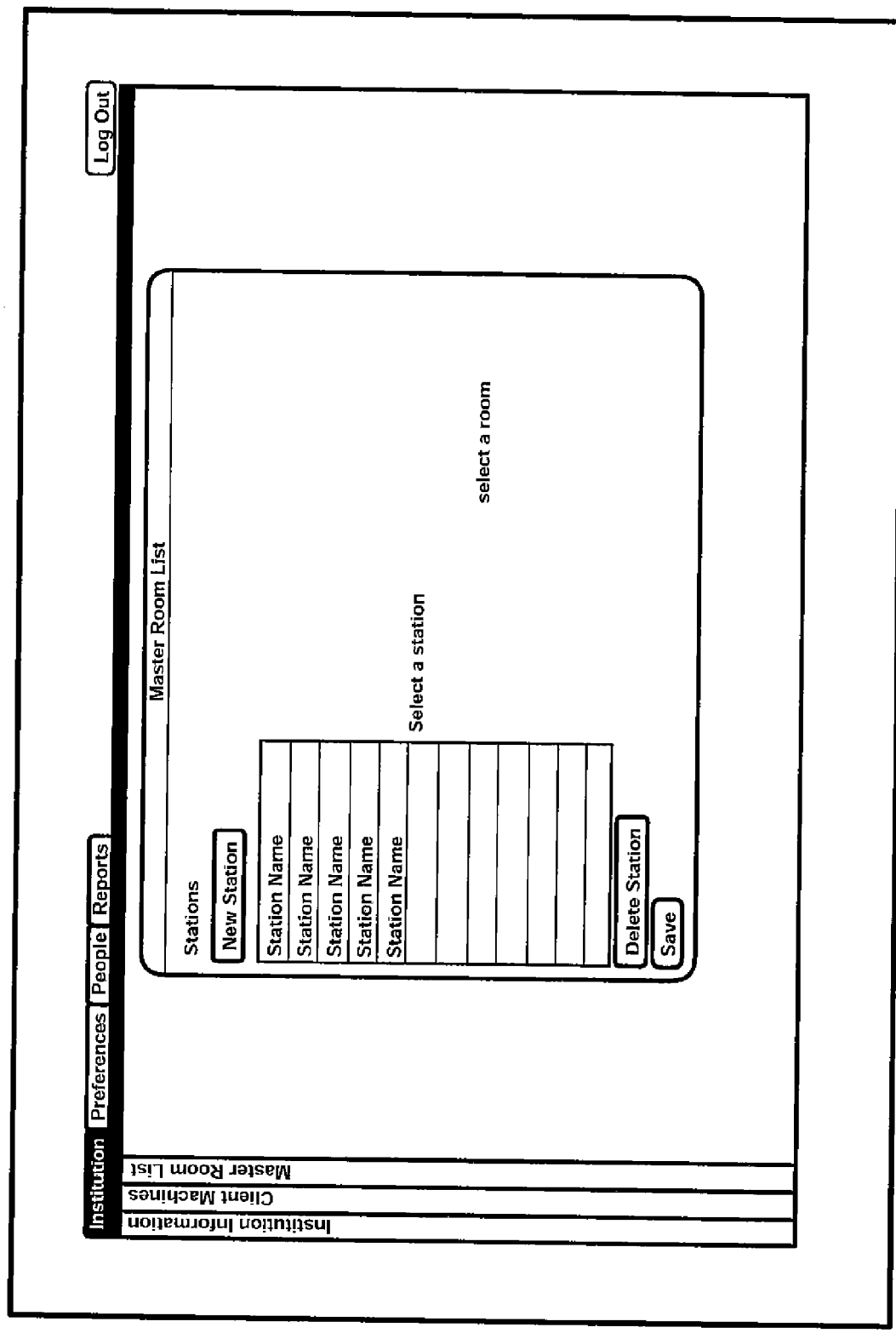
FIG. 60 is a screenshot of the master room list screen.

When the administration web pages are accessed, the login screen is shown (FIG. 57). Upon successful login, the institution information screen is shown (FIG. 58). This screen has four tabs on it with the institution tab 121 selected initially. The institution tab has three sections organized in an accordion: institution information, cart station machines (FIG. 59), and master room list (FIG. 60). The institution information screen is used to enter (modify) the institution name 122, address 123, phone and fax 124, and identification numbers 125, as well as to enter the name of the institution's DON 126.

Figure 61:
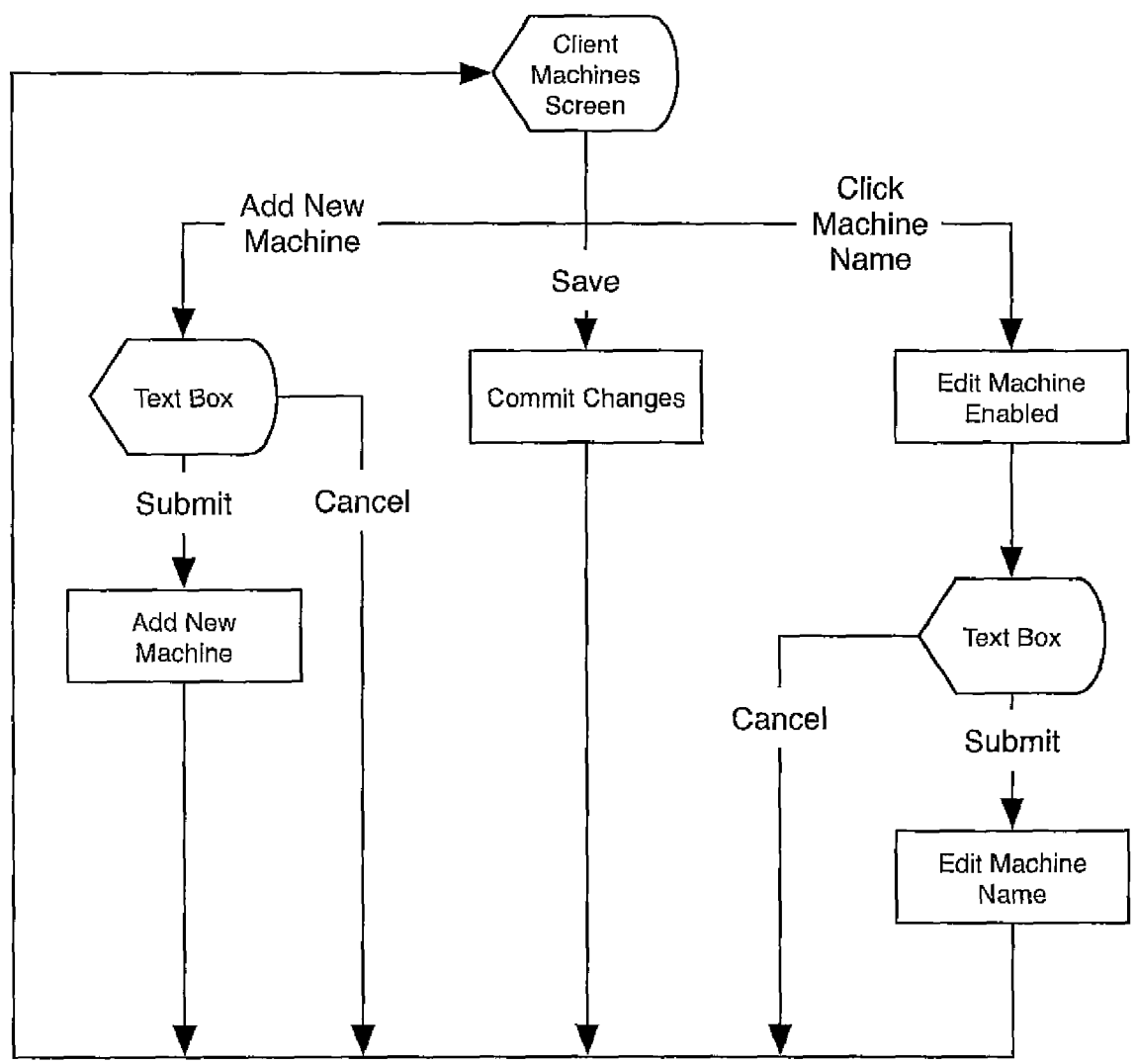
FIG. 61 is a diagram of the flow of the cart station machines screen.

The user can navigate to the call station machines section (FIG. 59) by clicking on the accordion tab with that label 127. This section displays a list of the institution's cart stations 128, along with buttons enabling new stations to be added and existing stations to be edited. A summary of the work flow on this screen is shown in FIG. 61. If the add new machine button 129 is clicked, a text box appears enabling the entry of the new machine's name. The user can enter the machine name and click the submit or cancel buttons. Machines in the list can be selected by clicking on them, in which case the edit machine button becomes enabled. The user can then click the button, and a text box is shown, allowing the user to edit the name of the machine. Once the user has completed any changes, the save button can be clicked and the changes committed.

Figure 62:
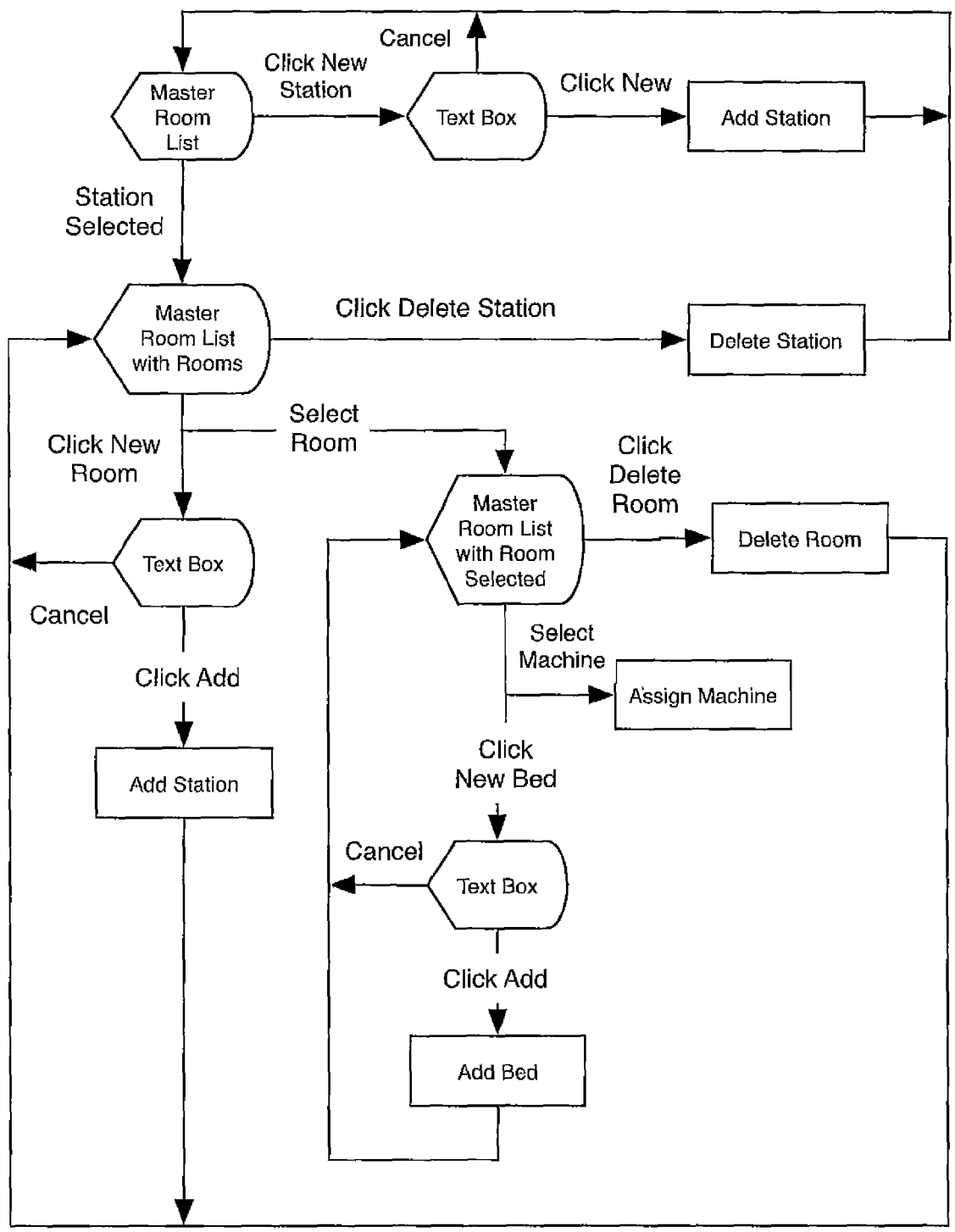
FIG. 62 is a diagram of the flow of the master room list screen.
Figure 63:
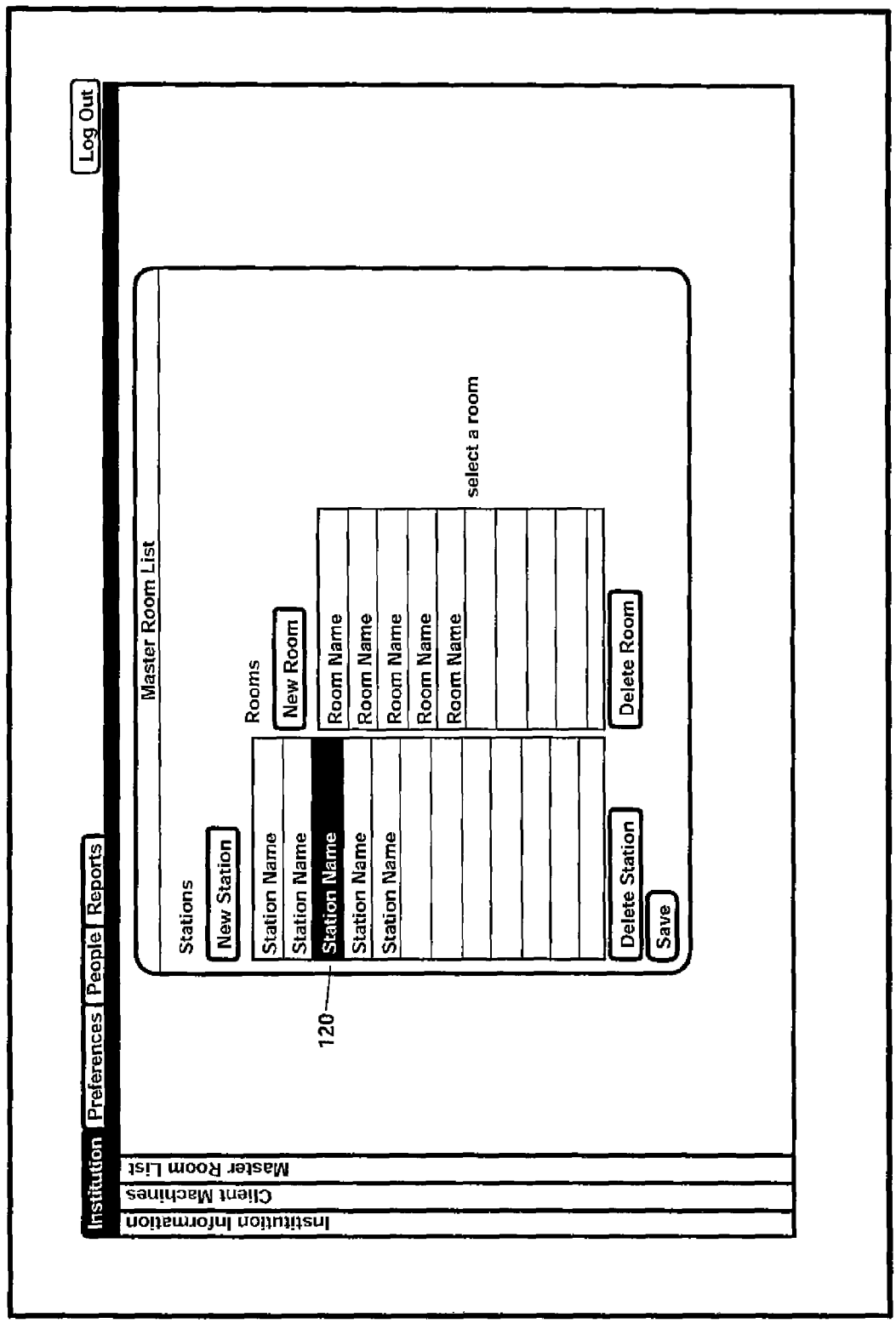
FIG. 63 is a screenshot of the master room list screen with a station selected.
Figure 64:
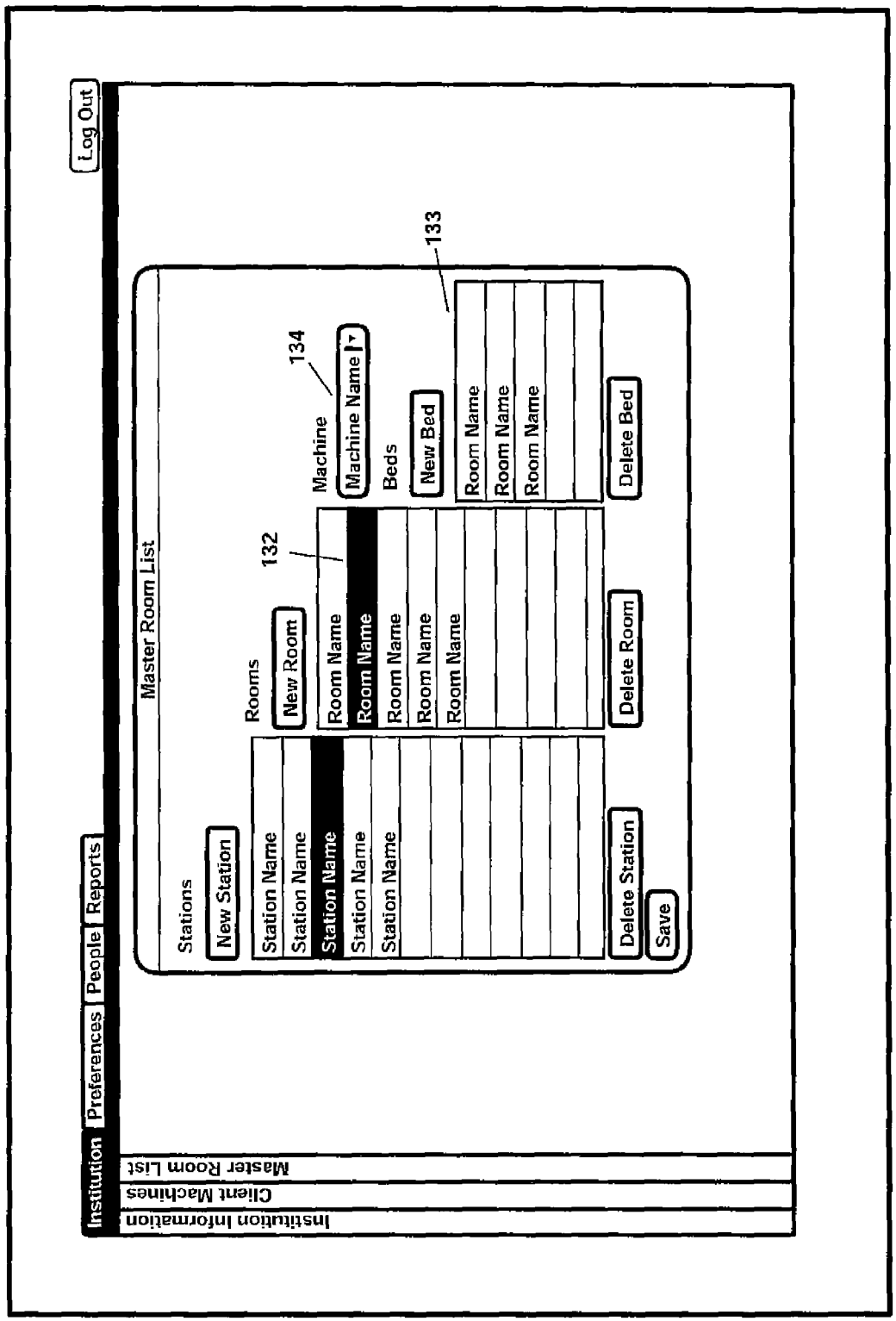
FIG. 64 is a screenshot of the master room list screen with a room selected.

The user can navigate to the master room list section (FIG. 60) by clicking on the accordion tab with that label 131. FIG. 62 shows the work flow on the master room list screen, which enables the user to manage the stations, rooms, and beds in the institution. Initially, this screen displays a list of the institution's stations. The user can add a new station, delete a station, or click on an existing station. Stations cannot be deleted if they have rooms in them. If an existing station is selected 120 on FIG. 63, a new list appears of rooms in that station. Rooms can be added, deleted, or selected. Rooms cannot be deleted if they have beds in them. If an existing room is selected 132 on FIG. 64, the list of the beds in that room and a button with the cart station to which the room is assigned appear 133. The machine name button 134 is a pulldown menu, allowing the user to change the machine to which the room is assigned. The user can also add or delete beds from the room. Beds cannot be deleted if they are occupied. When the user is satisfied with any changes, the save button can be clicked and the changes committed.

Figure 65:
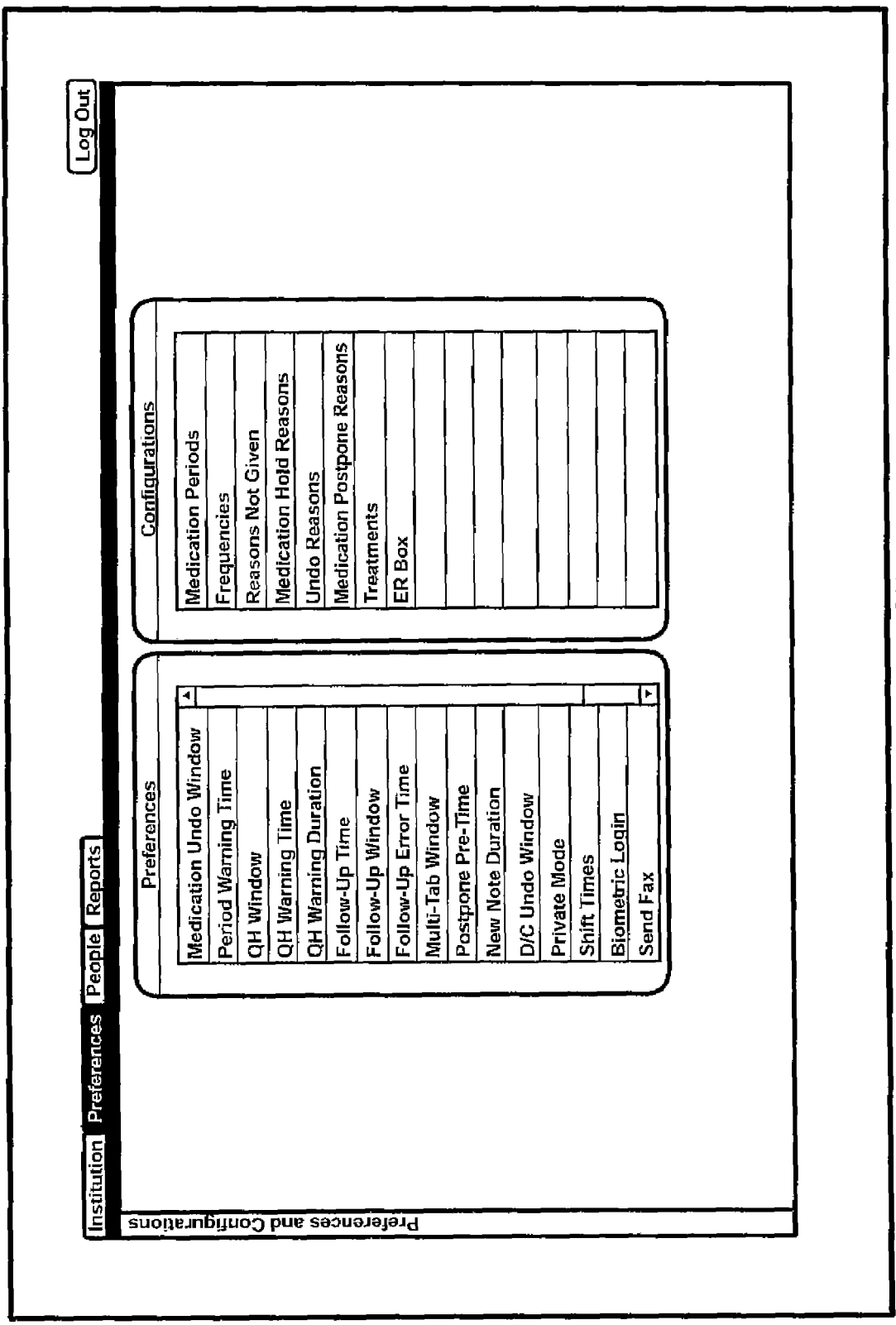
FIG. 65 is a screenshot of the preferences and configurations screen.
Figure 66:
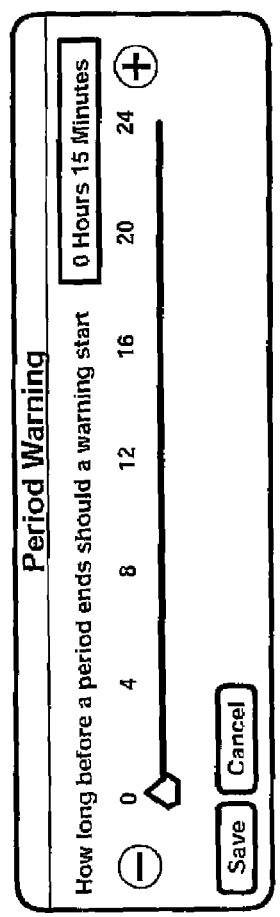
FIG. 66 is a screenshot of the period warning preference screen.
Figure 67:
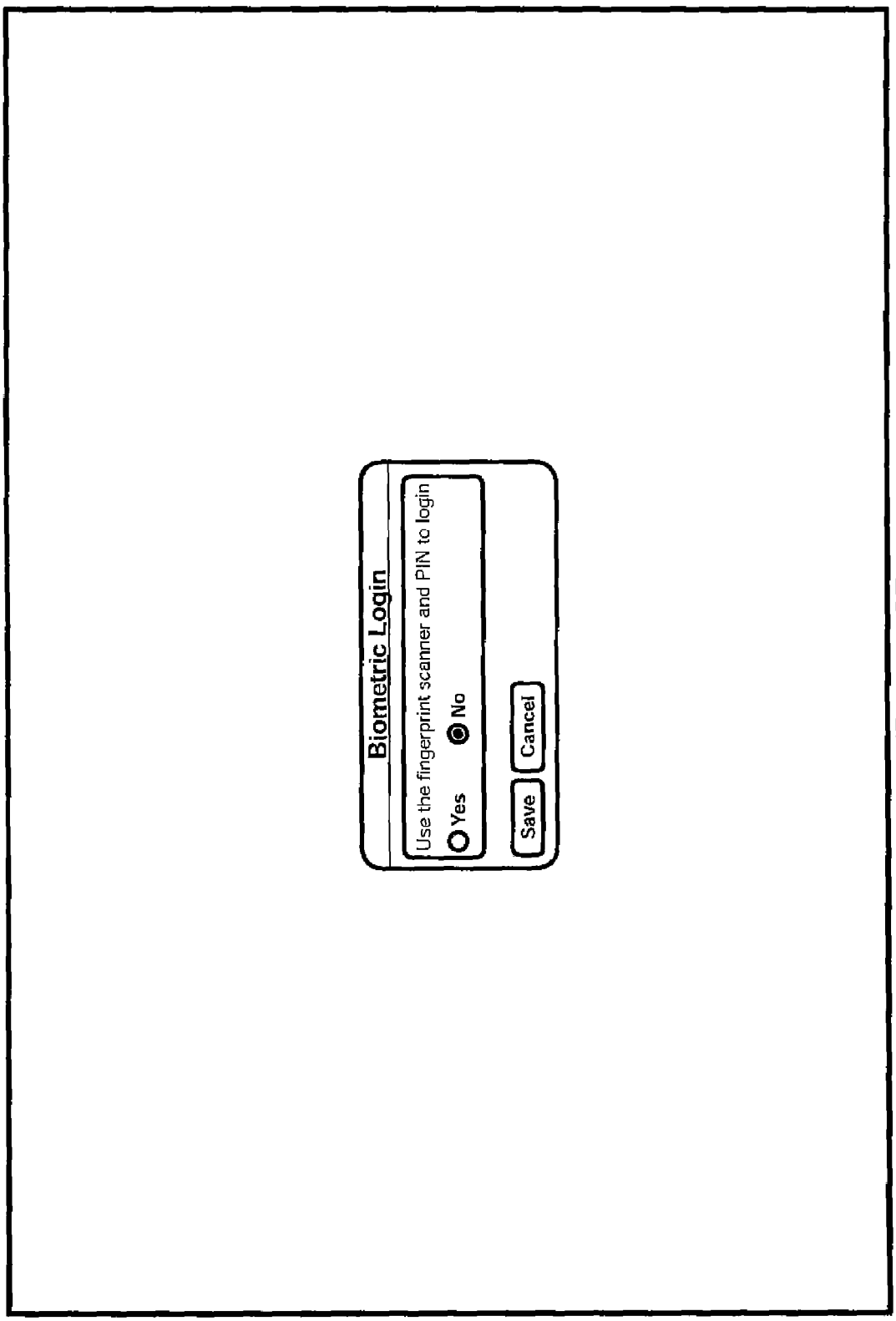
FIG. 67 is a screenshot of the biometric login preference screen.

If the preferences tab (153 on FIG. 58) is clicked, the preferences screen is displayed (FIG. 65). This screen contains a list of preferences and configuration parameters for the institution. In a preferred embodiment, the list of preferences includes: (i) medication undo window—the amount of time allowed for a medication to be undone after it is marked given or not given; (ii) period warning time—the amount of time prior to the end of each period after which warnings should pop up; (iii) QH window—the amount of time a QH medication is available to give; (iv) QH warning time—the amount of time before a QH medication becomes overdue after which a warning begins to pop up; (v) QH warning duration—the amount of time after the end of the QH window to continue displaying warnings; (vi) follow-up time—the amount of time after a PRN is given at which a follow-up is due; (vii) follow-up window—the amount of time in which a follow-up is available to complete; (viii) follow-up error time—how much time is allowed after a follow-up is due before an error is recorded; (ix) multi-tab window—the amount of time after part of a multi-tablet medication is given before the remainder of the dose is allowed to be given; (x) postpone pre-time—the amount of time that a medication can be postponed before it is due; (xi) new note duration—the number of days after creation during which a nurse note is considered new; (xii) D/C undo window—how long after a D/C order is placed during which it can be undone; (xiii) private mode—the period of time after which an idle cart station is automatically placed in private mode; (xiv) biometric login—whether or not fingerprint scans are required for login; and (xv) send fax—whether or not appropriate new orders coming from the cart station or administration web pages should be faxed to the pharmacy. With respect to (i) through (xiii), when the user clicks on the selection, a screen appears with a slider control that enables the current setting to be changed (see FIG. 66 for an example of (ii)). With respect to (xiv) and (xv), when the user clicks on the selection, the value can be set to yes or no (see FIG. 67 for an example of (xiv)).

In a preferred embodiment, the list of configurations includes: (i) medication periods—clicking on this allows the user to set or modify the institution's periods; (ii) frequencies—clicking on this displays a screen where the frequencies for the institution can be defined (modified); (iii) reasons not given—allows the user to manage the list of reasons that a medication is not given; (iv) medication hold reasons—allows the user to manage the list of reasons that a medication is held; (v) undo reasons—allows the user to manage the list of reasons that a given or not given medication is undone; (vi) postpone reasons—allows the user to manage the list of reasons that a medication is postponed; (vii) treatments—allows the user to manage the list of treatments available at the institution; and (viii) ER box—allows the user to manage the medications in the institution's ER box.

Figure 68:
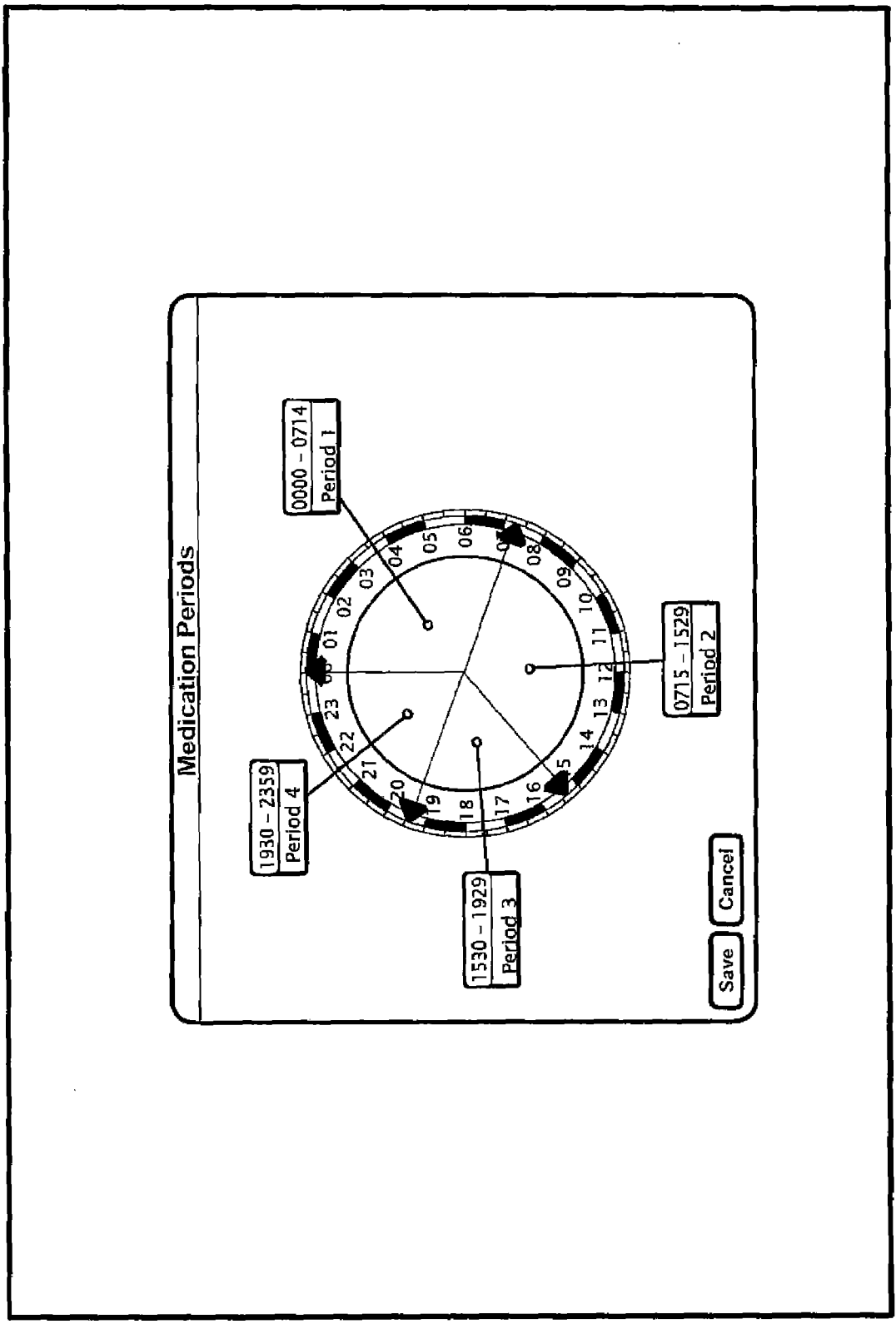
FIG. 68 is a screenshot of the medication periods screen.

With respect to (i), both the number of periods and each period duration can be set (changed) (see FIG. 68). With respect to (ii), the screen displays two lists (see FIG. 69): one of period frequencies and one of QH frequencies. Frequencies can be added to this list, or existing frequencies can be selected and edited. When a user selects "add new frequency," she is given a text box in which she can type the frequency name, and she is asked to indicate whether it is a period or QH frequency. If it is a period frequency, the user is asked to indicate how many times a day and in which periods procedures with this frequency are to be administered. If it is a QH frequency, the user is asked for the start time and interval. With respect to (iii), when a healthcare provider elects to not give a medication, she must select a reason from this list (see FIG. 70). With respect to (iv) and (v), when a healthcare provider elects to hold a medication, she can select a reason from this list (see FIG. 29), modify this reason, or type in a different reason.

Figure 72:
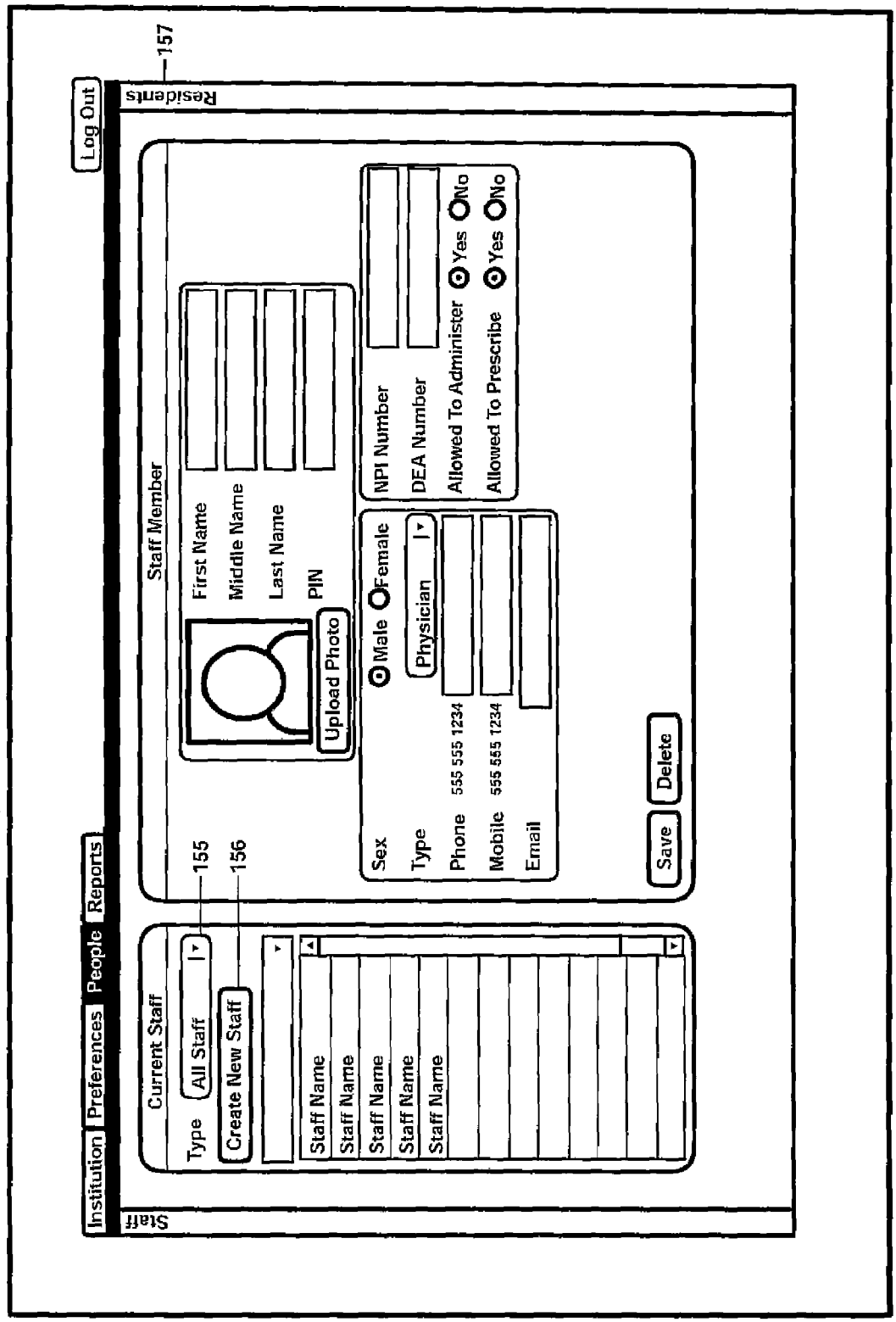
FIG. 72 is a screenshot of the people screen with staff showing.
Figure 73:
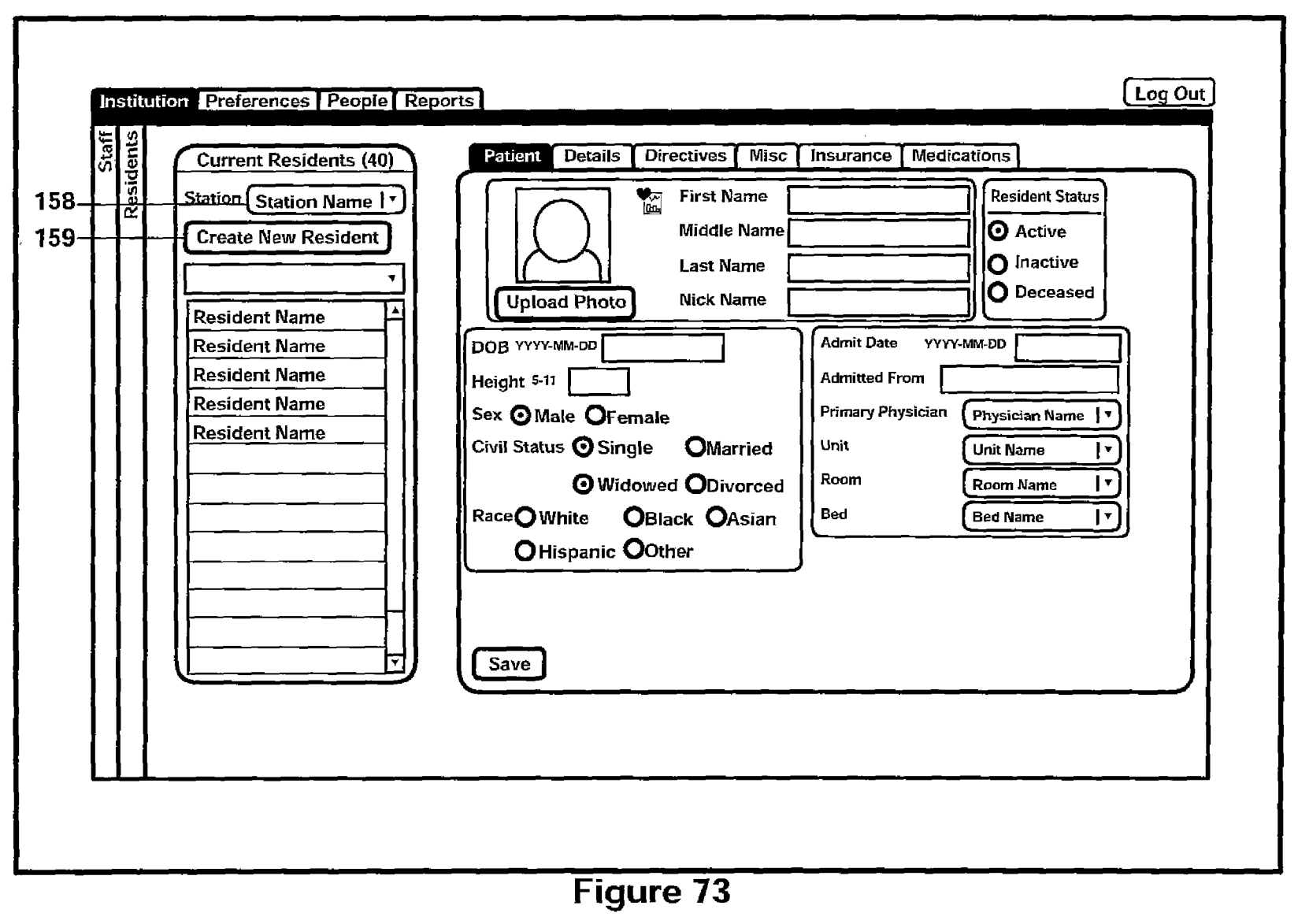

If the user clicks on the people tab (154 on FIG. 58), screens are displayed that enable the management of patients and staff at the institution. The top-level sections are organized in an accordion: one for staff (FIG. 72) and one for patients/residents (FIG. 73). The staff screen shows a list of the current staff members. There is a pulldown menu 155 for changing the display to show all staff or only certain categories of staff. The user can click a button 156 to create a new staff member or select an existing staff member from the list. If "create new staff" is clicked, text fields appear below the button enabling the new person's name to be entered, and a pulldown menu appears enabling the staff type to be selected.

When a staff member is selected, a form appears enabling the staff member to be deleted or data on the staff member to be set or modified. The data includes: the person's name, a photograph, PIN, gender, staff type, phone numbers, email, National Provider Identification ("NPI") number, Drug Enforcement Agency ("DEA") number, whether or not the staff member is allowed to administer medication, and whether or not the staff member is allowed to prescribe medication. Any changes can be committed by clicking on the save button.

Figure 74:
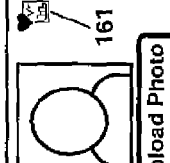
FIG. 74 is a screenshot of the people screen with a resident showing.

When the user clicks on the resident accordion section (157 on FIG. 72), a screen allowing management of residents slides into view. Some of the functionality on tabs on this screen is similar to functionality in the cart station, enabling the administration web pages user to perform many of the same functions available on the cart station. This section (FIG. 72) displays a list of residents and has a pulldown menu 158 for controlling the residents displayed in the list. All residents can be displayed or just the residents on a particular cart station. A button 159 is provided to enable new residents to be added. If an existing resident is selected, another tab-controlled area of the screen becomes enabled (FIG. 74) where several different kinds of data on residents can be viewed, entered, or modified. These data include: patient data, patient details, patient directives, pharmacy information and admission notes, insurance, and medications.

The patient tab (160 on FIG. 74) allows management of a patient's picture, name, status, date of birth, height, gender, civil status, race, admission date, where the patient was admitted from, primary physician, and bed to which the patient is assigned. There is also an icon in this section enabling the user to view charts of historical vitals data (161 on FIG. 74). The details tab 162 allows management of more detailed information on the patient, including: Social Security number, address, emergency contact information, diagnosis, allergies, and diet. The directives tab 163 enables management of the patient's directives, including: living will, feeding restrictions, durable power health care, do not resuscitate, durable power of attorney, do not hospitalize, medications restrictions, attorney-in-fact, organ donor, and other treatment restrictions. The miscellaneous tab (164 on FIG. 74) enables management of the pharmacy record number, facility record number, patient's pharmacy information, dentist, and admission notes. The insurance tab 165 enables management of the patient's insurance information. The medications tab 166 enables the management of the patient's medications.

Figure 75:
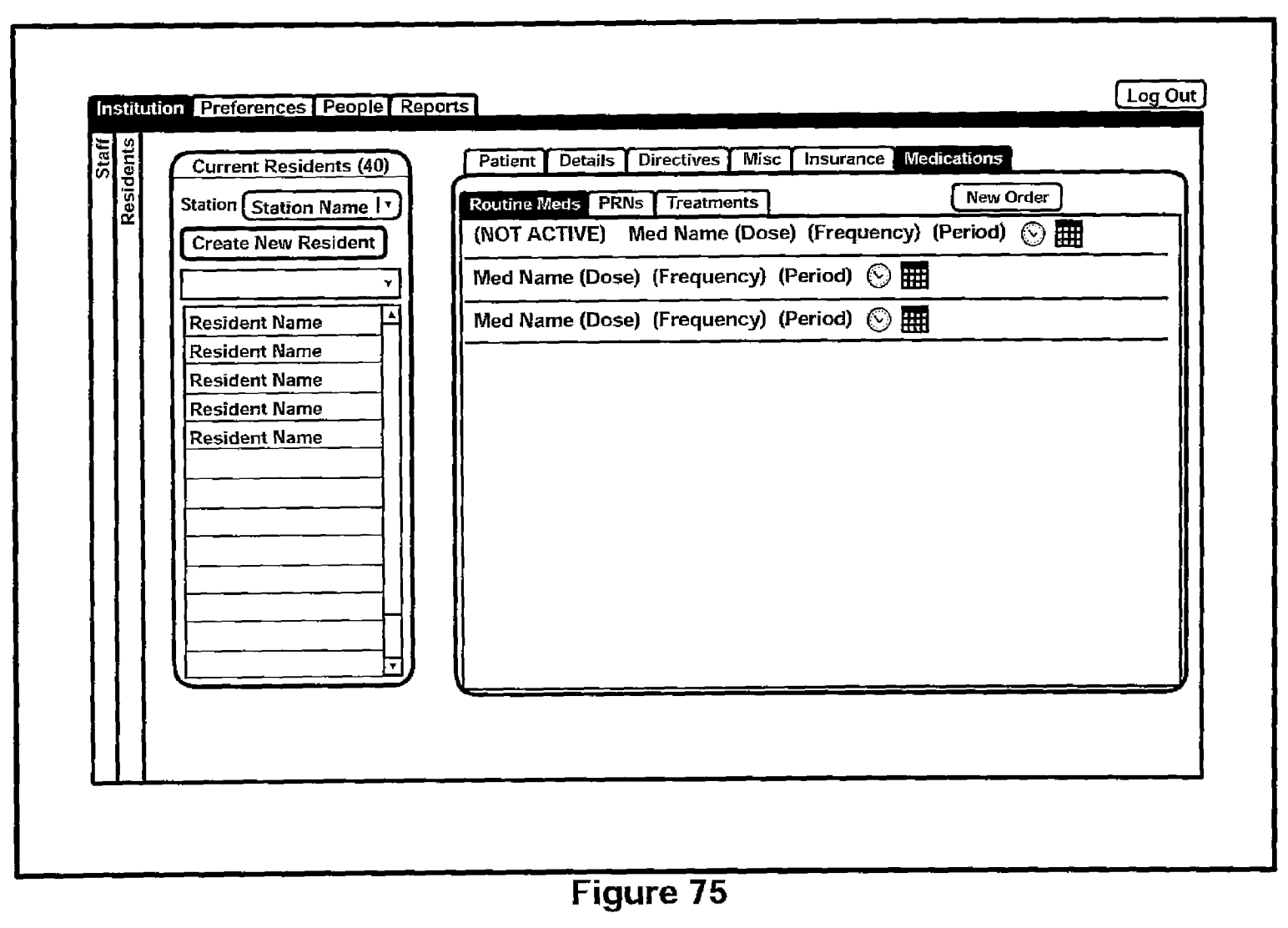

FIG. 75 is displayed when the medications tab (166 on FIG. 74) is clicked. This section displays information about routine medications and PRNs similarly to the patient profile screen on the cart station (FIG. 13). Additionally, the periods in which period medications are to be administered can be set on this screen. There is a new order button that, when clicked, displays a screen enabling new orders to be entered. This screen is similar to the new orders screen (FIG. 37) of the cart station, allowing new routine medications, PRNs, treatments, and scheduled procedures to be entered and orders to discontinue to be entered.

If the user clicks the reports tab, the user can then select a resident and obtain a MAR identical to the report generated by the cart station (see FIG. 50), except that as much as the last sixty days of data can be displayed in the report.

The scheduling screen enables the DON to view a calendar of activities for any patient in the facility. Activities shown include lab work, scheduled procedures, assessments, etc. The DON can also schedule these types of activities through the calendar (FIG. 76). Convenient functionality is provided, for example, to enable an activity to be scheduled once a month.

Physicians can also login to the administration web pages. In response, a screen is displayed enabling them to view the medications and other orders for their patients. Screens similar to the new orders screen are provided so that the physician can enter orders directly through the present invention. These orders go through the same work flow as all others in the invention so that, for example, a medication order entered in this manner will be faxed to the pharmacy if appropriate.

\* \* \*

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

REFERENCES

1. Bates, D. W. et al. "Incidence of adverse drug events and potential adverse drug events: implications for prevention." JAMA 1995; 274: 29-34.

2. Gurwitz, J. et al. "The incidence of adverse drug events in two large academic long-term care facilities." The American Journal of Medicine 2005; 118 (3): 251-8.

3. Johnson, J. A. et al. "Drug-related morbidity and mortality: a cost-of-illness model." Arch. Intern. Med. 1995; 155: 1949-1956.

4. "CMS' Strategic Action Plan 2006-2009: Centers for Medicare & Medicaid Services." U.S. Department of Health and Human Services, Washington, D.C.

5. Aspden, Philip. *Preventing Medication Errors*. Institute of Medicine (U.S.), Committee on Identifying and Preventing Medication Errors. National Academies Press, 2006. Appendix C, Table C-7.

We claim:

1. A system for electronic medication administration records comprising:

(a) a cart station with a cart station database;
(b) administration web pages; and
(c) a healthcare server with a healthcare server database;

wherein the cart station is located in a skilled nursing facility with patients, wherein the cart station utilizes a plan builder algorithm to build a plan for each patient based on data contained in the cart station database, and wherein the plan comprises a list of the patient's procedures for a given day and information indicating whether such procedures have been completed;

wherein the plan builder algorithm accounts for completed or missed procedure applications for a specified period prior to current time;

wherein the plan builder algorithm reads from the cart station database a list of each patient's procedure applications, historical data indicating whether or not the procedure application has been performed on a given day, and selected data about procedures previously performed; and wherein the plan builder algorithm also reads from the cart station database data associated with each procedure application, including type of procedure, start date, end date, hold date, frequency of application, prescribing physician, days of week on which the procedure should be performed, whether or not the procedure is active, prerequisite procedures of the procedure, type-specific attributes, and times of day or periods of day when the procedure is to be performed;

wherein the cart station utilizes a plan runner algorithm to maintain and update the plan for each patient;

wherein the plan runner algorithm ensures that no procedure is given before an allowed time;

wherein the plan runner algorithm ensures that no procedure is performed before its prerequisites are performed;

wherein the plan runner algorithm adds a subsequent application of a QH (Quaque Hora) procedure to the plan when a QH application is completed;

wherein the plan runner algorithm adds required dynamic procedures to the plan;

wherein the plan runner algorithm records all action on all procedure applications;

wherein the plan runner algorithm allows a procedure to be recorded as not given or done;

wherein the plan runner algorithm allows a procedure to be postponed and records when postponed procedures are next due;

wherein the plan runner algorithm records errors associated with procedures with period frequency that were due but not completed in a required period, procedures with QH frequencies that are overdue by more than a predefined period, prerequisites of procedures that are not completed, and follow-ups that are overdue by more than a predefined period; and wherein the plan runner algorithm notifies a user of pending application procedure errors;

wherein the administration web pages allow an administrator to manage utilization of the system;

wherein the healthcare server is not located at the skilled nursing facility, and wherein one or more skilled nursing facilities use the system; and wherein the healthcare server and the cart station utilize a synchronization algorithm to maintain accurate and timely data for all of the skilled nursing facilities that use the system;

wherein each cart station is assigned a unique ID, the cart station database contains data tables, the data tables contain records, each record is assigned a unique ID, and each record has a timestamp;

wherein the synchronization algorithm identifies records in the data tables and any associated data tables to be sent to the healthcare server from the cart station database;

where the identified records are sent by the cart station to the healthcare server;

wherein the healthcare server maintains a global timestamp;

wherein the synchronization algorithm determines whether a record received from the cart station database is already contained within the healthcare server database to determine whether it is a new or existing record;

wherein if the record is a new record, then it is added to the healthcare server database, and the timestamp for the record is set to the global timestamp;

wherein if the record is an existing record, then it is updated on the healthcare server to match the record received from the cart station, and the timestamp for the record is set to the global timestamp;

wherein if custom processing steps apply to a new or existing record, the synchronization algorithm performs the custom processing steps on the record;

wherein the global timestamp is incremented to a new value; and wherein the healthcare server sends to the cart station records that are relevant to patients assigned to the cart station based on the cart station ID and that have been modified as a result of synchronization, as determined by comparing the timestamp on the modified records to the timestamp of the records sent by the cart station.

2. The system of claim 1, wherein the cart station comprises a user display, and the plan runner ensures that the user display is accurate and accounts for events that occur in a given day;

wherein the plan runner ensures that no procedure is performed before its allowed time;

wherein a procedure may have one or more prerequisites, and the plan runner ensures that no procedure is performed before its prerequisites have been performed;

wherein when a procedure with a defined interval between applications of the procedure has been performed, the plan runner adds the next application of the procedure to the plan;

wherein the plan runner records when postponed procedures are due;

wherein the plan runner adds required dynamic procedures to the plan;

wherein the plan runner notifies a user of pending procedure application errors; and wherein the plan runner records actions on procedure applications.

3. The system of claim 1, wherein data is input into the cart station database from a pharmacy, through the administration web pages, or from the cart station itself;

wherein the cart station database comprises tables of records, each table has a timestamp that is an integer that encodes a date on which the table was last synchronized with the healthcare server, and each record has a timestamp that is an integer that encodes a date on which the record was last synchronized with the healthcare server; and wherein the cart station ensures that each record in a table in the cart station database has been updated with data received from the healthcare server up to the date of the timestamp for that table.

4. The system of claim 3, wherein the system undergoes a series of synchronization sequences over a period of time;

wherein the cart station sends to the healthcare server all new records, all records containing data that has been updated since the last synchronization sequence, and all records that are related to said new or updated records;

wherein the healthcare server maintains a global timestamp that is used as an official notation of time for synchronization purposes for the healthcare server and all cart stations;

wherein the healthcare server receives the records sent from the cart station;

wherein if a record received by the healthcare server is a new record, the healthcare server adds the record to the healthcare server database and ascribes a timestamp to it;

wherein if a record received by the healthcare server is an existing record, the healthcare server updates the record in the healthcare server database to match the record from the cart station and ascribes a timestamp to the updated record;

wherein the healthcare server increments the global timestamp;

wherein the healthcare server sends back to the cart station only those records comprising data that has been modified since the last synchronization sequence;

wherein each record has a globally unique ID that is used by the cart station to determine whether the record is a new record or an updated record;

wherein the cart station stores the new and/or updated records in the cart station database; and wherein the timestamp associated with each new or updated record is updated to match the global timestamp ascribed to the record by the healthcare server.

5. The system of claim 4, wherein a synchronization sequence occurs whenever the care provider logs into or out of the cart station, whenever the care provider clicks on a synchronization button on the cart station, and/or whenever the cart station is idle for a pre-defined period of time.

6. The system of claim 1, wherein the plan builder algorithm is invoked after each login to a cart station.

7. The system of claim 1, further comprising a pharmacy server that transmits data to the healthcare server;

wherein the data transmitted from the pharmacy server to the healthcare server is downloaded to a cart station in connection with a synchronization sequence.

8. The system of claim 1, wherein the cart station is located on a medication cart at the skilled nursing facility.

9. The system of claim 1, wherein the cart station generates a medication administration record report that describes all activities performed on a patient over a specified period of time.

10. The system of claim 1, wherein the cart station generates an activity report that describes all activities performed on patients at the skilled nursing facility over a specified period of time.

11. The system of claim 1, wherein the cart station generates a medical doctor report that includes prescribed medications, most recent vital signs taken, and medications given for a particular patient.

12. A method for maintaining electronic medication administration records comprising:

(a) providing a cart station with a cart station database, wherein the cart station is located in a skilled nursing facility with patients, wherein the cart station utilizes a plan builder algorithm to build a plan for each patient based on data contained in the cart station database, wherein the plan comprises a list of the patient's procedures for a given day and information indicating whether such procedures have been completed, and wherein the cart station utilizes a plan runner algorithm to maintain and update the plan for each patient;

wherein the plan builder algorithm accounts for completed or missed procedure applications for a specified period prior to current time;

wherein the plan builder algorithm reads from the cart station database a list of each patient's procedure applications, historical data indicating whether or not the procedure application has been performed on a given day, and selected data about procedures previously performed;

wherein the plan builder algorithm also reads from the cart station database data associated with each procedure application, including type of procedure, start date, end date, hold date, frequency of application, prescribing physician, days of week on which the procedure should be performed, whether or not the procedure is active, prerequisite procedures of the procedure, type-specific attributes, and times of day or periods of day when the procedure is to be performed;

wherein the plan runner algorithm ensures that no procedure is given before an allowed time;

wherein the plan runner algorithm ensures that no procedure is performed before its prerequisites are performed;

wherein the plan runner algorithm adds a subsequent application of a QH (quaque hora) procedure to the plan when a QH application is completed;

wherein the plan runner algorithm adds required dynamic procedures to the plan;

wherein the plan runner algorithm records all action on all procedure applications;

wherein the plan runner algorithm allows a procedure to be recorded as not given or done;

wherein the plan runner algorithm allows a procedure to be postponed and records when postponed procedures are next due;

wherein the plan runner algorithm records errors associated with procedures with period frequency that were due but not completed in a required period, procedures with QH frequencies that are overdue by more than a predefined period, prerequisites of procedures that are not completed, and follow-ups that are overdue by more than a predefined period; and wherein the plan runner algorithm notifies a user of pending application procedure errors;

(b) providing administration web pages that allow an administrator to manage utilization of the method; and (c) providing a healthcare server with a healthcare database, wherein the healthcare server is not located at the skilled nursing facility, and wherein one or more skilled nursing facilities use the method;

wherein the healthcare server and the cart station utilize a synchronization algorithm to maintain accurate and timely data for all of the skilled nursing facilities that use the method;

wherein each cart station is assigned a unique ID, the cart station database contains data tables, the data tables contain records, each record is assigned a unique ID, and each record has a timestamp;

wherein the synchronization algorithm identifies records in the data tables and any associated data tables to be sent to the healthcare server from the cart station database;

where the identified records are sent by the cart station to the healthcare server;

wherein the healthcare server maintains a global timestamp;

wherein the synchronization algorithm determines whether a record received from the cart station database is already contained within the healthcare server database to determine whether it is a new or existing record;

wherein if the record is a new record, then it is added to the healthcare server database, and the timestamp for the record is set to the global timestamp;

wherein if the record is an existing record, then it is updated on the healthcare server to match the record received from the cart station, and the timestamp for the record is set to the global timestamp;

wherein if custom processing steps apply to a new or existing record, the synchronization algorithm performs the custom processing steps on the record;

wherein the global timestamp is incremented to a new value; and wherein the healthcare server sends to the cart station records that are relevant to patients assigned to the cart station based on the cart station ID and that have been modified as a result of synchronization, as determined by comparing the timestamp on the modified records to the timestamp of the records sent by the cart station.

13. The method of claim 12, wherein the cart station comprises a user display, and the plan runner ensures that the user display is accurate and accounts for events that occur in a given day;

wherein the plan runner ensures that no procedure is performed before its allowed time;

wherein a procedure may have one or more prerequisites, and the plan runner ensures that no procedure is performed before its prerequisites have been performed;

wherein when a procedure with a defined interval between applications of the procedure has been performed, the plan runner adds the next application of the procedure to the plan;

wherein the plan runner records when postponed procedures are due;

wherein the plan runner adds required dynamic procedures to the plan;

wherein the plan runner notifies a user of pending procedure application errors; and wherein the plan runner records actions on procedure applications.

14. The method of claim 12, wherein data is input into the cart station database from a pharmacy, through the administration web pages, or from the cart station itself;

wherein the cart station database comprises tables of records, each table has a timestamp that is an integer that encodes a date on which the table was last synchronized with the healthcare server, and each record has a timestamp that is an integer that encodes a date on which the record was last synchronized with the healthcare server; and wherein the cart station ensures that each record in a table in the cart station database has been updated with data received from the healthcare server up to the date of the timestamp for that table.

15. The method of claim 14, wherein the cart station database and healthcare server database undergo a series of synchronization sequences over a period of time;

wherein the cart station sends to the healthcare server all new records, all records containing data that has been updated since the last synchronization sequence, and all records that are related to said new or updated records;

wherein the healthcare server maintains a global timestamp that is used as an official notation of time for synchronization purposes for the healthcare server and all cart stations;

wherein the healthcare server receives the records sent from the cart station;

wherein if a record received by the healthcare server is a new record, the healthcare server adds the record to the healthcare server database and ascribes a timestamp to it;

wherein if a record received by the healthcare server is an existing record, the healthcare server updates the record in the healthcare server database to match the record from the cart station and ascribes a timestamp to the updated record;

wherein the healthcare server increments the global timestamp;

wherein the healthcare server sends back to the cart station only those records comprising data that has been modified since the last synchronization sequence;

wherein each record has a globally unique ID that is used by the cart station to determine whether the record is a new record or an updated record;

wherein the cart station stores the new and/or updated records in the cart station database; and wherein the timestamp associated with each new or updated record is updated to match the global timestamp ascribed to the record by the healthcare server.

16. The method of claim 15, wherein a synchronization sequence occurs whenever the care provider logs into or out of the cart station, whenever the care provider clicks on a synchronization button on the cart station, and/or whenever the cart station is idle for a pre-defined period of time.

17. The method of claim 12, wherein the plan builder algorithm is invoked after each login to a cart station.

18. The method of claim 12, further comprising a pharmacy server that transmits data to the healthcare server;

wherein the data transmitted from the pharmacy server to the healthcare server is downloaded to a cart station in connection with a synchronization sequence.

19. The method of claim 12, wherein the cart station is located on a medication cart at the skilled nursing facility.

20. The method of claim 12, wherein the cart station generates a medication administration record report that describes all activities performed on a patient over a specified period of time.

21. The method of claim 12, wherein the cart station generates an activity report that describes all activities performed on patients at the skilled nursing facility over a specified period of time.

22. The method of claim 12, wherein the cart station generates a medical doctor report that includes prescribed medications, most recent vital signs taken, and medications given for a particular patient.

* * * * *